United States Patent
Kennedy et al.

(10) Patent No.: US 12,428,670 B2
(45) Date of Patent: *Sep. 30, 2025

(54) METHODS AND SYSTEMS FOR ANALYZING NUCLEIC ACID MOLECULES

(71) Applicant: GUARDANT HEALTH, INC., Palo Alto, CA (US)

(72) Inventors: Andrew Kennedy, San Diego, CA (US); Stefanie Ann Ward Mortimer, Morgan Hill, CA (US); Helmy Eltoukhy, Atherton, CA (US); AmirAli Talasaz, Atherton, CA (US); Diana Abdueva, Orinda, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/625,882

(22) Filed: Apr. 3, 2024

(65) Prior Publication Data

US 2024/0279714 A1    Aug. 22, 2024

Related U.S. Application Data

(63) Continuation of application No. 18/061,898, filed on Dec. 5, 2022, now Pat. No. 11,952,616, which is a continuation of application No. 16/450,918, filed on Jun. 24, 2019, now Pat. No. 11,519,019, which is a continuation of application No. PCT/US2017/068329, filed on Dec. 22, 2017.

(60) Provisional application No. 62/550,540, filed on Aug. 25, 2017, provisional application No. 62/512,936, filed on May 31, 2017, provisional application No. 62/438,240, filed on Dec. 22, 2016.

(51) Int. Cl.
| | | |
|---|---|---|
| *C12Q 1/68* | (2018.01) | |
| *C12N 15/10* | (2006.01) | |
| *C12P 19/34* | (2006.01) | |
| *C12Q 1/6806* | (2018.01) | |
| *C12Q 1/6874* | (2018.01) | |
| *C12Q 1/6886* | (2018.01) | |

(52) U.S. Cl.
CPC ....... *C12Q 1/6806* (2013.01); *C12N 15/1065* (2013.01); *C12Q 1/6874* (2013.01); *C12Q 1/6886* (2013.01); *C12Q 2600/154* (2013.01)

(58) Field of Classification Search
CPC .................................................. C12Q 1/6869
See application file for complete search history.

(56) References Cited

U.S. PATENT DOCUMENTS

| | | |
|---|---|---|
| 6,582,908 B2 | 6/2003 | Fodor et al. |
| 7,537,898 B2 | 5/2009 | Bost et al. |
| 8,476,013 B2 | 7/2013 | Ehrich et al. |
| 9,598,731 B2 | 3/2017 | Talasaz |
| 9,850,523 B1 | 12/2017 | Chudova et al. |
| 10,612,088 B2 | 4/2020 | Shishkin et al. |
| 2001/0053519 A1 | 12/2001 | Fodor et al. |
| 2003/0152490 A1 | 8/2003 | Trulson et al. |
| 2010/0105049 A1 | 4/2010 | Ehrich et al. |
| 2010/0273165 A1 | 10/2010 | Ehrich et al. |
| 2011/0160078 A1 | 6/2011 | Fodor et al. |
| 2013/0157266 A1 | 6/2013 | Hanna et al. |
| 2014/0080715 A1 | 3/2014 | Lo et al. |
| 2014/0363815 A1 | 12/2014 | Dahl et al. |
| 2015/0044687 A1 | 2/2015 | Schmitt et al. |
| 2015/0197801 A1 | 7/2015 | Muir et al. |
| 2015/0299812 A1 | 10/2015 | Talasaz |
| 2016/0047001 A1 | 2/2016 | Larisch et al. |
| 2016/0201142 A1 | 7/2016 | Lo et al. |
| 2018/0120304 A1 | 5/2018 | Rao et al. |
| 2018/0251848 A1 | 9/2018 | Diehn et al. |

FOREIGN PATENT DOCUMENTS

| | | |
|---|---|---|
| CN | 102648292 A | 8/2012 |
| EP | 2805769 A1 | 11/2014 |
| JP | 2015521862 A | 8/2015 |
| WO | 2011034631 A1 | 3/2011 |
| WO | 2015061359 A1 | 4/2015 |
| WO | 2015159292 A2 | 10/2015 |
| WO | 2016015058 A2 | 1/2016 |
| WO | 2016115530 A1 | 7/2016 |
| WO | 2016176091 A1 | 11/2016 |
| WO | 2017181161 A1 | 10/2017 |
| WO | 2017184707 A1 | 10/2017 |
| WO | 2017190215 A1 | 11/2017 |
| WO | 2018005811 A1 | 1/2018 |

(Continued)

OTHER PUBLICATIONS

Bock, C. et al. "Quantitative comparison of genome-wide DNA methylation mapping technologies" Nature Biotech (2010) 28:1106-1114.

(Continued)

*Primary Examiner* — Kenneth R Horlick
(74) *Attorney, Agent, or Firm* — Indhu Kanakaraj

(57) ABSTRACT

The disclosure provides methods for processing nucleic acid populations containing different forms (e.g., RNA and DNA, single-stranded or double-stranded) and/or extents of modification (e.g., cytosine methylation, association with proteins). These methods accommodate multiple forms and/or modifications of nucleic acid in a sample, such that sequence information can be obtained for multiple forms. The methods also preserve the identity of multiple forms or modified states through processing and analysis, such that analysis of sequence can be combined with epigenetic analysis.

23 Claims, 42 Drawing Sheets

Specification includes a Sequence Listing.

(56) References Cited

FOREIGN PATENT DOCUMENTS

| WO | 2018009723 A1 | 1/2018 |
|---|---|---|
| WO | 2019010564 A1 | 1/2019 |

OTHER PUBLICATIONS

Burnham, P. et al. "Single-stranded DNA library preparation uncovers the origin and diversity of ultrashort cell-free DNA in plasma" Sci Reports (Jun. 14, 2016) 6(1), XP055472868, DOI: 10.1038/srep27859.

Chinese Office Action dated Nov. 1, 2023 for CN2017800871305.

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Dey, S.S. et al. "Integrated genome and transcriptome sequencing of the same cell" Nature Biotech (Jan. 19, 2015) 33(3):285-589.

European Exam Report dated Aug. 20, 2020 for 17832453.9.

European Exam Report dated for 17832453.9, dated Aug. 5, 2022.

Gansauge, M-T. et al. "Single-stranded DNA library preparation for the sequencing of ancient or damaged DNA" Nature Protocols (2013) 3:737-748.

Indian Office Action for IN Application No. 201917024437, dated Sep. 16, 2021.

International search report and written opinion dated Jul. 9, 2019 for PCT/US2017/068329.

Iurlaro, M. et al. "A screen for hydroxymethylcytosine and formylcytosine binding proteins suggests functions in transcription and chromatin regulation" Genome Biology (2013) 14:R119.

Japanese office action dated Oct. 4, 2022 for JP2019-533331.

Japanese office action dated Nov. 30, 2021 for JP2019-533331.

Jeong, H.M. et al. "Efficiency of methylated DNA immunoprecipitation bisulphite sequencing for whole-genome DNA methylation analysis" Epigenomics (2016) 8(8):1061-1077.

Jin, H. et al. "Circulating Methylated DNA as Biomarkers for Cancer Detection" Methylation: From DNA, RNA and Histones to Diseases and Treatment (2012) InTech. XP055479454, DOI:10.5772./51419.

Korean Notice of Preliminary Rejection for KR Application No. 10-2019-7020828 dated Sep. 21, 2022.

Nair, S. et al. "Enzymatic cleavage of uracil-containing single-stranded DNA linkers for the efficient release of affinity-selected circulating tumor cells" Chem Commun (2015) 51(15):3266-3269.

Newman, et al. An ultrasensitive method for quantitating circulating tumor DNA with broad patient coverage. Nat Med. May 2014;20(5):548-54. doi: 10.1038/nm.3519. Epub Apr. 6, 2014.

Niazi, U. et al. "Dismiss: detection of stranded methylation in MeDIP-Seq data" BMC Bioinformatics (2016) 17:295 12 pages.

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Phallen, J. et al. "Direct detection of early-stage cancers using circulating tumor DNA" Sci Trans Med (2017) vol. 9, Issue 403, eaan2415DOI: 10.1126/scitranslmed.aan2415.

Reuter, J.A. et al. "Simul-seq: combined DNA and RNA sequencing for whole-genome and transcriptome profiling", Nature Methods (Oct. 10, 2016) 13(11):953-958.

Riebler, A. et al. "BayMeth: improved DNA methylation quantification for affinity capture sequencing data using a flexible Bayesian approach" Genome Biology (2014) 15:R35 19 pages.

Robinson, M.D. et al. "Evaluation of affinity-based genome-wide DNA methylation data: Effects of CpG density, amplification bias, and copy number variation" Genome Research (2010) 20(12):1719-1729.

Rohland, N. et al. "Cost-effective, high-throughput DNA sequencing libraries for multiplexed target capture" Genome Res (2012) 22(5):939-946.

Singapore Office Action for SG application No. 11201904597S, dated Oct. 5, 2020.

Smallwood, S.A. et al. "Single-cell genome-wide bisulfite sequencing for assessing epigenetic heterogeneity" Nature Methods (2014) 11(8):817-820.

Song, C-X. et al. "Selective chemical labeling reveals the genome-wide distribution of 5-hydroxymethylcytosine" Nature Biotech (2011) 29:68-72.

Stirzaker, C. et al. "Methylome sequencing in triple-negative breast cancer reveals distinct methylation clusters with prognostic value" Nature Comm (2015) 6(5899) (15 pages).

Suzuki, H. et al. "Genome-wide Profiling of Chromatin Signatures Reveals Epigenetic Regulation of MicroRNA Genes in Colorectal Cancer" Cancer Research (2011) 71(17):5646-5658.

Thakur, B.K. et al. "Double-stranded DNA in exosomes: a novel biomarker in cancer detection" Cell Research—Xibao Yanjiu (Apr. 8, 2014) 24(6):766-769.

Warton, K. et al. "Methylation of cell-free circulating DNA in the diagnosis of cancer" Frontiers in Mol Biosciences (2015) 2(13), 10 pages.

Warton, K. et al. "Methylation-capture and Next-Generation Sequencing of free circulating DNA from human plasma" BMC Genomics (2014) 15:476 13 pages.

Wielscher, M. et al. "Methyl-binding domain protein-based DNA isolation from human blood serum combines DNA analyses and serum-autoantibody testing" BMC Clin Path (2011) 11:11 (9 pages).

Yigit, E. et al. "Genome and metagenome sequencing: Using the human methyl-binding domain to partition genomic DNA derived from plant tissues" Appl Plant Sci (2014) 2(11):1400064.

Zhao, Y. et al. "Methylcap-Seq Reveals Novel DNA Methylation Markers for the Diagnosis and Recurrence Prediction of Bladder Cancer in a Chinese Population" PLoS One 7(4):e35175 (12 pages) (2012).

European Exam Report for EP Application No. 17832453.9, dated Oct. 24, 2024.

Japanese office action dated Nov. 11, 2024 for JP2023-60942.

Newman, A. et al. "Integrated digital error suppression for improved detection of circulating tumor DNA" Nature Biotech (2016) 34(5):547-555.

Non-final Office Action for U.S. Appl. No. 18/770,271, mailed Nov. 18, 2024.

Non-final Office Action for U.S. Appl. No. 18/770,298, mailed Nov. 22, 2024.

Non-final Office Action for U.S. Appl. No. 19/025,566, dated Mar. 12, 2025.

Non-final Office Action for U.S. Appl. No. 19/029,558, dated Mar. 24, 2025.

*Guardant Health* vs. *Tempus AI, Inc.* Complaint dated Aug. 12, 2025 (C.A. No. 1:2025cv01013).

1. Use 8 Lung Cancer no MBD samples to identify dyad centers

2. Isolate canonical nucleosomes with well positioned dyad and high occupancy (cov>.5Qu & peak width <.5Qu).

3. Locate dyad centers in combined MBD samples

4. Compare no MBD vs MBD aligned samples to calculate dyad center distances.

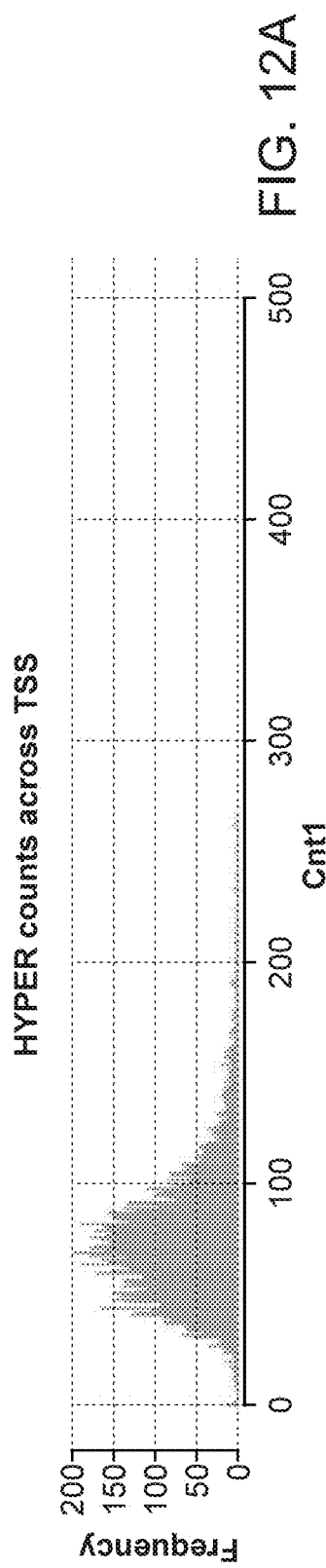
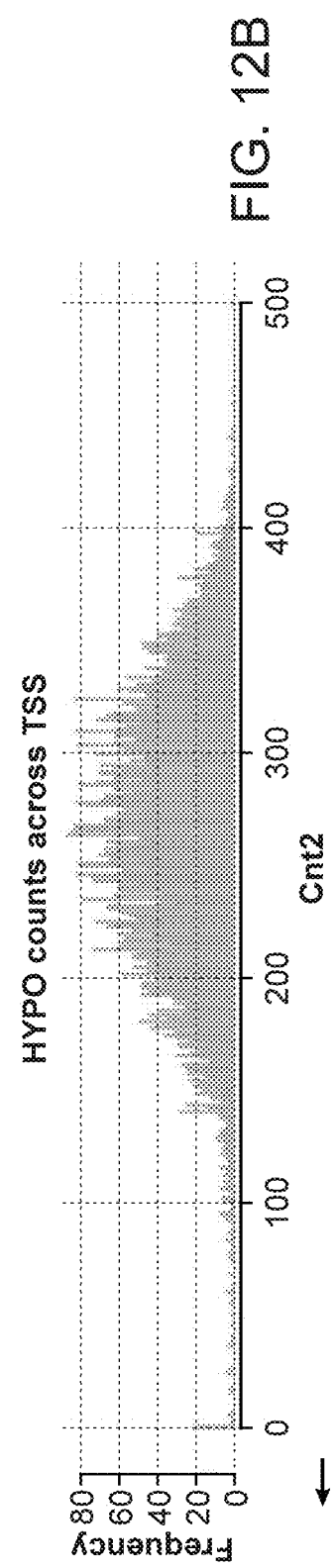
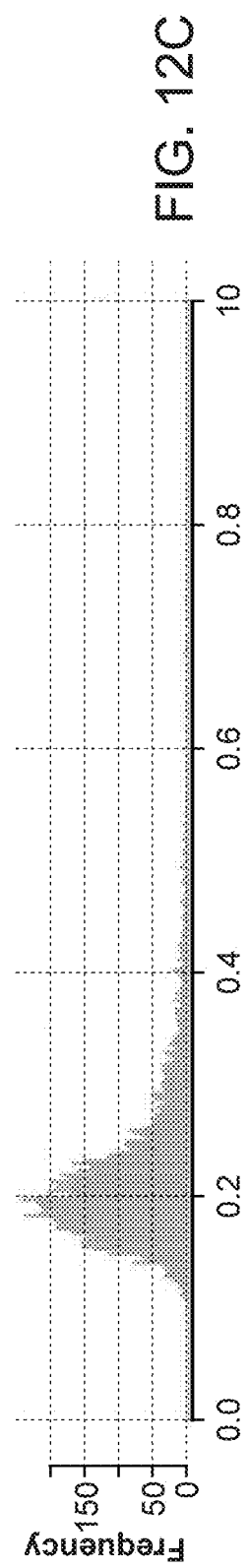
FIG. 12A
FIG. 12B
FIG. 12C

SEQUENCE LISTING

```
Sequence total quantity: 2
SEQ ID NO: 1          moltype = DNA  length = 58
FEATURE               Location/Qualifiers
source                1..58
                      mol_type = other DNA
                      organism = synthetic construct
SEQUENCE: 1
aatgatacgg cgaccaccga gatctacact ctttccctac acgacgctct tccgatct      58

SEQ ID NO: 2          moltype = DNA  length = 63
FEATURE               Location/Qualifiers
```

```
source          1..63
                mol_type = other DNA
                organism = synthetic construct
SEQUENCE: 2
gatcggaaga gcacacgtct gaactccagt cacnnnnnna tctcgtatgc cgtcttctgc   60
ttg                                                                 63
```

METHODS AND SYSTEMS FOR ANALYZING NUCLEIC ACID MOLECULES

REFERENCE TO RELATED PATENT APPLICATIONS

This application is a continuation application of U.S. Utility application Ser. No. 18/061,898, filed Dec. 5, 2022, now U.S. Pat. No. 11,952,616, which is a continuation application of U.S. Utility application Ser. No. 16/450,918, filed Jun. 24, 2019, now U.S. Pat. No. 11,519,019, which is a continuation of International Patent Application No. PCT/US2017/068329, filed Dec. 22, 2017, which claims the benefit of the priority dates of U.S. Provisional Patent Application Nos. 62/438,240, filed Dec. 22, 2016; 62/512,936, filed May 31, 2017 and 62/550,540, filed Aug. 25, 2017, all of which are incorporated by reference herein in their entirety.

SEQUENCE LISTING

The instant application contains a Sequence Listing which has been filed electronically in XML format and is hereby incorporated by reference in its entirety. Said XML copy, created on Jun. 22, 2023, is named GH0024US-CON42534-756_302_SL.xml and is 2,912 bytes in size.

BACKGROUND

Cancer is a major cause of disease worldwide. Each year, tens of millions of people are diagnosed with cancer around the world, and more than half eventually die from it. In many countries, cancer ranks the second most common cause of death following cardiovascular diseases. Early detection is associated with improved outcomes for many cancers.

Cancer can be caused by the accumulation of genetics variations within an individual's normal cells, at least some of which result in improperly regulated cell division. Such variations commonly include copy number variations (CNVs), single nucleotide variations (SNVs), gene fusions, insertions and/or deletions (indels), epigenetic variations include 5-methylation of cytosine (5-methylcytosine) and association of DNA with chromatin and transcription factors.

Cancers are often detected by biopsies of tumors followed by analysis of cells, markers or DNA extracted from cells. But more recently it has been proposed that cancers can also be detected from cell-free nucleic acids in body fluids, such as blood or urine. Such tests have the advantage that they are noninvasive and can be performed without identifying suspected cancer cells in biopsy. However, such tests are complicated by the fact that amount of nucleic acids in body fluids is very low and what nucleic acid are present are heterogeneous in form (e.g., RNA and DNA, single-stranded and double-stranded, and various states of post-replication modification and association with proteins, such as histones).

It is desirable to increase sensitivity of liquid biopsy assays while reducing the loss of circulating nucleic acid (original material) or data in the process.

SUMMARY

The disclosure provides methods, compositions and systems for analyzing a nucleic acid population comprising at least two forms of nucleic acid selected from double-stranded DNA, single-stranded DNA and single-stranded RNA. In some embodiments the method comprises (a) linking at least one of the forms of nucleic acid with at least one tag nucleic acid to distinguish the forms from one another, (b) amplifying the forms of nucleic acid at least one of which is linked to at least one nucleic acid tag, wherein the nucleic acids and linked nucleic acid tag, if present, are amplified, to produce amplified nucleic acids, of which those amplified from the at least one form are tagged; (c) assaying sequence data of the amplified nucleic acids at least some of which are tagged; and (d) decoding tag nucleic acid molecules of the amplified nucleic acids to reveal the forms of nucleic acids in the population providing an original template for the amplified nucleic acids linked to the tag nucleic acid molecules for which sequence data has been assayed.

In some embodiments, the method further comprises enriching for at least one of the forms relative to one or more of the other forms. In some embodiments at least 70% of the molecules of each form of nucleic acid in the population are amplified in step (b). In some embodiments at least three forms of nucleic acid are present in the population and at least two of the forms are linked to different tag nucleic acid forms distinguishing each of the three forms from one another. In some embodiments each of the at least three forms of nucleic acid in the population is linked to a different tag. In some embodiments each molecule of the same form is linked to a tag comprising the same identifying information tag (e.g., a tag with the same or comprising the same sequence). In some embodiments molecules of the same form are linked to different types of tags. In some embodiments step (a) comprises: subjecting the population to reverse transcription with a tagged primer, wherein the tagged primer is incorporated into cDNA generated from RNA in the population. In some embodiments the reverse transcription is sequence-specific. In some embodiments the reverse transcription is random. In some embodiments, the method further comprises degrading RNA duplexed to the cDNA. In some embodiments, the method further comprises separating single-stranded DNA from double-stranded DNA and ligating nucleic acid tags to the double-stranded DNA. In some embodiments the single-stranded DNA is separated by hybridization to one or more capture probes. In some embodiments, the method further comprises differentially tagging single-stranded DNA with a single-stranded tag using a ligase that functions on single stranded nucleic acids, and double-stranded DNA with double-stranded adapters using ligase that functions on double-stranded nucleic acids. In some embodiments, the method further comprises before assaying, pooling tagged nucleic acids comprising different forms of nucleic acid. In some embodiments, the method further comprises analyzing the pools of partitioned DNA separately in individual assays. The assays can be the same, substantially similar, equivalent, or different.

In any of the above methods, the sequence data can indicate presence of a somatic or germline variant, or a copy number variation or a single nucleotide variation, or an indel or gene fusion.

The disclosure further provides a method of analyzing a nucleic acid population comprising nucleic acids with different extents of modification. In some instances, the disclosure provides methods for screening for characteristics (e.g., 5' methylcytosine) associated with a disease. The method comprises contacting the nucleic acid population with an agent (such as a methyl binding domain or protein) that preferentially binds to nucleic acids bearing the modification; separating a first pool of nucleic acids bound to the agent from a second pool of nucleic acids unbound to the agent, wherein the first pool of nucleic acids are overrepresented for the modification, and the nucleic acids in the second pool are underrepresented for the modification; linking the nucleic acids in the first pool and/or second pool to one or more nucleic acid tags that distinguish the nucleic acids in the first pool and the second pool to produce a population of tagged nucleic acids; amplifying the tagged nucleic acids, wherein the nucleic acids and the linked tags are amplified; assaying sequence data of the amplified nucleic acids and linked tags; decoding the tags to reveal whether the nucleic acids for which sequence data has been assayed were amplified from templates in the first or second pool.

In some embodiments the modification is binding of nucleic acids to a protein. In some embodiments, the protein is a histone or transcription factor. In some embodiments, the nucleic acid modification is a post-replication modification to a nucleotide. In some embodiments, the post-replication modification is 5-methylcytosine, and the extent of binding of the capture agent to nucleic acids increases with the extent of 5-methylcytosines in the nucleic acid. In some embodiments, the post-replication modification is 5-hydroxymethylcytosine, and the extent of binding of the agent to nucleic acid increases with the extent of 5-hydroxymethylcytosine in the nucleic acid. In some embodiments, the post-replication modification is 5-formylcytosine or 5-carboxylcytosine and the extent of binding of the agent increases with the extent of 5-formylcytosine or 5-carboxylcytosine in the nucleic acid. In some embodiments, the post-replication modification is $N^6$-methyladenine. In some embodiments, the method further comprises washing nucleic acids bound to the agent and collecting the wash as a third pool including nucleic acids with the post replication modification at an intermediate extent relative to the first and second pools. Some methods further comprise, before assaying, pooling tagged nucleic acids from the first and second pools. In some embodiments, the agent comprises a methyl-binding domain or methyl-CpG-binding domain (MBD). The MBD can be a protein, an antibody or any other agent capable of specifically binding to modification of interest. Preferably, the MBD further comprises magnetic beads, streptavidin, or other binding domains for performing an affinity separation step.

The disclosure further provides a method for analyzing a nucleic acid population in which at least some of the nucleic acids include one or more modified cytosine residues. The method comprises linking capture moieties, e.g., biotin, to nucleic acids in the population to serve as templates for amplification; performing an amplification reaction to produce amplification products from the templates; separating the templates linked to capture moieties from amplification products; assaying sequence data of the templates linked to capture moieties by bisulfite sequencing; and assaying sequence data of the amplification products.

In some embodiments, the capture moieties comprise biotin. In some embodiments, the separating is performed by contacting the templates with streptavidin beads. In some embodiments the modified cytosine residues are 5-methylcytosine, 5-hydroxymethyl cytosine, 5-formyl cytosine or 5-carboxylcytosine. In some embodiments, the capture moieties comprise biotin linked to nucleic acid tags including one or more modified residues. In some embodiments, the capture moieties are linked to nucleic acid in the population via a cleavable linkage. In some embodiments, the cleavable linkage is a photocleavable linkage. In some embodiments, the cleavable linkage comprises a uracil nucleotide.

The disclosure further provides a method of analyzing a nucleic acid population comprising nucleic acids with different extents of 5-methylcytosine. The method comprises (a) contacting the nucleic acid population with an agent that preferentially binds to 5-methylated nucleic acids; (b) separating a first pool of nucleic acids bound to the agent from a second pool of nucleic acids unbound to the agent, wherein the first pool of nucleic acids are overrepresented for 5-methylcytosine, and the nucleic acids in the second pool are underrepresented for 5-methylation; (c) linking the nucleic acids in the first pool and/or second pool to one or more nucleic acid tags that distinguish the nucleic acids in the first pool and the second pool, wherein the nucleic acid tags linked to nucleic acids in the first pool comprise a capture moiety (e.g., biotin); (d) amplifying the labelled nucleic acids, wherein the nucleic acids and the linked tags are amplified; (e) separating amplified nucleic acids bearing the capture moiety from amplified nucleic acids that do not bear the capture moiety; and (f) assaying sequence data of the separated, amplified nucleic acids.

The disclosure further provides a method of analyzing a nucleic acid population comprising nucleic acids with different extents of modification, comprising: contacting the nucleic acids in the population with adapters to produce a population of nucleic acids flanked by adapters comprising primer binding sites; amplifying the nucleic acids flanked by adapters primed from the primer binding sites; contacting the amplified nucleic acids with an agent that preferentially binds to nucleic acids bearing the modification; separating a first pool of nucleic acids bound to the agent from a second pool of nucleic acids unbound to the agent, wherein the first pool of nucleic acids are overrepresented for the modification, and the nucleic acids in the second pool are underrepresented for the modification; performing a second amplification step of nucleic acids in the first and second pools; and assaying sequence data of the amplified nucleic acids in the first and second pools. Amplification of each pool can occur separately in different reaction vessels. Using pool specific tags allows for subsequent pooling of the amplicons prior to sequencing.

The disclosure further provides a method of analyzing a nucleic acid population in which at least some of the nucleic acids include one or more modified cytosine residues, comprising contacting the nucleic acid population with adapters comprising a primer binding site comprising at least one modified cytosine to form nucleic acids flanked by adapters; amplifying the nucleic acids flanked by adapters primed from the primer binding sites in the adapters flanking a nucleic acid; splitting the amplified nucleic acids into first and second aliquots; assaying sequence data on the nucleic acids of the first aliquot; contacting the nucleic acids of the second aliquot with bisulfite, which converts unmodified cytosines (C's) to uracils (U's); amplifying the nucleic acids resulting from bisulfite treatment primed from the primer binding sites flanking the nucleic acids, wherein U's introduced by bisulfite treatment are converted to T's; assaying sequence data on the amplified nucleic acids from the second aliquot; comparing the sequence data of the nucleic acids in the first and second aliquots to identify which nucleotides in the nucleic acid population were modified cytosines.

In any of the above methods, the nucleic acid population can be from a bodily fluid sample, such as blood, serum, or plasma. In some embodiments, the nucleic acid population is a cell free nucleic acid population. In some embodiments, the bodily fluid sample is from a subject suspected of having a cancer.

In one aspect provided herein is a method of analyzing a nucleic acid population comprising at least two forms of nucleic acid selected from double-stranded DNA, single-stranded DNA and single-stranded RNA, the method, wherein each of the at least two forms comprises a plurality of molecules, comprising: linking at least one of the forms of nucleic acid with at least one tag nucleic acid to distinguish the forms from one another, amplifying the forms of nucleic acid at least one of which is linked to at least one nucleic acid tag, wherein the nucleic acids and linked nucleic acid tag, are amplified, to produce amplified nucleic acids, of which those amplified from the at least one form are tagged; assaying sequence data of the amplified nucleic acids at least some of which are tagged; wherein the assaying obtains sequence information sufficient to decode the tag nucleic acid molecules of the amplified nucleic acids to reveal the forms of nucleic acids in the population providing an original template for the amplified nucleic acids linked to the tag nucleic acid molecules for which sequence data has been assayed. In one embodiment the method further comprises the step of decoding the tag nucleic acid molecules of the amplified nucleic acids to reveal the forms of nucleic acids in the population providing an original template for the amplified nucleic acids linked to the tag nucleic acid molecules for which sequence data has been assayed. In another embodiment the method further comprises enriching for at least one of the forms relative to one or more of the other forms. In another embodiment at least 70% of the molecules of each form of nucleic acid in the population are amplified. In another embodiment at least three forms of nucleic acid are present in the population and at least two of the forms are linked to different tag nucleic acid forms distinguishing each of the three forms from one another. In another embodiment each of the at least three forms of nucleic acid in the population is linked to a different tag. In another embodiment each molecule of the same form is linked to a tag comprising the same tag information. In another embodiment molecules of the same form are linked to different types of tags. In another embodiment the method further comprises subjecting the population to reverse transcription with a tagged primer, wherein the tagged primer is incorporated into cDNA generated from RNA in the population. In another embodiment the reverse transcription is sequence-specific. In another embodiment wherein the reverse transcription is random. In another embodiment the method further comprises degrading RNA duplexed to the cDNA. In another embodiment the method further comprises separating single-stranded DNA from double-stranded DNA and ligating nucleic acid tags to the double-stranded DNA. In another embodiment the single-stranded DNA is separated by hybridization to one or more capture probes. In another embodiment the method further comprises circularizing single-stranded DNA with a circligase and ligating nucleic acid tags to the double-stranded DNA. In another embodiment the method comprises, before assaying, pooling tagged nucleic acids comprising different forms of nucleic acid. In another embodiment the nucleic acid population is from a bodily fluid sample. In another embodiment the bodily fluid sample is blood, serum, or plasma. In another embodiment the nucleic acid population is a cell free nucleic acid population. In another embodiment the bodily fluid sample is from a subject suspected of having a cancer. In another embodiment the sequence data indicates presence of a somatic or germline variant. In another embodiment the sequence data indicates presence of a copy number variation. In another embodiment the sequence data indicates presence of a single nucleotide variation (SNV), indel or gene fusion. In another embodiment the sequence data indicates presence of a single nucleotide variation (SNV), indel or gene fusion.

In another aspect provided herein is method of analyzing a nucleic acid population comprising nucleic acids with different extents of modification, comprising: contacting the nucleic acid population with an agent that preferentially binds to nucleic acids bearing the modification, separating a first pool of nucleic acids bound to the agent from a second pool of nucleic acids unbound to the agent, wherein the first pool of nucleic acids is overrepresented for the modification, and the nucleic acids in the second pool are underrepresented for the modification; linking the nucleic acids in the first pool and/or second pool to one or more nucleic acid tags that distinguish the nucleic acids in the first pool and the second pool to produce a population of tagged nucleic acids; amplifying the labelled nucleic acids, wherein the nucleic acids and the linked tags are amplified; and, assaying sequence data of the amplified nucleic acids and linked tags; wherein the assaying obtains sequence data for decoding the tags to reveal whether the nucleic acids for which sequence data has been assayed were amplified from templates in the first or the second pool. In one embodiment the method comprises the step of decoding the tags to reveal whether the nucleic acids for which sequence data has been assayed were amplified from templates in the first or the second pool. In another embodiment the modification is binding of nucleic acids to a protein. In another embodiment the protein is a histone or transcription factor. In another embodiment the modification is a post-replication modification to a nucleotide. In another embodiment the post-replication modification is 5-methyl-cytosine, and the extent of binding of the agent to nucleic acids increases with the extent of 5-methyl-cytosines in the nucleic acid. In another embodiment the post-replication modification is 5-hydroxymethyl-cytosine, and the extent of binding of the agent to nucleic acid increases with the extent of 5-hydroxymethyl-cytosine in the nucleic acid. In another embodiment the post-replication modification is 5-formyl-cytosine or 5-carboxyl-cytosine and the extent of binding of the agent increases with the extent of 5-formyl-cytosine or 5-carboxyl-cytosine in the nucleic acid. In another embodiment the method further comprises washing nucleic acids bound to the agent and collecting the wash as a third pool including nucleic acids with the post replication modification at an intermediate extent relative to the first and second pools. In another embodiment the method comprises, before assaying, pooling tagged nucleic acids from the first and second pools. In another embodiment the agent is 5-methyl-binding domain magnetic beads. In another embodiment the nucleic acid population is from a bodily fluid sample. In another embodiment the bodily fluid sample is blood, serum, or plasma. In another embodiment the nucleic acid population is a cell free nucleic acid population. In another embodiment the bodily fluid sample is from a subject suspected of having a cancer. In another embodiment the sequence data indicates presence of a somatic or germline variant. In another embodiment the sequence data indicates presence of a copy number variation. In another embodiment the sequence data indicates presence of a single nucleotide variation (SNV), indel or gene fusion.

In another aspect provided herein is a method of analyzing a nucleic acid population in which at least some of the nucleic acids include one or more modified cytosine residues, comprising linking capture moieties to nucleic acids in the population, which nucleic acids serve as templates for amplification; performing an amplification reaction to produce amplification products from the templates; separating the templates linked to capture tags from amplification products; assaying sequence data of the templates linked to capture tags by bisulfite sequencing; and assaying sequence data of the amplification products. In one embodiment the capture moieties comprise biotin. In another embodiment the separating is performed by contacting the templates with streptavidin beads. In another embodiment the modified cytosine residues are 5-methyl-cytosine, 5-hydroxymethyl cytosine, 5-formyl cytosine or 5-carboxyl cytosine. In another embodiment the capture moieties comprise biotin linked to nucleic acid tags including one or more modified residues. In another embodiment the capture moieties are linked to nucleic acid in the population via a cleavable linkage. In another embodiment the cleavable linkage is a photocleavable linkage. In another embodiment the cleavable linkage comprises a uracil nucleotide. In another embodiment the nucleic acid population is from a bodily fluid sample. In another embodiment the bodily fluid sample is blood, serum, or plasma. In another embodiment the nucleic acid population is a cell free nucleic acid population. In another embodiment the bodily fluid sample is from a subject suspected of having a cancer. In another embodiment the sequence data indicates presence of a somatic or germline variant. In another embodiment the sequence data indicates presence of a copy number variation. In another embodiment the sequence data indicates presence of a single nucleotide variation (SNV), indel or gene fusion.

In another aspect provided herein is a method of analyzing a nucleic acid population comprising nucleic acids with different extents of 5-methylation, comprising: contacting the nucleic acid population with an agent that preferentially binds to 5-methyl-ated nucleic acids; separating a first pool of nucleic acids bound to the agent from a second pool of nucleic acids unbound to the agent, wherein the first pool of nucleic acids are overrepresented for 5-methylation, and the nucleic acids in the second pool are underrepresented for 5-methylation; linking the nucleic acids in the first pool and/or second pool to one or more nucleic acid tags that distinguish the nucleic acids in the first pool and the second pool, wherein the nucleic acid tags linked to nucleic acids in the first pool comprise a capture moiety (e.g., biotin); amplifying the labelled nucleic acids, wherein the nucleic acids and the linked tags are amplified; separating amplified nucleic acids bearing the capture moiety from amplified nucleic acids that do not bear the capture moiety; and assaying sequence data of the separated, amplified nucleic acids.

In another aspect provided herein is a method of analyzing a nucleic acid population comprising nucleic acids with different extents of modification, comprising: contacting the nucleic acids in the population with adapters to produce a population of nucleic acids flanked by adapters comprising primer binding sites; amplifying the nucleic acids flanked by adapters primed from the primer binding sites; contacting the amplified nucleic acids with an agent that preferentially binds to nucleic acids bearing the modification; separating a first pool of nucleic acids bound to the agent from a second pool of nucleic acids unbound to the agent, wherein the first pool of nucleic acids is overrepresented for the modification, and the nucleic acids in the second pool are underrepresented for the modification; performing parallel amplifications of tagged nucleic acids in the first and second pools; and assaying sequence data of the amplified nucleic acids in the first and second pools. In another embodiment the adapters are hairpin adapters.

In another aspect provided herein is a method of analyzing a nucleic acid population in which at least some of the nucleic acids include one or more modified cytosine residues, comprising contacting the nucleic acid population with adapters comprising a primer binding site comprising a modified cytosine to form nucleic acids flanked by adapters; amplifying the nucleic acids flanked by adapters primed from the primer binding sites in the adapters flanking a nucleic acid; splitting the amplified nucleic acids into first and second aliquots; assaying sequence data on the nucleic acids of the first aliquot; contacting the nucleic acids of the second aliquot with bisulfite, which converts unmodified C's to U; amplifying the nucleic acids resulting from bisulfite treatment primed from the primer binding sites flanking the nucleic acids, wherein U's introduced by bisulfite treatment are converted to T's; and, assaying sequence data of the amplified nucleic acids from the second aliquot; wherein the assaying produces sequence data that can be used to compare the sequence data of the nucleic acids in the first and second aliquot to identify which nucleotides in the nucleic acid population were modified cytosines. In one embodiment the method comprises comparing the sequence data of the nucleic acids in the first and second aliquot to identify which nucleotides in the nucleic acid population were modified cytosines. In another embodiment the adapters are hairpin adapters.

In another aspect provided herein is a method, comprising: physically fractionating DNA molecules from a human sample to generate two or more partitions; applying differential molecular tags and NGS-enabling adapters to each of the two or more partitions to generate molecular tagged partitions; assaying the molecular tagged partitions on an NGS instrument to generate sequence data for deconvoluting the sample into molecules that were differentially partitioned. In one embodiment the method further comprises analyzing the sequence data by deconvoluting the sample into molecules that were differentially partitioned. In another embodiment the DNA molecules are from extracted blood plasma. In another embodiment physical fractionating comprises fractionating molecules based on various degrees of methylation. In another embodiment various degrees of methylation comprise hypermethylation and hypomethylation. In another embodiment physically fractionating comprises fractionating with methyl-binding domain protein ("MBD")—beads to stratify into various degrees of methylation. In another embodiment the differential molecular tags are different sets of molecular tags corresponding to a MBD-partition. In another embodiment the physical fractionation comprises separating DNA molecules using immunoprecipitation. In another embodiment the method further comprises re-combining two or more molecular tagged fractions of the generated molecular tagged fractions. In another embodiment the method further comprises enriching the re-combined molecular tagged fractions or groups. In another embodiment the one or more characteristics is methylation. In another embodiment the fractionation comprises separating methylated nucleic acids from non-methylated nucleic acids using proteins comprising a methyl-binding domain to generate groups of nucleic acid molecules comprising varying degrees of methylation. In another embodiment one of the groups comprises hypermethylated DNA. In another embodiment at least one group is characterized by a degree of methylation. In another embodiment fractionation comprises isolating protein-bound nucleic acids. In another embodiment the isolating comprises immunoprecipitation.

In another aspect provided herein is a method for molecular tag identification of MBD-bead fractionated libraries through NGS, comprising: physical fractionation of an extracted DNA sample using a methyl-binding domain protein-bead purification kit, saving all elutions for downstream processing; parallel application of differential molecular tags and NGS-enabling adapter sequences to each fraction or group; re-combining all molecular tagged fractions or groups, and subsequent amplification using adapter-specific DNA primer sequences; (d) enrichment/hybridization of re-combined and amplified total library, targeting genomic regions of interest; re-amplification of the enriched total DNA library, appending a sample tag; and pooling different samples, and assaying them in multiplex on an NGS instrument; wherein NGS sequence data produced by the instrument provides sequence of the molecular tags being used to identify unique molecules, and sequence data for deconvolution of the sample into molecules that were differentially MBD-partitioned. In one embodiment the method comprises performing analysis of NGS data, with the molecular tags being used to identify unique molecules, as well deconvolution of the sample into molecules that were differentially MBD-partitioned. In another embodiment the fractionation comprises physical fractionation. In another embodiment the population of nucleic acid molecules is partitioned based on one or more characteristics selected from the group consisting of: methylation status, glycosylation status, histone modification, length and start/stop position. In another embodiment the method further comprises pooling the nucleic acid molecules. In another embodiment fractionation comprises fractionating based on a difference in a mono-nucleosomal profile. In another embodiment fractionation is capable of generating different mononucleosomal profiles for at least one group of nucleic acid molecules when compared to a normal. In another embodiment the method further comprises fractionating at least one group of nucleic acid molecules based on a different characteristic. In another embodiment analyzing comprises, at one or more loci, comparing a first characteristic corresponding to a first group of nucleic acid molecules to a second characteristic corresponding to a second group of nucleic acid molecules. In another embodiment the nucleic acid molecules are circulating tumor DNA. In another embodiment the nucleic acid molecules are cell-free DNA ("cfDNA"). In another embodiment the tags are used to distinguish different molecules in the same sample. In another embodiment the one or more characteristic is a cancer marker.

In another aspect provided herein is a method, comprising: providing a population of nucleic acid molecules obtained from a bodily sample of a subject; fractionating the population of nucleic acid molecules based on one or more characteristics to generate a plurality of groups of nucleic acid molecules, differentially tagging nucleic acid molecules in the plurality of groups to distinguish the nucleic acid molecules in each of the plurality of groups from one another based on the one or more characteristics; sequencing the plurality of groups of nucleic acid molecules to generate sequence reads; containing sufficient data to generate relative information about nucleosome positioning, nucleosome modification, or binding DNA-protein interaction for each of the plurality of groups of nucleic acid molecules. In one embodiment the method further comprises analyzing the sequence reads to generate relative information about nucleosome positioning, nucleosome modification, or binding DNA-protein interaction for each of the plurality of groups of nucleic acid molecules. In another embodiment the method further comprises using a trained classifier to classify the subject based on the one or more characteristics. In another embodiment the one or more characteristics comprise a quantitative characteristic of the mapped reads. In another embodiment the fractionation comprises physical fractionation. In another embodiment the method further comprises pooling the nucleic acid molecules. In another embodiment fractionation comprises fractionating based on a difference in a mono-nucleosomal profile. In another embodiment fractionation is capable of generating different mononucleosomal profiles for at least one group of nucleic acid molecules when compared to a normal. In another embodiment the method further comprises fractionating at least one group of nucleic acid molecules based on a different characteristic. In another embodiment analyzing comprises, at one or more loci, comparing a first characteristic corresponding to a first group of nucleic acid molecules to a second characteristic corresponding to a second group of nucleic acid molecules. In another embodiment analyzing comprises analyzing a characteristic of the one or more characteristics in a group relative to a normal sample at one or more loci. In another embodiment the one or more characteristics are selected from the group consisting of: a base-call frequency at a base position on the reference sequence, a number of molecules mapping to one base or sequence on the reference sequence, a number of molecules having a start site mapping to a base position on the reference sequence, and a number of molecules having a stop site mapping to a base position on the reference sequence, and a length of a molecule mapping to a locus on the reference sequence. In another embodiment the method further comprises using a trained classifier to classify the subject based on the one or more characteristics. In another embodiment the trained classifier classifies the one or more characteristics as associated with a tissue in the subject. In another embodiment the trained classifier classifies the one or more characteristics as associated with a type of cancer in the subject. In another embodiment the one or more characteristics are indicative of gene expression or status of a disease. In another embodiment the nucleic acid molecules are circulating tumor DNA. In another embodiment the nucleic acid molecules are cell-free DNA ("cfDNA"). In another embodiment the tags are used to distinguish different molecules in the same sample. In another embodiment the one or more characteristic is a cancer marker.

In another aspect provided herein is a method, comprising: providing a population of nucleic acid molecules obtained from a bodily sample of a subject; fractionating the population of nucleic acid molecules based on methylation status to generate a plurality of groups of nucleic acid molecules; differentially tagging nucleic acid molecules in the plurality of groups to distinguish the nucleic acid molecules in each of the plurality of groups from one another based on the one or more characteristics; sequencing the plurality of groups of nucleic acid molecules to generate sequence reads; and analyzing the sequence reads to detect one or more characteristics in one of the plurality of groups of nucleic acid molecules, wherein the one or more characteristics is indicative of nucleosome positioning, nucleosome modification, or a DNA-protein interaction. In another embodiment the method further comprises using a trained classifier to classify the subject based on the one or more characteristics. In another embodiment the one or more characteristics comprise a quantitative characteristic of the mapped reads. In another embodiment the fractionation comprises physical fractionation. In another embodiment the method further comprises pooling the nucleic acid molecules. In another embodiment fractionation comprises fractionating based on a difference in a mono-nucleosomal profile. In another embodiment fractionation is capable of generating different mononucleosomal profiles for at least one group of nucleic acid molecules when compared to a normal. In another embodiment the method further comprises fractionating at least one group of nucleic acid molecules based on a different characteristic. In another embodiment analyzing comprises, at one or more loci, comparing a first characteristic corresponding to a first group of nucleic acid molecules to a second characteristic corresponding to a second group of nucleic acid molecules. In another embodiment analyzing comprises analyzing a characteristic of the one or more characteristics in a group relative to a normal sample at one or more loci. In another embodiment the one or more characteristics are selected from the group consisting of: a base-call frequency at a base position on the reference sequence, a number of molecules mapping to one base or sequence on the reference sequence, a number of molecules having a start site mapping to a base position on the reference sequence, and a number of molecules having a stop site mapping to a base position on the reference sequence, and a length of a molecule mapping to a locus on the reference sequence. In another embodiment the method further comprises using a trained classifier to classify the subject based on the one or more characteristics. In another embodiment the trained classifier classifies the one or more characteristics as associated with a tissue in the subject. In another embodiment the trained classifier classifies the one or more characteristics as associated with a type of cancer in the subject. In another embodiment the one or more characteristics are indicative of gene expression or status of a disease. In another embodiment the nucleic acid molecules are circulating tumor DNA. In another embodiment the nucleic acid molecules are cell-free DNA ("cfDNA"). In another embodiment the tags are used to distinguish different molecules in the same sample. In another embodiment the one or more characteristic is a cancer marker.

In another aspect provided herein is a method, comprising: providing a population of nucleic acid molecules obtained from a bodily sample of a subject; fractionating the population of nucleic acid molecules to generate a plurality of groups of nucleic acid molecules comprising protein-bound cell-free nucleic acids; differentially tagging nucleic acid molecules in the plurality of groups to distinguish the nucleic acid molecules in each of the plurality of groups from one another based on the one or more characteristics; and sequencing the plurality of groups of nucleic acid molecules to generate sequence reads; wherein the sequence information obtained is sufficient for mapping the sequence reads to one or more loci on a reference sequence; and for analyzing the sequence reads to detect one or more characteristics in one of the plurality of groups of nucleic acid molecules, wherein the one or more characteristics is indicative of nucleosome positioning, nucleosome modification, or a DNA-protein interaction. In one embodiment the method further comprises mapping the sequence reads to one or more loci on a reference sequence; and analyzing the sequence reads to detect one or more characteristics in one of the plurality of groups of nucleic acid molecules, wherein the one or more characteristics is indicative of nucleosome positioning, nucleosome modification, or a DNA-protein interaction. In another embodiment the method further comprises using a trained classifier to classify the subject based on the one or more characteristics. In another embodiment the one or more characteristics comprise a quantitative characteristic of the mapped reads. In another embodiment the fractionation comprises physical fractionation. In another embodiment the population of nucleic acid molecules is partitioned based on one or more characteristics selected from the group consisting of: methylation status, glycosylation status, histone modification, length and start/stop position. In another embodiment the method further comprises pooling the nucleic acid molecules. In another embodiment the one or more characteristics is methylation. In another embodiment the fractionation comprises separating methylated nucleic acids from non-methylated nucleic acids using proteins comprising a methyl-binding domain to generate groups of nucleic acid molecules comprising varying degrees of methylation. In another embodiment one of the groups comprises hypermethylated DNA. In another embodiment at least one group is characterized by a degree of methylation. In another embodiment fractionation comprises separating single-stranded DNA molecules and/or double-stranded DNA molecules. In another embodiment the double-stranded DNA molecules are separated using hairpin adapters. In another embodiment fractionation comprises isolating protein-bound nucleic acids. In another embodiment fractionation comprises fractionating based on a difference in a mono-nucleosomal profile. In another embodiment fractionation is capable of generating different mononucleosomal profiles for at least one group of nucleic acid molecules when compared to a normal. In another embodiment the isolating comprises immunoprecipitation. In another embodiment the method further comprises fractionating at least one group of nucleic acid molecules based on a different characteristic. In another embodiment analyzing comprises, at one or more loci, comparing a first characteristic corresponding to a first group of nucleic acid molecules to a second characteristic corresponding to a second group of nucleic acid molecules. In another embodiment analyzing comprises analyzing a characteristic of the one or more characteristics in a group relative to a normal sample at one or more loci. In another embodiment the one or more characteristics are selected from the group consisting of: a base-call frequency at a base position on the reference sequence, a number of molecules mapping to one base or sequence on the reference sequence, a number of molecules having a start site mapping to a base position on the reference sequence, and a number of molecules having a stop site mapping to a base position on the reference sequence, and a length of a molecule mapping to a locus on the reference sequence. In another embodiment the method further comprises using a trained classifier to classify the subject based on the one or more characteristics. In another embodiment the trained classifier classifies the one or more characteristics as associated with a tissue in the subject. In another embodiment the trained classifier classifies the one or more characteristics as associated with a type of cancer in the subject. In another embodiment the one or more characteristics are indicative of gene expression or status of a disease. In another embodiment the nucleic acid molecules are circulating tumor DNA. In another embodiment the nucleic acid molecules are cell-free DNA ("cfDNA"). In another embodiment the tags are used to distinguish different molecules in the same sample.

In another aspect provided herein is a method, comprising: providing a population of nucleic acid molecules obtained from a bodily sample of a subject; fractionating the population of nucleic acid molecules based on one or more characteristics to generate a plurality of groups of nucleic acid molecules; differentially tagging nucleic acid molecules in the plurality of groups to distinguish the nucleic acid molecules in each of the plurality of groups from one another based on the one or more characteristics; sequencing the plurality of groups of nucleic acid molecules to generate sequence reads; wherein the sequence information obtained is sufficient for mapping the sequence reads to one or more loci on a reference sequence; and analyzing the sequences reads to detect one or more characteristics in one of the plurality of groups of nucleic acid molecules, wherein the one or more characteristics are not capable of detection in a pool of sequence reads from the plurality of groups. In one embodiment the method further comprises mapping the sequence reads to one or more loci on a reference sequence; and analyzing the sequence reads to detect one or more characteristics in one of the plurality of groups of nucleic acid molecules, wherein the one or more characteristics are not capable of detection in a pool of sequence reads from the plurality of groups. In another embodiment the fractionation comprises physical fractionation.

In another aspect provided herein is a method, comprising: providing a population of nucleic acid molecules obtained from a bodily sample of a subject; fractionating the population of nucleic acid molecules based on one or more characteristics to generate plurality of groups of nucleic acid molecules, wherein the nucleic acid molecules of each of the plurality of groups comprise distinct identifiers; pooling the plurality of groups of nucleic acid molecules; sequencing the pooled plurality of groups of nucleic acid molecules to generate plurality of sets sequence reads; and fractionating the sequence reads based on the identifiers.

In another aspect provided herein is a composition, comprising a pool of nucleic acid molecules comprising differently tagged nucleic acid molecules, wherein the pool comprises a plurality of sets of nucleic acid molecules that are differently tagged based on one or more characteristics selected from the group consisting of: selected from the group consisting of: methylation status, glycosylation status, histone modification, length and start/stop position, wherein the pool is derived from a biological sample. In one embodiment the plurality of sets is any of 2, 3, 4, 5 or more than 5.

In another aspect provided herein is a method, comprising: fractionating a population of nucleic acid molecules into a plurality of groups, the plurality of groups comprising nucleic acids differing by a characteristic; tagging the nucleic acids in each of the plurality of groups with a set of tags that distinguish the nucleic acids in each of the plurality of groups to produce a population of tagged nucleic acids, wherein each of the tagged nucleic acids comprises one or more tags; sequencing the population of tagged nucleic acids to generate sequence reads; using the one or more tags to group each group of sequence reads; and analyzing the sequence reads to detect a signal in at least one of the groups relative to a normal sample or a classifier. In one embodiment the method further comprises normalizing the signal in at least one of the groups against another group or a whole genome sequence.

In another aspect provided herein is a method comprising: providing a population of cell-free DNA from a biological sample; fractionating the population of cell-free DNA based on a characteristic that is present at different levels in cell-free DNA derived from cancerous compared to non-cancerous cells, thereby generating subpopulations of cell-free DNA; amplifying at least one of the subpopulations of cell-free DNA; and, sequencing at least one of the amplified subpopulations of cell-free DNA. In one embodiment the characteristic is: the methylation level of the cell-free DNA; the glycosylation level of the cell-free DNA; the length of the cell-free DNA fragments; or the presence of single-stranded breaks in the cell-free DNA.

In another aspect provided herein is a method comprising: providing a population of cell-free DNA from a biological sample; fractionating the population of cell-free DNA based on the methylation level of the cell-free DNA, thereby generating subpopulations of cell-free DNA; amplifying at least one of the subpopulations of cell-free DNA; and, sequencing at least one of the amplified subpopulations of cell-free DNA.

In another aspect provided herein is a method for determining the methylation status of cell-free DNA comprising: providing a population of cell-free DNA from a biological sample; fractionating the population of cell-free DNA based on the methylation level of the cell-free DNA, thereby generating subpopulations of cell-free DNA; sequencing at least one subpopulation of cell-free DNA, thereby generating sequence reads; and, assigning a methylation status to each cell free DNA depending on the subpopulation the corresponding sequence reads occurs in.

In another aspect provided herein is a method of classifying a subject wherein the method comprises: providing a population of cell-free DNA from a biological sample from the subject; fractionating the population of cell-free DNA based on the methylation level of the cell-free DNA, thereby generating subpopulations of cell-free DNA; sequencing the subpopulations of cell-free DNA, thereby generating sequence reads; and, using a trained classifier to classify the subject depending on which sequence reads occur in which subpopulation. In another embodiment the population of cell-free DNA is fractionated by one or more characteristics that provide a difference in signal between healthy and diseased states. In another embodiment the population of cell-free DNA is fractionated based on the methylation level of the cell-free DNA. In another embodiment determining the fragmentation pattern of the cell-free DNA further comprises analyzing the number of sequence reads mapping to each base position in the reference genome. In another embodiment the method further comprises determining the fragmentation pattern of the cell-free DNA in each subpopulation by analyzing the number of sequence reads mapping to each base position in the reference genome.

In another aspect provided herein is a method for analyzing the fragmentation pattern of cell-free DNA comprising: providing a population of cell-free DNA from a biological sample; fractionating the population of cell-free DNA, thereby generating subpopulations of cell-free DNA; sequencing at least one subpopulation of cell-free DNA, thereby generating sequence reads; aligning the sequence reads to a reference genome; and, determining the fragmentation pattern of the cell-free DNA in each subpopulation by analysing any number of the: length of each sequence read mapping to each base position in the reference genome; number of sequence reads mapping to the base position in the reference genome as a function of length of the sequence reads; number of sequence reads starting at each base position in the reference genome; or, number of sequence reads ending at each base position in the reference genome. In another embodiment the one or more characteristics comprise a chemical modification selected from the group consisting of: methylation, hydroxymethylation, formylation, acetylation, and glycosylation.

Any of the methods described herein wherein a ratio of DNA:bead is 1:100.

Any of the methods described herein wherein a ratio of DNA:bead is 1:50

Any of the methods described herein wherein a ratio of DNA:bead is 1:20

In one aspect provided herein is the use of physical fractionation based on degree of DNA methylation during analysis of circulating tumor DNA (ctDNA) to determine gene expression or disease state.

In one aspect provided herein is the use of a characteristic that provides a difference in signal between a normal and diseased state to physically partition ctDNA during analysis of ctDNA.

In one aspect provided herein is the use of a characteristic that provides a difference in signal between a normal and diseased state to physically partition ctDNA.

In one aspect provided herein is the use of a characteristic that provides a difference in signal between a normal and diseased state to physically partition ctDNA prior to sequencing and optional downstream analysis.

In one aspect provided herein is the use of a characteristic that provides a difference in signal between a normal and diseased state to physically partition ctDNA for differential labelling/tagging. In one embodiment the differential fragmentation pattern is indicative of gene expression or disease state. In another embodiment the differential fragmentation pattern is characterized by one or more differences relative to a normal selected from the group consisting of: length of each sequence read mapping to each base position in the reference genome; number of sequence reads mapping to the base position in the reference genome as a function of length of the sequence reads; number of sequence reads starting at each base position in the reference genome; and number of sequence reads ending at each base position in the reference genome In one aspect provided herein is the use of fractionation based on a differential fragmentation pattern during analysis of ctDNA. In one embodiment the differential fragmentation pattern is indicative of gene expression or disease state. In another embodiment the differential fragmentation pattern is characterized by one or more differences relative to a normal selected from the group consisting of: length of each sequence read mapping to each base position in the reference genome; number of sequence reads mapping to the base position in the reference genome as a function of length of the sequence reads; number of sequence reads starting at each base position in the reference genome; and number of sequence reads ending at each base position in the reference genome In one aspect provided herein is the use of a differential fragmentation pattern to partition ctDNA. In one embodiment the differential fragmentation pattern is indicative of gene expression or disease state. In another embodiment the differential fragmentation pattern is characterized by one or more differences relative to a normal selected from the group consisting of: length of each sequence read mapping to each base position in the reference genome; number of sequence reads mapping to the base position in the reference genome as a function of length of the sequence reads; number of sequence reads starting at each base position in the reference genome; and number of sequence reads ending at each base position in the reference genome In one aspect provided herein is the use of a differential fragmentation pattern to partition ctDNA prior to sequencing and optional downstream analysis. In one embodiment the differential fragmentation pattern is indicative of gene expression or disease state. In another embodiment the differential fragmentation pattern is characterized by one or more differences relative to a normal selected from the group consisting of: length of each sequence read mapping to each base position in the reference genome; number of sequence reads mapping to the base position in the reference genome as a function of length of the sequence reads; number of sequence reads starting at each base position in the reference genome; and number of sequence reads ending at each base position in the reference genome In one aspect provided herein is the use of a differential fragmentation pattern to partition ctDNA for differential labelling/tagging.

In one aspect provided herein is the use of differential molecular tagging of DNA molecules partitioned by molecular binding domain (MBD)—beads to stratify into various degrees of DNA methylation, which are then quantified by next generation sequencing (NGS).

In one aspect provided herein is a method of analyzing a nucleic acid population comprising at least two forms of nucleic acid selected from double-stranded DNA, single-stranded DNA and single-stranded RNA, the method, wherein each of the at least two forms comprises a plurality of molecules, comprising: linking at least one of the forms of nucleic acid with at least one tag nucleic acid to distinguish the forms from one another; amplifying the forms of nucleic acid, at least one of which is linked to at least one nucleic acid tag, wherein the nucleic acids and linked nucleic acid tag, are amplified, to produce amplified nucleic acids, of which those amplified from the at least one form are tagged; and, sequencing a plurality of the amplified nucleic acid that have been linked to tags, wherein the sequence data is sufficient to be decoded to real the forms of the nucleic acids in the population prior to linking to the at least one tag. In one embodiment the molecular tag comprises one or a plurality of nucleic acid barcodes. In another embodiment the pool of tagged nucleic acid molecules a combination of any two barcodes in a set have different combined sequences than a combination of any two barcodes in any other set.

In another aspect provided herein is a pool of tagged nucleic acid molecules, each nucleic acid molecule in the pool comprising a molecular tag selected from one of a plurality of tag sets, each tag set comprising a plurality of different tags, wherein the tags in any one set are distinct from the tags in any other set, and wherein each tag set contains information (i) indicating a characteristic of the molecule to which it is attached or of the parent molecule from which the molecule is derived and (ii) which, alone or in combination with information from the molecule to which it is attached, uniquely distinguishes the molecule to which it is attached from other molecules tagged with tags from the same tag set. In one embodiment the molecular tag comprises two nucleic acid barcodes, attached at opposite ends of the molecule. In another embodiment the barcodes are between 10 and 30 nucleotides in length.

In another aspect provided herein is a system comprising: a nucleic acid sequencer; a digital processing device comprising at least one processor, an operating system configured to perform executable instructions, and a memory; and, a data link communicatively connecting the nucleic acid sequencer and the digital processing device; wherein the digital processing device further comprises instructions executable to create an application for analyzing a nucleic acid population comprising at least two forms of nucleic acid selected from: double-stranded DNA, single-stranded DNA and single-stranded RNA, each of the at least two forms comprising a plurality of molecules, the application comprising: a software module receiving sequence data from the nucleic acid sequencer via the data link, the sequence data of amplified nucleic acids at least some of which are tagged, the sequence data generated by linking at least one of the forms of nucleic acid with at least one tagged nucleic acid to distinguish the forms from one another, amplifying the forms of nucleic acid at least one of which is linked to at least one nucleic acid tag, wherein the nucleic acids and linked nucleic acid tags are amplified to produce amplified nucleic acids of which those amplified from the at least one form are tagged; and, a software module assaying the sequence data of the amplified nucleic acids by obtaining sequence information sufficient to decode the tagged nucleic acid molecules of the amplified nucleic acids to reveal the forms of nucleic acids in the population providing an original template for the amplified nucleic acids linked to the tag nucleic acid molecules for which sequence data has been assayed. In one embodiment the application further comprises a software module decoding the tagged nucleic acid molecules of the amplified nucleic acids to reveal the forms of nucleic acids in the population providing an original template for the amplified nucleic acids linked to the tag nucleic acid molecules for which sequence data has been assayed. In another embodiment the application further comprises a software module transmitting a result of the assay via a communications network.

In another aspect provided herein is a system comprising: a next-generation sequencing (NGS) instrument; a digital processing device comprising at least one processor, an operating system configured to perform executable instructions, and a memory; and, a data link communicatively connecting the NGS instrument and the digital processing device; wherein the digital processing device further comprises instructions executable to create an application comprising: a software module for receiving sequence data from the NGS instrument via the data link, the sequence data generated by physically fractionating DNA molecules from a human sample to generate two or more partitions, applying differential molecular tags and NGS-enabling adapters to each of the two or more partitions to generate molecular tagged partitions, and assaying the molecular tagged partitions with the NGS instrument; a software module for generating sequence data for deconvoluting the sample into molecules that were differentially partitioned; and, a software module for analyzing the sequence data by deconvoluting the sample into molecules that were differentially partitioned. In one embodiment the application further comprises a software module transmitting a result of the assay via a communications network.

In another aspect provided herein is a system comprising: a next-generation sequencing (NGS) instrument; a digital processing device comprising at least one processor, an operating system configured to perform executable instructions, and a memory; and, a data link communicatively connecting the NGS instrument and the digital processing device; wherein the digital processing device further comprises instructions executable by the at least one processor to create an application for molecular tag identification of MBD-bead fractionated libraries comprising: a software module configured to receive sequence data from the NGS instrument via the data link, the sequence data generated by physically fractionating an extracted DNA sample using a methyl-binding domain protein-bead purification kit, saving all elutions for downstream processing; conducing parallel application of differential molecular tags and NGS-enabling adapter sequences to each fraction or group; re-combining all molecular tagged fractions or groups, and subsequent amplification using adapter-specific DNA primer sequences; conducting enrichment/hybridization of re-combined and amplified total library, targeting genomic regions of interest; re-amplifying the enriched total DNA library, appending a sample tag; pooling different samples; and assaying them in multiplex on the NGS instrument; wherein NGS sequence data produced by the instrument provides sequence of the molecular tags being used to identify unique molecules, and sequence data for deconvolution of the sample into molecules that were differentially MBD-partitioned; and, a software module configured to perform analysis of the sequence data by using the molecular tags to identify unique molecules and deconvoluting the sample into molecules that were differentially MBD-partitioned. In one embodiment the application further comprises a software module configured to transmit a result of the analysis via a communications network.

The summary provided of above is an exemplary list of embodiments and is not intended to be a complete list of embodiments.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

FIG. 12A, FIG. 12B, and FIG. 12C show methylation profiling using whole genome sequencing. FIG. 12A shows position along a 600 bp region in the transcription start site (TSS) on the X-axis and frequency of hypermethylation sites along the Y-axis. FIG. 12B shows position along a 600 bp region in the transcription start site (TSS) on the X-axis and frequency of hypomethylation sites along the Y-axis. FIG. 12C shows percentage hypermethylation on X-axis and fragment length on Y-axis.

FIG. 13A shows genomic position of MOB3A gene on X-axis and fragment length for nucleic acid molecules from different fractionated groups is indicated by separate rows. The fractionated groups included hypermethylated, hypomethylated, hypermethylated mixed with hypomethylated (hyper+hypo) and an unfractionated group (no MBD) for comparison.

FIG. 14A shows a heat map with coverage from unfractionated group (no MBD) and from mixing partitions after fractionating respectively on X-axis and Y-axis.

FIG. 18A shows genomic position of AP3D1 gene on X-axis and coverage of reads for nucleic acid molecules from different groups indicated by separate rows. The groups include fractionated groups, such as hypermethylated, hypomethylated, and of unfractionated group (no MBD) for comparison. TSS is shown as vertical line in the middle of heat maps with an arrow indicating direction of transcription. FIG. 18B shows percentage hypermethylation on X-axis and fragment length on the Y-axis. For example, in FIG. 18B, the percentage methylation in a non-fractionated nucleic acid sample can be about 65%, as indicated by red dotted line.

FIG. 19A shows genomic position of DNMT1 gene on X-axis and coverage of reads for nucleic acid molecules from different groups is indicated by separate rows. The groups included fractionated groups, such as hypermethylated, hypomethylated, and of unfractionated group (no MBD) for comparison. TSS is shown as vertical line in the middle of heat maps with an arrow indicating direction of transcription. FIG. 19B shows percentage hypermethylation on X-axis and fragment length on Y-axis.

DETAILED DESCRIPTION

Figure 1:
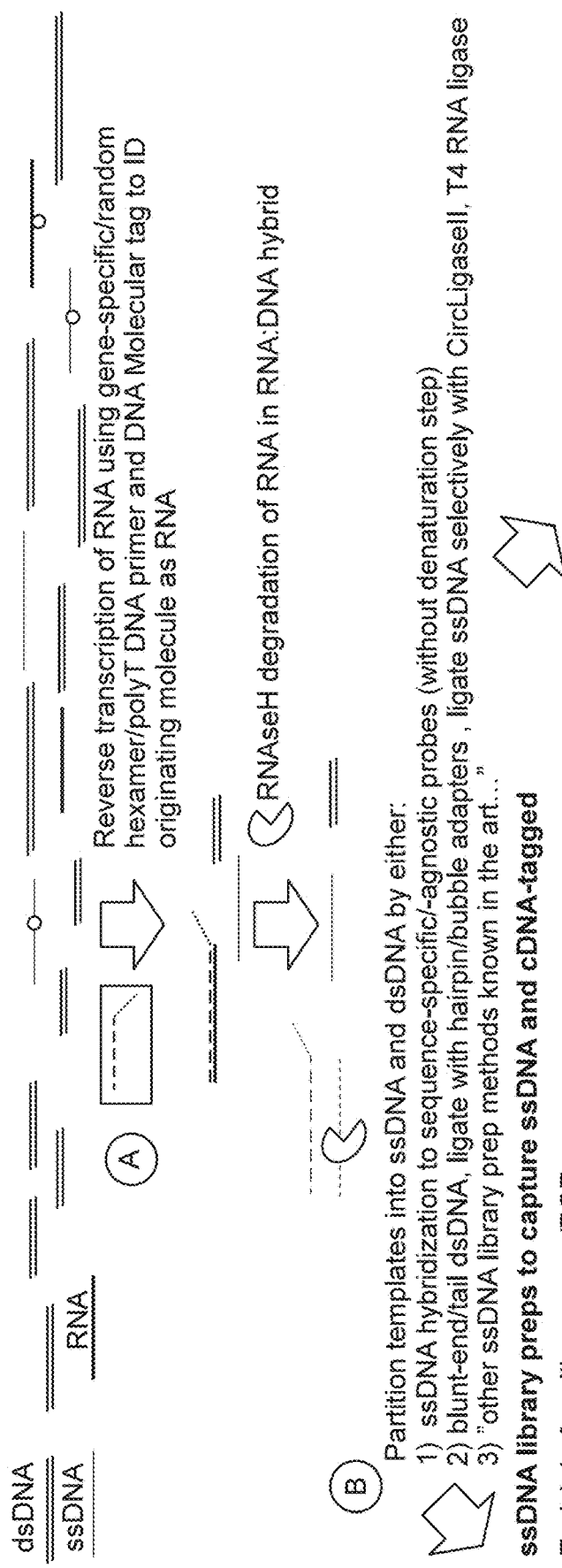
FIG. 1 shows an exemplary scheme for partitioning RNA, single-stranded DNA and double-stranded DNA.
Figure 1:
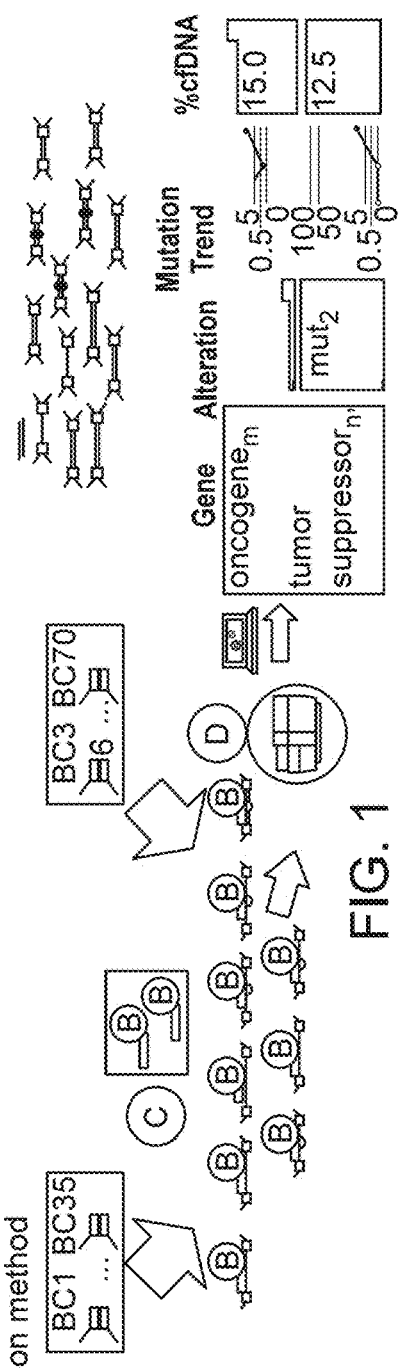

The term "Cell Free DNA" and "Cell Free DNA Population" as used herein refer to DNA that was originally found in a cell or cells in a large complex biological organism, e.g., a mammal, and was released from the cell into a liquid fluid found in the organism, e.g., blood plasma, lymph, cerebrospinal fluid, urine, wherein the DNA may be obtained by obtaining a sample of the fluid without the need to perform an in vitro cell lysis step.

General

The present disclosure provides numerous methods, reagents, compositions, and systems for analyzing complex genomic material while reducing or eliminating loss of molecular characteristic (e.g., epigenetic or other types of structural) information that is initially present in the complex genomic material. In some embodiments, molecular tags can be used to track different forms of nucleic acids and enumerate such different forms for the purpose of determining genetic modifications (e.g., SNVs, indels, gene fusions and copy number variations). In some embodiments, the methods described herein are used to detect, analyze or monitor a condition such as cancer in a subject or status of a fetus. In some embodiments, the subject is not pregnant.

The disclosure provides methods for processing nucleic acid populations containing different forms. As used herein, different forms of nucleic acids possess different characteristics. For example, and without limitation, RNA and DNA are forms that differ based on sugar identity. Single-stranded (ss) and double-stranded (ds) nucleic acids differ on number of strands. Nucleic acids molecules can differ based on epigenetic characteristics such as 5-methylcytosine or association with proteins such as histones. Nucleic acids can possess different nucleotide sequences, e.g., specific genes or genetic loci. Characteristics can differ in terms of degree. For example, DNA molecules can differ in their extent of epigenetic modification. Extent of modification can refer to a number of modifying events to which a molecule has been subject, such as number of methylation groups (extent of methylation) or other epigenetic changes. For example, methylated DNA may be hypomethylated or hypermethylated. Forms can be characterized by combinations of characteristics, for example, single stranded-unmethylated or double stranded-methylated. Fractionation of molecules based on one or a combination of characteristics can be useful for multi-dimensional analysis of single molecules. These methods accommodate multiple forms and/or modifications of nucleic acid in a sample, such that sequence information can be obtained for multiple forms. The methods also preserve the identity of the initial multiple forms or modified states through processing and analysis, such that analysis of nucleic base sequences can be combined with epigenetic analysis. Some methods involve separation, tagging and subsequent pooling of different forms or modification states reducing the number of processing steps required to analyze multiple forms present in a sample. Analyzing multiple forms of nucleic acid in samples provides greater information in part because there are more molecules to analyze (which can be significant when very low total amounts of nucleic acid are available) but also because the different forms or modification states can provide different information (for example, a mutation may be present only in RNA), and because different types of information (e.g. genetic and epigenetic) can be correlated with one another, thereby producing greater accuracy, certainty, or resulting in the discovery of new correlations with a medical condition.

The CpG dinucleotide is underpresented in the normal human genome, with the majority of CpG dinucleotide sequences being transcriptionally inert (e.g. DNA heterochromatic regions in pericentromeric parts of the chromosome and in repeat elements) and methylated. However, many CpG islands are protected from such methylation especially around transcription start sites (TSS).

Cancer can be indicated by epigenetic variations, such as methylation. Examples of methylation changes in cancer include local gains of DNA methylation in the CpG islands at the transcription start site (TSS) of genes involved in normal growth control, DNA repair, cell cycle regulation, and/or cell differentiation. This hypermethylation can be associated with an aberrant loss of transcriptional capacity of involved genes and occurs at least as frequently as point mutations and deletions as a cause of altered gene expression. DNA methylation profiling can be used to detect regions with different extents of methylation ("differentially methylated regions" or "DMRs") of the genome that are altered during development or that are perturbed by disease, for example, cancer or any cancer-associated disease. The genome of cancer cells harbor imbalance in the above DNA methylation patterns, and therefore in functional packaging of the DNA. The abnormalities of chromatin organization are therefore coupled with methylation changes and may contribute to enhanced cancer profiling when analyzed jointly. Combining MBD-partitioning with fragmentomic data, such as fragment mapped starts and stops positions (correlated with nucleosome positions), fragment length and associated nucleosome occupancy, can be used for chromatin structure analysis in hypermethylation studies with the aim to improve biomarker detection rate.

Methylation profiling can involve determining methylation patterns across different regions of the genome. For example, after partitioning molecules based on extent of methylation (e.g., relative number of methylated sites per molecule) and sequencing, the sequences of molecules in the different partitions can be mapped to a reference genome. This can show regions of the genome that, compared with other regions, are more highly methylated or are less highly methylated. In this way, genomic regions, in contrast to individual molecules, may differ in their extent of methylation.

A characteristic of nucleic acid molecules may be a modification, which may include various chemical or protein modifications (i.e. epigenetic modifications). Non-limiting examples of chemical modification may include, but are not limited to, covalent DNA modifications, including DNA methylation. In some embodiments, DNA methylation comprises addition of a methyl group to a cytosine at a CpG site (a cytosine followed by a guanine in a nucleic acid sequence). In some embodiments, DNA methylation comprises addition of a methyl group to adenine, such as in $N^6$-methyladenine. In some embodiments, DNA methylation is 5-methylation (modification of the 5th carbon of the 6 carbon ring of cytosine). In some embodiments, 5-methylation comprises addition of a methyl group to the 5C position of the cytosine to create 5-methylcytosine (m5c). In some embodiments, methylation comprises a derivative of m5c. Derivatives of m5c include, but are not limited to, 5-hydroxymethylcytosine (5-hmC), 5-formylcytosine (5-fC), and 5-carboxylcytosine (5-caC). In some embodiments, DNA methylation is 3C methylation (modification of the 3rd carbon of the 6 carbon ring of cytosine). In some embodiments, 3C methylation comprises addition of a methyl group to the 3C position of the cytosine to generate 3-methylcytosine (3 mC). Methylation can also occur at non CpG sites, for example, methylation can occur at a CpA, CpT, or CpC site. DNA methylation can change the activity of methylated DNA region. For example, when DNA in a promoter region is methylated, transcription of the gene may be repressed. DNA methylation is critical for normal development and abnormality in methylation may disrupt epigenetic regulation. The disruption, e.g., repression, in epigenetic regulation may cause diseases, such as cancer. Promoter methylation in DNA may be indicative of cancer.

Protein modifications include binding to components of chromatin, particularly histones including modified forms thereof, and binding to other proteins, such as proteins involved in replication or transcription. The disclosure provides methods of processing and analyzing nucleic acids with different extents of modification, such that the nature of their original modification is correlated with a nucleic acid tag and can be decoded by sequencing the tag when nucleic acids are analyzed. Genetic variation of sample nucleic acid modifications can then be associated with the extent of modification (epigenetic variation) of that nucleic acid in the original sample.

As used herein, the terms "fractionating" and "partitioning" refer to separating molecules based on different characteristics. Nucleic acid molecules in a sample may be fractionated based on one or more characteristics. Fractionation may include physically partitioning nucleic acid molecules into subsets or groups based on the presence or absence of a genomic characteristic. Fractionation may include physically partitioning nucleic acid molecules into partition groups based on the degree to which a genomic characteristic is present. A sample may be fractionated or partitioned into one or more groups partitions based on a characteristic that is indicative of differential gene expression or a disease state. A sample may be fractionated based on a characteristic, or combination thereof that provides a difference in signal between a normal and diseased state during analysis of nucleic acids, e.g., cell free DNA ("cfDNA"), non-cfDNA, tumor DNA, circulating tumor DNA ("ctDNA") and cell free nucleic acids ("cfDNA").

The present disclosure provides methods and systems for efficiently analyzing nucleic acid molecules. The methods may include fractionating the nucleic acid molecules into different partitions based on one or a plurality of characteristics, followed by sequencing (alone or together) and analyzing the nucleic acid molecules in each partition. In some cases, the partitions of nucleic acid molecules are amplified prior to and/or after sequencing. The methods can be used in various applications, such as prognosis, diagnosis and/or for monitoring of a disease.

Nucleic acid molecules may be characterized by any of one or more characteristics. A characteristic of the nucleic acid molecules may include strandedness, protein bound regions, nucleic acid length, start/stop position, chemical modifications, or protein modifications. The strandedness of nucleic acid molecules may include single stranded (e.g., ssDNA or RNA) or double stranded molecules (e.g., dsDNA).

A genomic characteristic of nucleic acid molecules may be a modification, which may include various chemical modifications. As non-limiting examples, a chemical modification may include covalent DNA modification, such as DNA methylation (5 mC), hydroxymethylation (5 hmC), formylmethylation (5fC), carboxymethylation (5CaC), $N^6$-methyladenine or glycosylation. DNA methylation includes addition of methyl groups to DNA (e.g. CpG) and can change the expression of methylated DNA region. For example, when DNA in a promoter region is methylated, transcription of the gene may be repressed. DNA methylation is critical for normal development and abnormality in methylation may disrupt epigenetic regulation. The disruption, e.g., repression, in epigenetic regulation may cause diseases, such as cancer. Promoter methylation in DNA may be indicative of cancer.

As a non-limiting example, benefits of methods involving partitioning single-stranded RNA and/or DNA as well as double-stranded DNA to characterize a sample include:
1. Additional support for SNV, CNV, and indel calls from ssDNA and RNA molecules in addition to dsDNA;
2. The easier identification (targeting) of gene fusions in RNA as compared to DNA because variable breakpoints in intronic DNA yields defined exon-exon junctions in RNA;
3. The identification or differential expression levels of messenger RNA (mRNA), microRNA (miRNA), and long noncoding RNA (lncRNA) can be characteristic of many disease states. Confirmation and additional support of expression signatures found in nucleosomal positioning changes within circulating tumor DNA (ctDNA) populations compared to healthy cell free DNA (cfDNA) from leukocytes that could be important in the early detection of cancer Additionally, leukocyte-derived cfDNA and cfRNA expression changes can also be indicative of immune response to disease.
4. Evidence of unstable molecules. Capture of shorter, circulating tumor DNA (ctDNA)—studies of cell-free DNA have found that the length of tumor DNA (ctDNA) can be significantly shorter than normal DNA. Some evidence indicates that these shorter sequences are unstable and can be present as ssDNA. These could also provide information on transcription factor binding changes in ctDNA compared to cfDNA that could be important in early detection of cancer. Similarly, cfDNA can also be indicative of disease response; and
5. Capture of damaged/degraded DNA that may be clinically relevant and that contains single-stranded "gapped" regions.

Analyzing multiple forms of nucleic acids in a sample can occur by, e.g., differentially tagging different forms of nucleic acids and/or partitioning different forms of nucleic acids prior to sequencing.

II. Differential Tagging Different Nucleic Acid Forms in a Sample

Samples of nucleic acids, such as cell-free nucleic acids in bodily fluids, often contain nucleic acids in multiple forms, including single- and double-stranded DNA and single-stranded RNA. Because the total amount of nucleic acids in such samples can be low and because the different forms of nucleic acids having different characteristics and/or modifications may yield different information regarding the sample, provided herein are methods of analyzing 2, 3 or all such forms.

Preparation and analysis of multiple forms is more efficient if at least some of the steps can be performed in parallel. The information determined from such samples is most informative if sequence information of a particular nucleic acid after processing can be correlated with the original form of the nucleic acid in the sample. For example, if a SNV is determined in a particular nucleic acid after processing, it can be determined whether that nucleic acid was derived from RNA, single-stranded DNA or double-stranded DNA in the original sample.

Identification of the different forms of nucleic acid in a sample can be achieved by differential tagging of the different forms of nucleic acid in the sample before the forms have been altered in a way that obfuscates their original form, such as by second-strand synthesis or amplification. Thus, in a nucleic acid including multiple forms, at least one form is linked to a nucleic acid tag to distinguish it from one or more other forms present in the sample. In a sample containing three forms of nucleic acid, such as single-stranded DNA, single-stranded RNA and double-stranded DNA, the three forms can be distinguished by differentially labelling at least two of the forms or by differentially labelling all three. The tags linked to nucleic acid molecules of the same form can be the same or different from one another. But if different from one another, the tags may, in some embodiments, have part of their code in common so as to identify the molecules to which they are attached as being of a particular form. For example, nucleic molecules of a particular form can bear codes of the form A1, A2, A3, A4 and so forth, and those of a different form B1, B2, B3, B4 and so forth. Such a coding system allows distinction both between the forms and molecules within a form. Exemplary strategies for differentially tagging nucleic acid molecules having different characteristics, e.g., degree of methylation as determined using methyl-binding domain proteins, are provided in FIG. 24 (described below).

After differential labelling of one, some or all forms of nucleic acid in a sample with nucleic acid tags, the forms can be amplified such that the nucleic acid tags are amplified together with the forms in the original sample. The amplified nucleic acids can then be subjected to sequence analysis to read part or all of the sequence of the nucleic acids originally in the samples as well as that of the linked nucleic acid tags. The sequences of the tags can then be decoded to indicate the form of a nucleic acid in the original sample. Sequences of different forms can then be compared to see if a genetic variation is found predominantly or exclusively only in certain form(s) of nucleic acid or occurs with about the same frequency independently of the original form. Some or all of the steps after differential tagging of different forms, particularly amplification and sequencing, can be performed with nucleic acids of the different forms pooled. Such methods preferably result in amplification and sequencing of at least 40, 50, 60, 70, 80, 90 or 95% of nucleic acid molecules of two, three or more forms present in a sample.

Double-stranded nucleic acids can be differentially labelled by ligation to at least partially double stranded adapters. Typically, the double-stranded nucleic acids are ligated to such adapters at both ends. Either or both of such adapters can include a nucleic acid tag. If two adapters each having a tag are linked to the respective ends of a nucleic acid, the tag combination can function as an identifier. Single-stranded DNA or RNA molecules do not ligate to a significant extent to double-stranded ends of adapters and so do not receive a nucleic acid tag. The double-stranded adapters can be fully double-stranded or partially double-stranded as is the case for Y-shaped adapters or hairpin adapters. Exemplary sequences for Y-shaped adapters are shown below.

Universal Adapter

Universal adapter

SEQ ID No. 1:
(SEQ ID NO: 1)
5'AATGATACGGCGACCACCGAGATCTACACTCTTTCCCTACACGACGCT

CTTCCGATCT-3'

Adapter Tag

SEQ ID No. 2:
(SEQ ID NO: 2)
5'GATCGGAAGAGCACACGTCTGAACTCCAGTCACNNNNNNATCTCGTAT

GCCGTCTTCTGCTTG-3'

A truncated version of these adapter sequences has been described by Rohland et al., Genome Res. 2012 May; 22(5): 939-946.

Because Y-shaped adapters have single-stranded ends, they may need to be avoided (e.g., by separating single-stranded DNA with a probe that does not bind the Y-shaped adapters) or protected if a subsequent step is to be performed of separating single-stranded sample nucleic acids from other sample nucleic acids.

RNA molecules can be differentially labelled with a nucleic acid tag by virtue of their being the only form of molecule in a sample on which a reverse transcriptase with RNA-dependent DNA polymerase can act. The nucleic acid tag can be introduced as a 5' tag of a primer used to prime reverse transcription. Reverse transcription can be random or sequence-specific. Following reverse transcription, the original RNA strand can be degraded followed by synthesis of a second complementary DNA strand. The now double-stranded DNA can be blunt-ended, if necessary, and joined to adapters in similar fashion to double-stranded DNA molecules already present in the sample. Alternatively, RNA/DNA hybrid molecules can be directly joined to adapters.

Single-stranded DNA molecules can be fractionated from double-stranded DNA molecules by treatment with an intramolecular ligase. In some embodiments, the intramolecular ligase is CircLigase™ ssDNA Ligase for differentially tagging ssDNA with a 3' tag. ssDNA is dephosphorylated at 5' end prior to treating with the intramolecular ligase to prevent circularization of ssDNA. In one instance, the ligase used to attach tags to single-stranded DNA is CircLigase™ ssDNA Ligase. CircLigase™ ssDNA Ligase is a thermostable ATP-dependent ligase. Second-strand synthesis can occur by several mechanisms including linking single-stranded DNA at one end to an oligonucleotide (e.g., with T4 RNA ligase) to provide a primer binding site, hybridizing single-stranded DNA to complementary oligonucleotides which serve as primers to extend based on the template sequence they are hybridized to, or hybridization to random oligonucleotides, which likewise serve as primers for extension based on the template sequence they are hybridized to. One method uses a single-stranded ligase to append an oligonucleotide with an extendible 3' end onto single-stranded DNA library members (see Gansauge & Meyer, Nature Protocols 8, 737 (2013)). The second DNA strand is filled in using the adapter as a primer binding site. A 5'DNA phosphorylation step and standard (dsDNA) ligation is then performed to add an adapter to the 5' end of the library molecules.

In another method, steps from the commercially available NEBDirect methodology may be included in the method, single-stranded DNA molecules are hybridized to a sequence-specific primer for second strand synthesis followed by end repair, and ligation to flanking adapters (see neb.com/nebnext-direct/nebnext-direct-for-target-enrichment). The second DNA strand containing the primer is degraded so it is not sequenced. Another method uses random primers having adapter sequences on their 5' ends and random bases on the 3' end. There are usually 6 random bases, but can be between 4 and 9 bases long. This approach is particularly amenable for low input/single cell amplification for RNA-seq or Bisulfite-Sequencing (Smallwood et al., Nat. Methods 2014 August; 11(8):817-820).

ssDNA can be selectively captured by nucleic acid (NA) probes, by omission of standard denaturation step prior to hybridization. The ssDNA-probes hybrids can be isolated from the cfNA (cell free nucleic acids) population by conventional methods (e.g., biotinylated DNA/RNA probes, captured by streptavidin-bead magnets). The probe sequences can be target-specific and the same as a panel with a dsDNA workflow, a subset of that workflow, or different (e.g., targeting RNA-fusions at exon-exon junctions, 'hot spot' DNA sequences). All single-stranded nucleic acid (ssNA) can be captured in this step, in a sequence-agnostic manner by utilizing probes with 'universal nucleotide bases', such as deoxyinosine, 3-nitropyrrole, and 5-nitroindole.

FIG. 1 shows an exemplary scheme for separating forms of nucleic acid. The upper portion of the figure shows a sample including double-stranded DNA, single-stranded DNA and single-stranded RNA. RNA is reverse transcribed with a sequence specific or random polyT primer with a 5' RNA-identifying nucleic acid tag. After synthesis of a complementary DNA strand, the RNA template is degraded with RNase H or NaOH or ribosomal depletion by selective hybridization. The sample is then treated with capture probes (which can be sequence specific or agnostic) without denaturation of the sample. These probes hybridize to single-stranded molecules removing the single-stranded molecules from the sample. The double-stranded DNA molecules in the sample in this example are then blunt-ended and linked to adapters including nucleic acid tags. In this example, the adapters are Y-shaped and the double-stranded arm portion of the Y is ligated to the DNA molecules. Meanwhile the separated single-stranded nucleic acids are processed by the DNA protocol or NEBdirect protocol as discussed above including attachment of tags.

Figure 2:
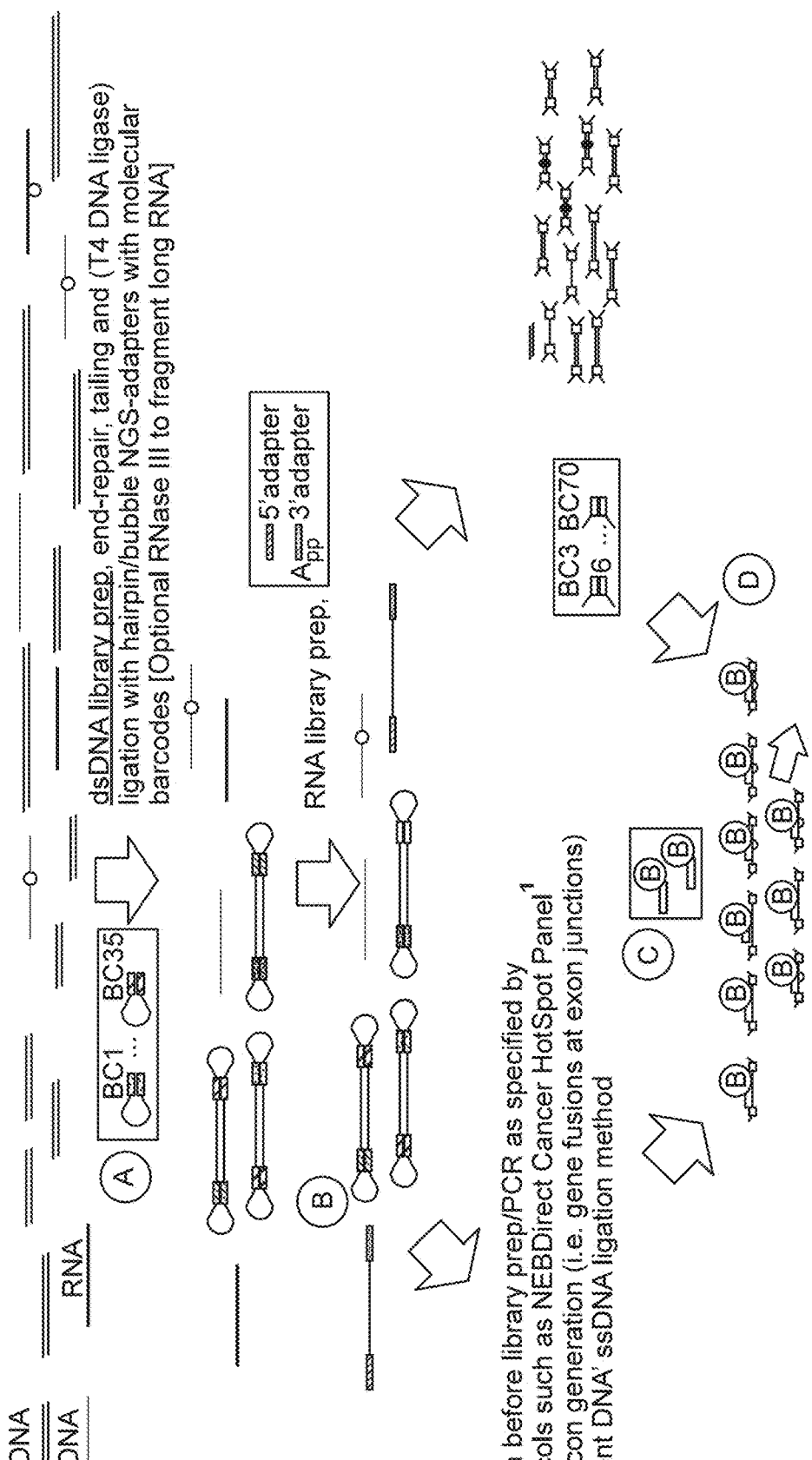
FIG. 2 shows a further exemplary scheme for partitioning RNA, single-stranded DNA and double-stranded DNA.

FIG. 2 shows a further exemplary scheme starting with a sample including double-stranded DNA, single-stranded DNA and single-stranded RNA, with a simplified workflow, most notably obviating a 5'DNA phosphorylation step. The double-stranded DNA in the sample is first ligated to hairpin adapters including nucleic acid tags. The sample is then 5'DNA dephosphorylated and RNA is then converted to cDNA and also ligated to different tags. Single-stranded DNA is then processed similarly to as in FIG. 1. In some embodiments, hairpin adapters can be cleaved into two strands prior to library amplification.

Figure 7:
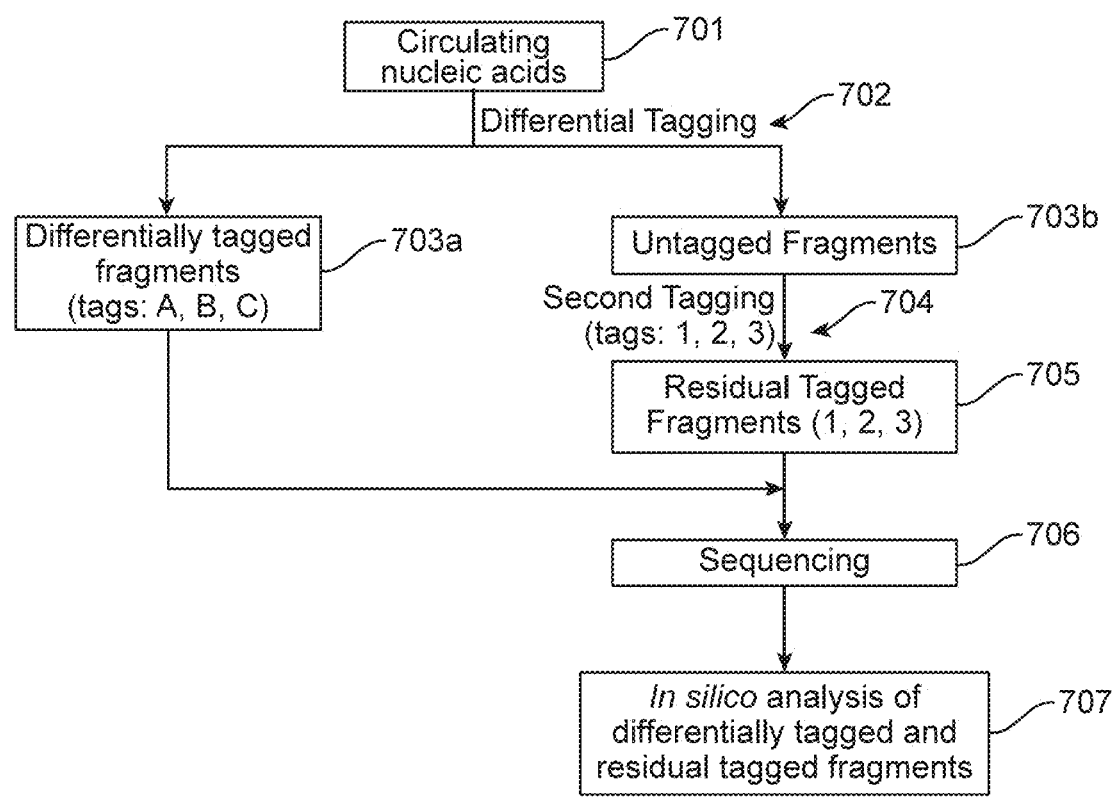
FIG. 7 shows an overview of differential tagging.

FIG. 7 illustrates one embodiment of differential tagging. In step 701, a population of nucleic acids is obtained. The nucleic acids can be circulating nucleic acids (cNA) such as from a liquid biopsy sample (serum, plasma or blood). In step 702, a first form of nucleic acid is differentially tagged to form a mixture (703) of a first, tagged, nucleic acid form and a second, non-tagged, nucleic acid form. Subsequently, in step 704, the second form of nucleic acids (or residual nucleic acids) is tagged with different labels. The method above can include 2 or more different differential tagging steps (702) prior to step 704. After tagging the two or more forms of nucleic acids in the population, the different forms can be In some embodiments partitioned. If the different forms are partitioned, the differentially tagged nucleic acids can then be pooled together prior to sequencing or sequenced separately. Preferably, differential tagging of different forms of nucleic acids occurs in one tube or reaction volume, and the entirety of tagged molecules is sequenced (without partitioning). Reads obtained from sequencing can be used for analysis to be performed on reads derived from different nucleic acids forms as well as the collective nucleic acid sample.

In some embodiments, the first form of nucleic acids that is differentially tagged is dsDNA and the differential tagging is performed by attaching to the dsDNA double-stranded adapters comprising a first set of tags. ssDNA (residual nucleic acids) is then tagged with a different set of tags (second set of tags).

In some embodiments, the first form of nucleic acids that is differentially tagged is DNA from open chromatin regions, and the tagging is performed by contacting the population of nucleic acids with Tn5 mediated transposase activity.

In some embodiments, the first form of nucleic acids that is differentially tagged is double-stranded nucleic acids, and the tagging is performed by attaching hairpin adaptors to double-stranded nucleic acids.

III. Partitioning Nucleic Acids with Different Extents of Modification

In certain embodiments described herein, a population of different forms of nucleic acids can be partitioned based on one or more characteristics of the nucleic acids prior to tagging and sequencing. By partitioning a heterogeneous nucleic acid population, one may increase rare signals, e.g., by enriching rare nucleic acid molecules that are more prevalent in one fraction (or partition) of the population. For example, a genetic variation present in RNA but less (or not) in DNA may be detected by partitioning RNA from DNA. Similarly, a genetic variation present in hyper-methylated DNA but less (or not) in hypomethylated DNA can be more easily detected by partitioning a sample into hyper-methylated and hypo-methylated nucleic acid molecules. By analyzing multiple fractions of a sample, a multi-dimensional analysis of a single molecule can be performed and hence, greater sensitivity can be achieved.

In some instances, a heterogeneous nucleic acid sample is partitioned into two or more partitions (e.g., at least 3, 4, 5, 6 or 7 partitions). In some embodiments, each partition is differentially tagged. Tagged partitions are then pooled together for collective sample prep and/or sequencing. The partitioning-tagging-pooling steps can occur more than once, with each round of partitioning occurring based on a different characteristics (examples provided herein), and tagged using differential tags that are distinguished from other partitions and partitioning means.

Examples of characteristics that can be used for partitioning include, sequence length, methylation level, nucleosome binding, sequence mismatch, immunoprecipitation, and/or proteins that bind to DNA. Resulting partitions can include one or more of the following nucleic acid forms: ribonucleic acids (RNA), single-stranded DNA (ssDNA), double-stranded DNA (dsDNA), shorter DNA fragments and longer DNA fragments. In some embodiments, a heterogeneous population of nucleic acids is partitioned into nucleic acid molecules associated with nucleosomes and nucleic acid molecules devoid of nucleosomes. Alternatively or additionally, a heterogeneous population of nucleic acids is partitioned into RNA and DNA. Alternatively or additionally, a heterogeneous population of nucleic acids may be partitioned into single-stranded DNA (ssDNA) and double-stranded DNA (dsDNA). Alternatively or additionally, a heterogeneous population of nucleic acids can be partitioned into nucleic acids with one or more epigenetic modifications and without the one or more epigenetic modifications. Examples of epigenetic modifications include presence or absence of methylation; level of methylation, type of methylation (5' cytosine); and association and level of association with one or more proteins, such as histones. Alternatively, or additionally, a heterogeneous population of nucleic acids may be partitioned based on nucleic acids length (e.g., molecules of up to 160 bp and molecules having a length of greater than 160 bp).

In some instances, each partition (representative of a different nucleic acid form) is differentially labelled, and the partitions are pooled together prior to sequencing. In other instances, the different forms are separately sequenced.

Figure 8:
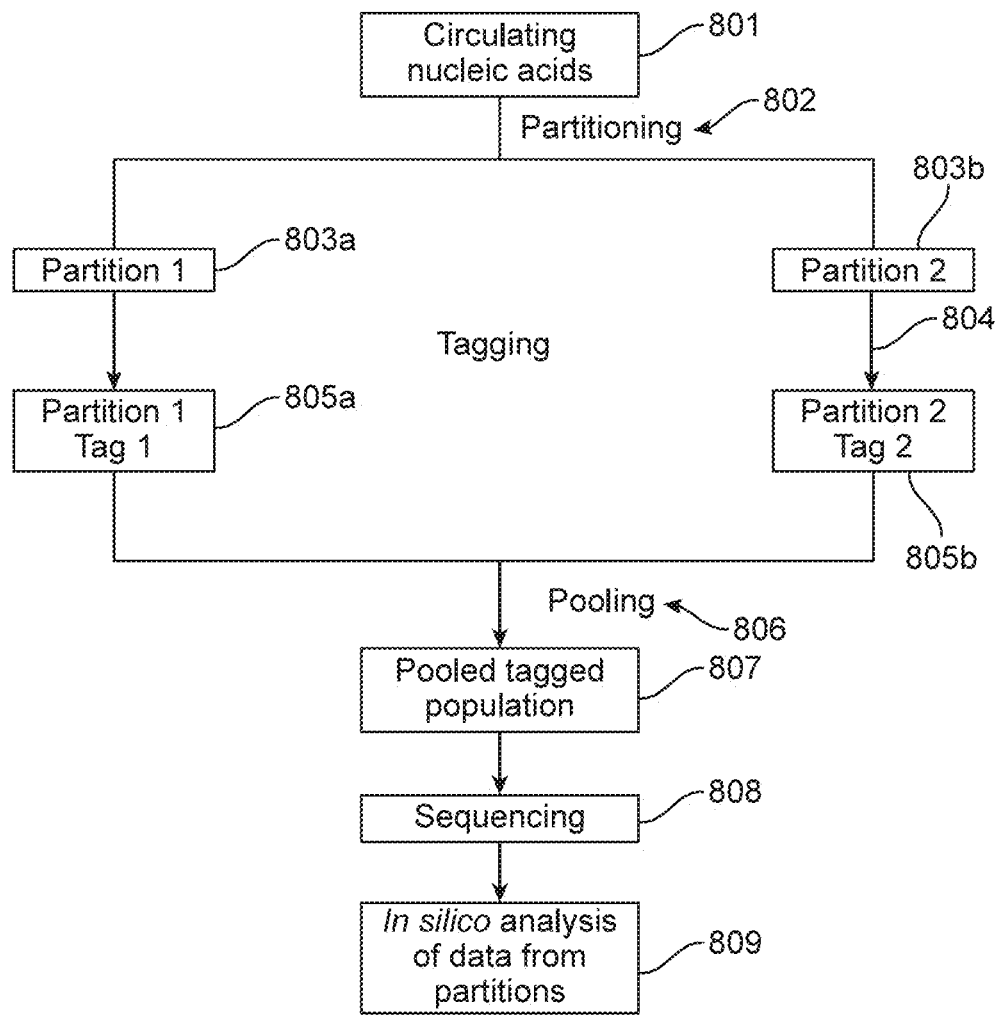
FIG. 8 shows an overview of partitioning methodology.

FIG. 8 illustrates one embodiment of the disclosure. A population of different nucleic acids (801) is partitioned (802) into two or more different partitions (803a, b). Each partition (803a, b) is representative of a different nucleic acid form. Each partition is distinctly tagged (804). The tagged nucleic acids are pooled together (807) prior to sequencing (808). Reads are analyzed, in silico. Tags are used to sort reads from different partitions. Analysis to detect genetic variants can be performed on a partition-by-partition level, as well as whole nucleic acid population level. For example, analysis can include in silico analysis to determine genetic variants, such as CNV, SNV, indel, fusion in nucleic acids in each partition. In some instances, in silico analysis can include determining chromatin structure. For example, coverage or copy number of sequence reads can be used to determine nucleosome positioning in chromatin. Higher coverage can correlate with higher nucleosome occupancy in genomic region while lower coverage can correlate with lower nucleosome occupancy or nucleosome depleted region (NDR).

Samples can include nucleic acids varying in modifications including post-replication modifications to nucleotides and binding, usually noncovalently, to one or more proteins.

In one embodiment, the population of nucleic acids is one obtained from a serum, plasma or blood sample from a subject suspected of having cancer or previously diagnosed with cancer. The nucleic acids include ones having varying levels of methylation. Methylation can occur from any one or more post-replication or transcriptional modifications. Post-replication modifications include modifications of the nucleotide cytosine, particularly, 5-methylcytosine, 5-hydroxymethylcytosine, 5-formylcytosine and 5-carboxylcytosine.

Partitioning of the nucleic acids is performed by contacting the nucleic acids with a methylation binding domain ("MBD") of a methylation binding protein ("MBP"). MBD binds to 5-methylcytosine (5 mC). MBD is coupled to paramagnetic beads, such as Dynabeads® M-280 Streptavidin via a biotin linker. Partitioning into fractions with different extents of methylation can be performed by eluting fractions by increasing the NaCl concentration.

In general, elution is a function of number of methylated sites per molecule, with molecules having more methylation eluting under increased salt concentrations. To elute the DNA into distinct populations based on the extent of methylation, one can use a series of elution buffers of increasing NaCl concentration. Salt concentration can range from about 100 nm to about 2500 mM NaCl. In one embodiment, the process results in three (3) partitions. Molecules are contacted with a solution at a first salt concentration and comprising a molecule comprising a methyl binding domain, which molecule can be attached to a capture moiety, such as streptavidin. At the first salt concentration a population of molecules will bind to the MBD and a population will remain unbound. The unbound population can be separated as a "hypomethylated" population. For example, a first partition representative of the hypomethylated form of DNA is that which remains unbound at a low salt concentration, e.g., 160 nM. A second partition representative of intermediate methylated DNA is eluted using an intermediate salt concentration, e.g., between 100 mM and 2000 mM concentration. This is also separated from the sample. A third partition representative of hypermethylated form of DNA is eluted using a high salt concentration, e.g., at least about 2000 nM.

Each partition is differentially tagged. Tags can be molecules, such as nucleic acids, containing information that indicates a feature of the molecule with which the tag is associated. For example, molecules can bear a sample tag (which distinguishes molecules in one sample from those in a different sample), a partition tag (which distinguishes molecules in one partition from those in a different partition) or a molecular tag (which distinguishes different molecules from one another (in both unique and non-unique tagging scenarios). In certain embodiments, a tag can comprise one or a combination of barcodes. As used herein, the term "barcode" refers to a nucleic acid molecule having a particular nucleotide sequence, or to the nucleotide sequence, itself, depending on context. A barcode can have, for example, between 10 and 100 nucleotides. A collection of barcodes can have degenerate sequences or can have sequences having a certain hamming distance, as desired for the specific purpose. So, for example, a sample index, partition index or molecular index can be comprised of one barcode or a combination of two barcodes, each attached to different ends of a molecule.

Tags can be used to label the individual polynucleotide population partitions so as to correlate the tag (or tags) with a specific partition. In some embodiments, a single tag can be used to label a specific partition. In some embodiments, multiple different tags can be used to label a specific partition. In embodiments employing multiple different tags to label a specific partition, the set of tags used to label one partition can be readily differentiated for the set of tags used to label other partitions. In some embodiments, the tags may have additional functions, for example the tags can be used to index sample sources or used as unique molecular identifiers (which can be used to improve the quality of sequencing data by differentiating sequencing errors from mutations). Similarly, in some embodiments, the tags may have additional functions, for example the tags can be used to index sample sources or used as non-unique molecular identifiers (which can be used to improve the quality of sequencing data by differentiating sequencing errors from mutations).

In one embodiment, partition tagging comprises tagging molecules in each partition with the equivalent of a sample tag. After re-combining partitions and sequencing molecules, the sample tags identify the source partition. In another embodiment, different partitions are tagged with different sets of molecular tags, e.g., comprised of a pair barcodes. In this way, each molecular barcode indicates the source partition as well being useful to distinguish molecules within a partition. For example, a first set of 35 barcodes can be used to tag molecules in a first partition, while a second set of 35 barcodes can be used tag molecules in a second partition.

While tags may be attached to molecules already partition based on one or more characteristics, the final tagged molecules in the library may no longer possess that characteristic. For example, while single stranded DNA molecules may be partitioned and tagged, the final tagged molecules in the library are likely to be double stranded. Similarly, while RNA may be subject to partition, in the final library, tagged molecules derived from these RNA molecules are likely to be DNA. Accordingly, the tag attached to molecule in the library typically indicates the characteristic of the "parent molecule" from which the ultimate tagged molecule is derived, not necessarily to characteristic of the tagged molecule, itself.

For example, barcodes 1, 2, 3, 4, etc. are used to tag and label molecules in the first partition; barcodes A, B, C, D, etc. are used to tag and label molecules in the second partition; and barcodes a, b, c, d, etc. are used to tag and label molecules in the third partition. Differentially tagged partitions can be pooled prior to sequencing. Differentially tagged partitions can be separately sequenced or sequenced together concurrently, e.g., in the same flow cell of an Illumina sequencer.

After sequencing, reads are analyzed detect genetic variants can be performed on a partition-by-partition level, as well as whole nucleic acid population level. Tags are used to sort reads from different partitions. Analysis can include in silico analysis to determine genetic variants and chromatin structure using sequence information, genomic coordinates length and coverage or copy number. Higher coverage can correlate with higher nucleosome occupancy in genomic region while lower coverage can correlate with lower nucleosome occupancy or nucleosome depleted region (NDR).

In some embodiments, the nucleic acids in the original population can be DNA and/or RNA, single-stranded and/or double-stranded. Partitioning based on single v. double stranded-ness, can be accomplished by, e.g. using labelled capture probes to partition ssDNA and using double stranded adapters to partition dsDNA. Partitioning based on the RNA v. DNA composition include, but is not limited to using double stranded adapters to partition dsDNA and using reverse transcription with or without capture probes to partition RNA.

The affinity agents can be antibodies with the desired specificity, natural binding partners or variants thereof (Bock et al., Nat Biotech 28: 1106-1114 (2010); Song et al., Nat Biotech 29, 68-72 (2011)), or artificial peptides selected e.g., by phage display to have specificity to a given target.

Examples of capture moieties contemplated herein include methyl binding domain (MBDs) and methyl binding proteins (MBPs). Examples of MBPs contemplated herein include, but are not limited to:

(a) MeCP2 is a protein preferentially binding to 5-methylcytosine over unmodified cytosine.
(b) RPL26, PRP8 and the DNA mismatch repair protein MHS6 preferentially bind to 5-hydroxymethyl-cytosine over unmodified cytosine.
(c) FOXK1, FOXK2, FOXP1, FOXP4 and FOXI3 preferably bind to 5-formyl-cytosine over unmodified cytosine (Iurlaro et al., Genome Biol. 14, R119 (2013)).
(d) Antibodies specific to one or more methylated nucleotide bases.

Likewise, partitioning of different forms of nucleic acids can be performed using histone binding proteins which can separate nucleic acids bound to histones from free or unbound nucleic acids. Examples of histone binding proteins that can be used in the methods disclosed herein include RBBP4, RbAp48 and SANT domain peptides.

Although for some affinity agents and modifications, binding to the agent may occur in an essentially all or none manner depending on whether a nucleic acid bears a modification, the separation may be one of degree. In such instances, nucleic acids overrepresented in a modification bind to the agent at a greater extent that nucleic acids underrepresented in the modification. Alternatively, nucleic acids having modifications may bind in an all or nothing manner. But then, various levels of modifications may be sequentially eluted from the binding agent.

For example, in some embodiments, partitioning can be binary or based on degree/level of modifications. For example, all methylated fragments can be partitioned from unmethylated fragments using methyl-binding domain proteins (e.g., MethylMinder Methylated DNA Enrichment Kit (ThermoFisher Scientific). Subsequently, additional partitioning may involve eluting fragments having different levels of methylation by adjusting the salt concentration in a solution with the methyl-binding domain and bound fragments. As salt concentration increases, fragments having greater methylation levels are eluted.

In some instances, the final partitions are representatives of nucleic acids having different extents of modifications (overrepresentative or underrepresentative of modifications). Overrepresentation and underrepresentation can be defined by the number of modifications born by a nucleic acid relative to the median number of modifications per strand in a population. For example, if the median number of 5-methylcytosine residues in nucleic acid in a sample is 2, a nucleic acid including more than two 5-methylcytosine residues is overrepresented in this modification and a nucleic acid with 1 or zero 5-methylcytosine residues is underrepresented. The effect of the affinity separation is to enrich for nucleic acids overrepresented in a modification in a bound phase and for nucleic acids underrepresented in a modification in an unbound phase (i.e. in solution). The nucleic acids in the bound phase can be eluted before subsequent processing.

When using MethylMiner Methylated DNA Enrichment Kit (ThermoFisher Scientific) various levels of methylation can be partitioned using sequential elutions. For example, a hypomethylated partition (no methylation) can be separated from a methylated partition by contacting the nucleic acid population with the MBD from the kit, which is attached to magnetic beads. The beads are used to separate out the methylated nucleic acids from the non-methylated nucleic acids. Subsequently, one or more elution steps are performed sequentially to elute nucleic acids having different levels of methylation. For example, a first set of methylated nucleic acids can be eluted at a salt concentration of 160 mM or higher, e.g., at least 200 mM, 300 mM, 400 mM, 500 mM, 600 mM, 700 mM, 800 mM, 900 mM, 1000 mM, or 2000 mM. After such methylated nucleic acids are eluted, magnetic separation is once again used to separate higher level of methylated nucleic acids from those with lower level of methylation. The elution and magnetic separation steps can repeat themselves to create various partitions such as a hypomethylated partition (representative of no methylation), a methylated partition (representative of low level of methylation), and a hyper methylated partition (representative of high level of methylation).

In some methods, nucleic acids bound to an agent used for affinity separation are subjected to a wash step. The wash step washes off nucleic acids weakly bound to the affinity agent. Such nucleic acids can be enriched in nucleic acids having the modification to an extent close to the mean or median (i.e., intermediate between nucleic acids remaining bound to the solid phase and nucleic acids not binding to the solid phase on initial contacting of the sample with the agent).

The affinity separation results in at least two, and sometimes three or more partitions of nucleic acids with different extents of a modification. While the partitions are still separate, the nucleic acids of at least one partition, and usually two or three (or more) partitions are linked to nucleic acid tags, usually provided as components of adapters, with the nucleic acids in different partitions receiving different tags that distinguish members of one partition from another. The tags linked to nucleic acid molecules of the same partition can the same or different from one another. But if different from one another, the tags may have part of their code in common so as to identify the molecules to which they are attached as being of a particular partition.

Figure 3:
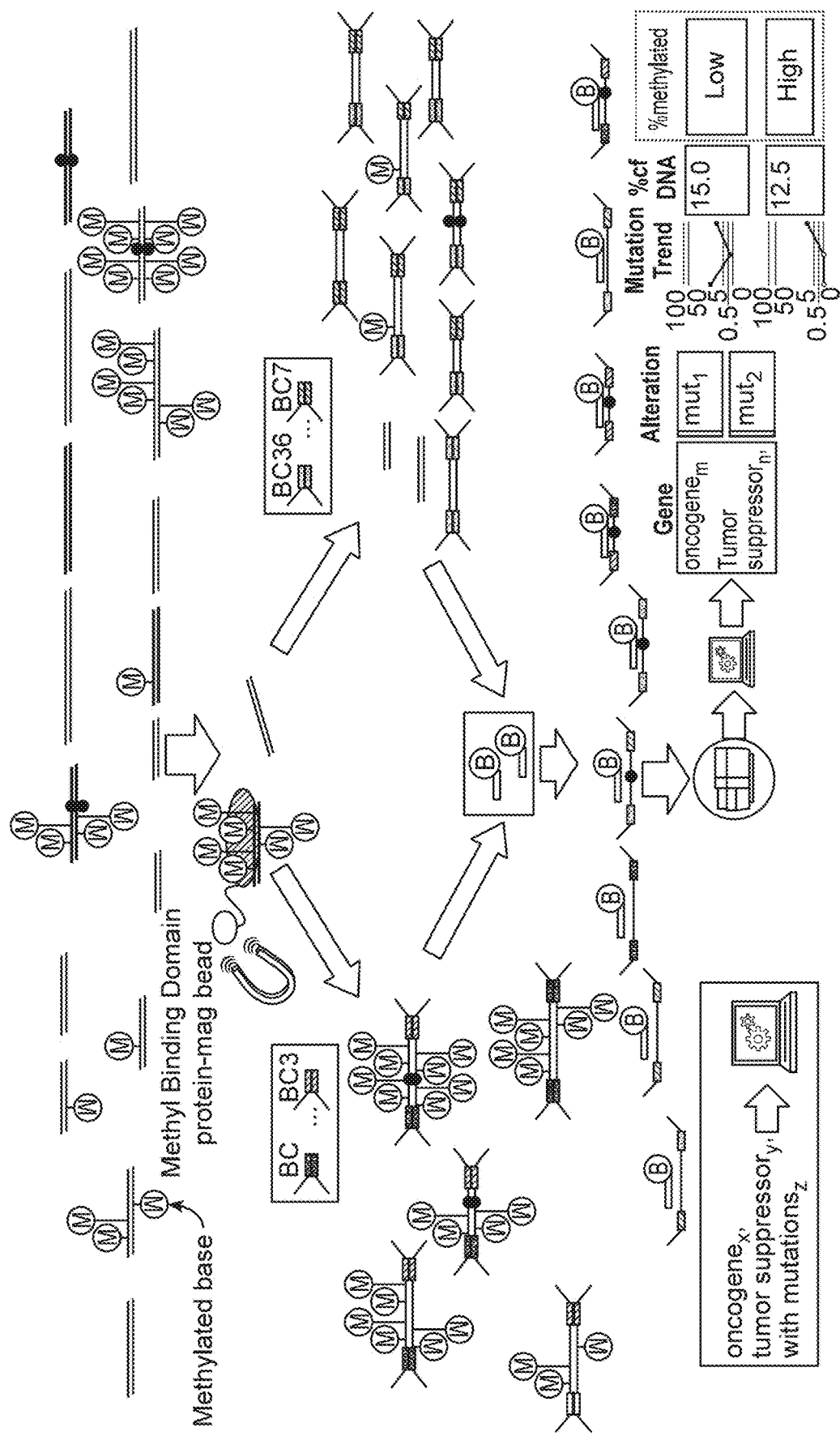
FIG. 3 shows a scheme for analyzing DNA containing varying extents of 5-methyl cytosine representation.

FIG. 3 shows an exemplary scheme. The sample includes nucleic acids with different extents of methylation, some of which also have genetic variations. The samples are contacted with magnetic beads linked to an affinity reagent preferentially binding to 5-methylcytosine over cytosine. Affinity purification results in two partitions of nucleic acids. The partition in the left of the figure represents nucleic acids binding to the affinity reagents and is enriched in nucleic acids overrepresented in 5-methylcytosine. The partition on the right represents nucleic acids not binding to the affinity reagent and is enriched in nucleic acids lacking or underrepresented in 5-methylcytosine. The two partitions are then attached to Y-shaped adapters including differential nucleic acid tags and amplified. The amplified nucleic acids are then assayed for sequence data, the sequence of sample nucleic acid indicating genetic variations, and the sequence of tags indicating which partition a sample nucleic acid partitioned into, thereby indicating an extent of modification.

Figure 24:
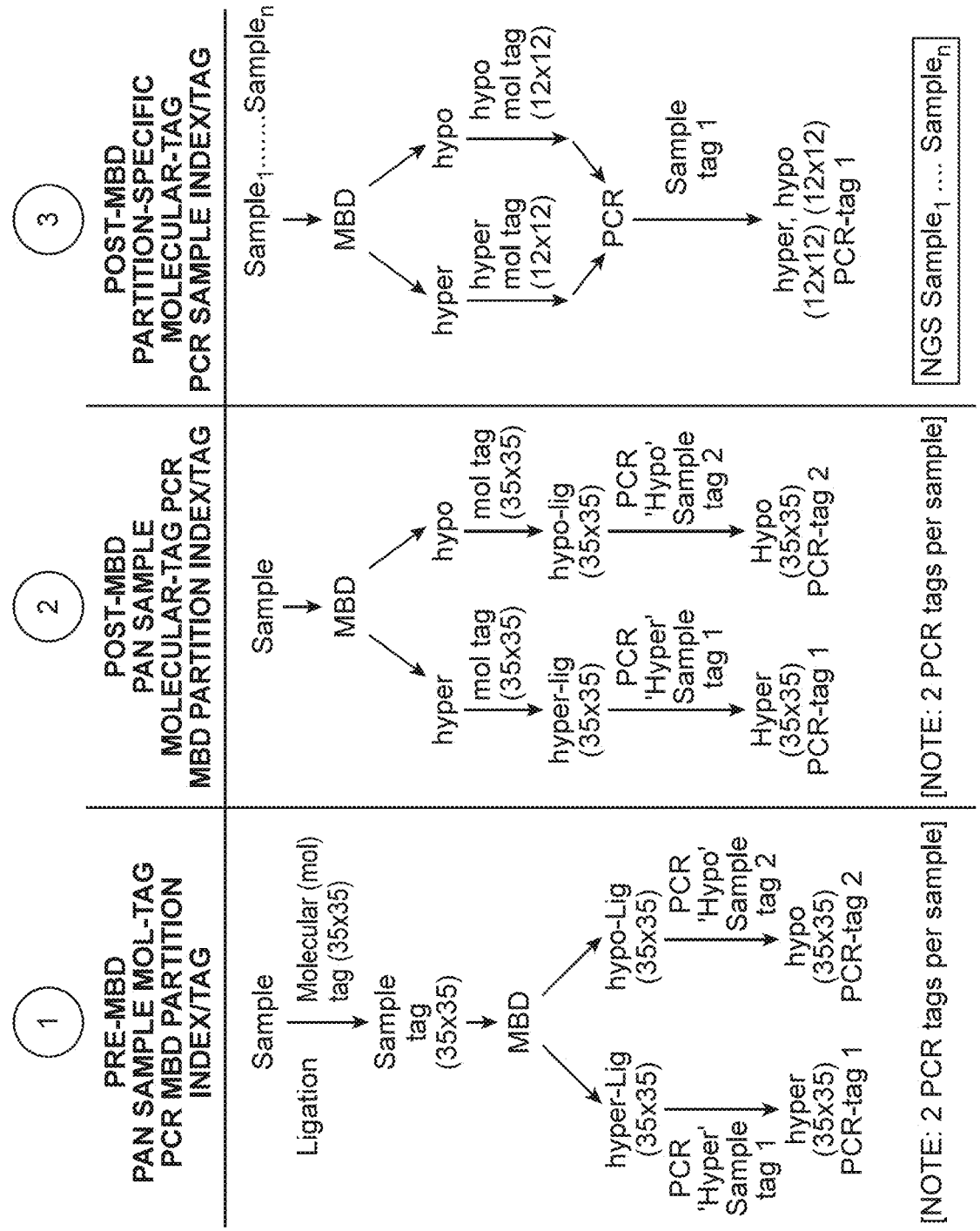
FIG. 24 provides three examples of strategies for tagging nucleic acid molecules partitioned or fractionated using methyl-binding domain proteins (MBD-partitioning).

FIG. 24 provides an illustrative example of MBD-partitioning and tagging approaches. In workflow (1), one set of molecular tags (e.g., 35×35 tags) can be applied to the whole sample prior to partitioning. After partitioning, in this example, for hyper- and hypo-methylated forms, the molecules in each partition are optionally amplified and then independently sequenced. In workflow (2), the molecules in a sample are partitioned, e.g., based on methylation characteristics. Each partition is separately tagged, amplified and sequenced. In workflow (3), molecules in each of a plurality of samples are subject to partition, tagged with partition-specific tags, pooled and amplified. Molecules in each sample are then provided with a sample tag, to deconvolute the sample from which they originated.

In some embodiments, the nucleic acid molecules can be fractionated into different partitions based on the nucleic acid molecules that are bound to a specific protein or a fragment thereof and those that are not bound to that specific protein or fragment thereof. Nucleic acid molecules can be fractionated based on DNA-protein binding. Protein-DNA complexes can be fractionated based on a specific property of a protein. Examples of such properties include various epitopes, modifications (e.g., histone methylation or acetylation) or enzymatic activity. Examples of proteins which may bind to DNA and serve as a basis for fractionation may include, but are not limited to, protein A and protein G. Any suitable method can be used to fractionate the nucleic acid molecules based on protein bound regions. Examples of methods used to fractionate nucleic acid molecules based on protein bound regions include, but are not limited to, SDS-PAGE, chromatin-immuno-precipitation (ChIP), heparin chromatography, and asymmetrical field flow fractionation (AF4).

IV. Determination of 5-Methylcytosine Pattern of Nucleic Acids

Bisulfite-based sequencing and variants thereof provides a means of determining the methylation pattern of a nucleic acid. In some embodiments, determining the methylation pattern comprises distinguishing 5-methylcytosine (5 mC) from non-methylated cytosine. In some embodiments, determining methylation pattern comprises distinguishing $N^6$-methyladenine from non-methylated adenine. In some embodiments, determining the methylation pattern comprises distinguishing 5-hydroxymethylcytosine (5 hmC), 5-formylcytosine (5fC), and 5-carboxylcytosine (5caC) from non-methylated cytosine. Examples of bisulfite sequencing include, but are not limited to oxidative bisulfite sequencing (OX-BS-seq), Tet-assisted bisulfite sequencing (TAB-seq), and reduced bisulfite sequencing (redBS-seq).

Oxidative bisulfite sequencing (OX-BS-seq) is used to distinguish between 5 mC and 5 hmC, by first converting the 5 hmC to 5fC, and then proceeding with bisulfite sequencing as previously described. Tet-assisted bisulfite sequencing (TAB-seq) can also be used to distinguish 5 mc and 5 hmC. In TAB-seq, 5 hmC is protected by glucosylation. A Tet enzyme is then used to convert 5 mC to 5caC before proceeding with bisulfite sequencing, as previously described. Reduced bisulfite sequencing is used to distinguish 5fC from modified cytosines.

Generally, in bisulfite sequencing, a nucleic acid sample is divided into two aliquots and one aliquot is treated with bisulfite. The bisulfite converts native cytosine and certain modified cytosine nucleotides (e.g. 5-formylcytosine or 5-carboxylcytosine) to uracil whereas other modified cytosines (e.g., 5-methylcytosine, 5-hydroxymethylcytosine) are not converted. Comparison of nucleic acid sequences of molecules from the two aliquots indicates which cytosines were and were not converted to uracils. Consequently, cytosines which were and were not modified can be determined. The initial splitting of the sample into two aliquots is disadvantageous for samples containing only small amounts of nucleic acids, and/or composed of heterogeneous cell/tissue origins such as bodily fluids containing cell-free DNA.

The present disclosure provides methods allowing bisulfite sequencing and variants thereof. These methods work by linking nucleic acids in a population to a capture moiety, i.e., a label that can be captured or immobilized. Capture moieties include, without limitation, biotin, avidin, streptavidin, a nucleic acid comprising a particular nucleotide sequence, a hapten recognized by an antibody, and magnetically attractable particles. The extraction moiety can be a member of a binding pair, such as biotin/streptavidin or hapten/antibody. In some embodiments, a capture moiety that is attached to an analyte is captured by its binding pair which is attached to an isolatable moiety, such as a magnetically attractable particle or a large particle that can be sedimented through centrifugation. The capture moiety can be any type of molecule that allows affinity separation of nucleic acids bearing the capture moiety from nucleic acids lacking the capture moiety. Exemplary capture moieties are biotin which allows affinity separation by binding to streptavidin linked or linkable to a solid phase or an oligonucleotide, which allows affinity separation through binding to a complementary oligonucleotide linked or linkable to a solid phase. Following linking of capture moieties to sample nucleic acids, the sample nucleic acids serve as templates for amplification. Following amplification, the original templates remain linked to the capture moieties but amplicons are not linked to capture moieties.

The capture moiety can be linked to sample nucleic acids as a component of an adapter, which may also provide amplification and/or sequencing primer binding sites. In some methods, sample nucleic acids are linked to adapters at both ends, with both adapters bearing a capture moiety. Preferably any cytosine residues in the adapters are modified, such as by 5 methylcytosine, to protect against the action of bisulfite. In some instances, the capture moieties are linked to the original templates by a cleavable linkage (e.g., photocleavable desthiobiotin-TEG or uracil residues cleavable with USER™ enzyme, Chem. Commun. (Camb). 2015 Feb. 21; 51(15): 3266-3269), in which case the capture moieties can, if desired, be removed.

The amplicons are denatured and contacted with an affinity reagent for the capture tag. Original templates bind to the affinity reagent whereas nucleic acid molecules resulting from amplification do not. Thus, the original templates can be separated from nucleic acid molecules resulting from amplification.

Following separation or partition, the respective populations of nucleic acids (i.e., original templates and amplification products) can be subjected to bisulfite treatment with the original template population receiving bisulfite treatment and the amplification products not. Alternatively, the amplification products can be subjected to bisulfite treatment and the original template population not. Following such treatment, the respective populations can be amplified (which in the case of the original template population converts uracils to thymines). The populations can also be subjected to biotin probe hybridization for enrichment. The respective populations are then analyzed and sequences compared to determine which cytosines were 5-methylated (or 5-hydroxymethylated) in the original. Detection of a T nucleotide in the template population (corresponding to an unmethylated cytosine converted to uracil) and a C nucleotide at the corresponding position of the amplified population indicates an unmodified C. The presence of C's at corresponding positions of the original template and amplified populations indicates a modified C in the original sample.

Figure 4:
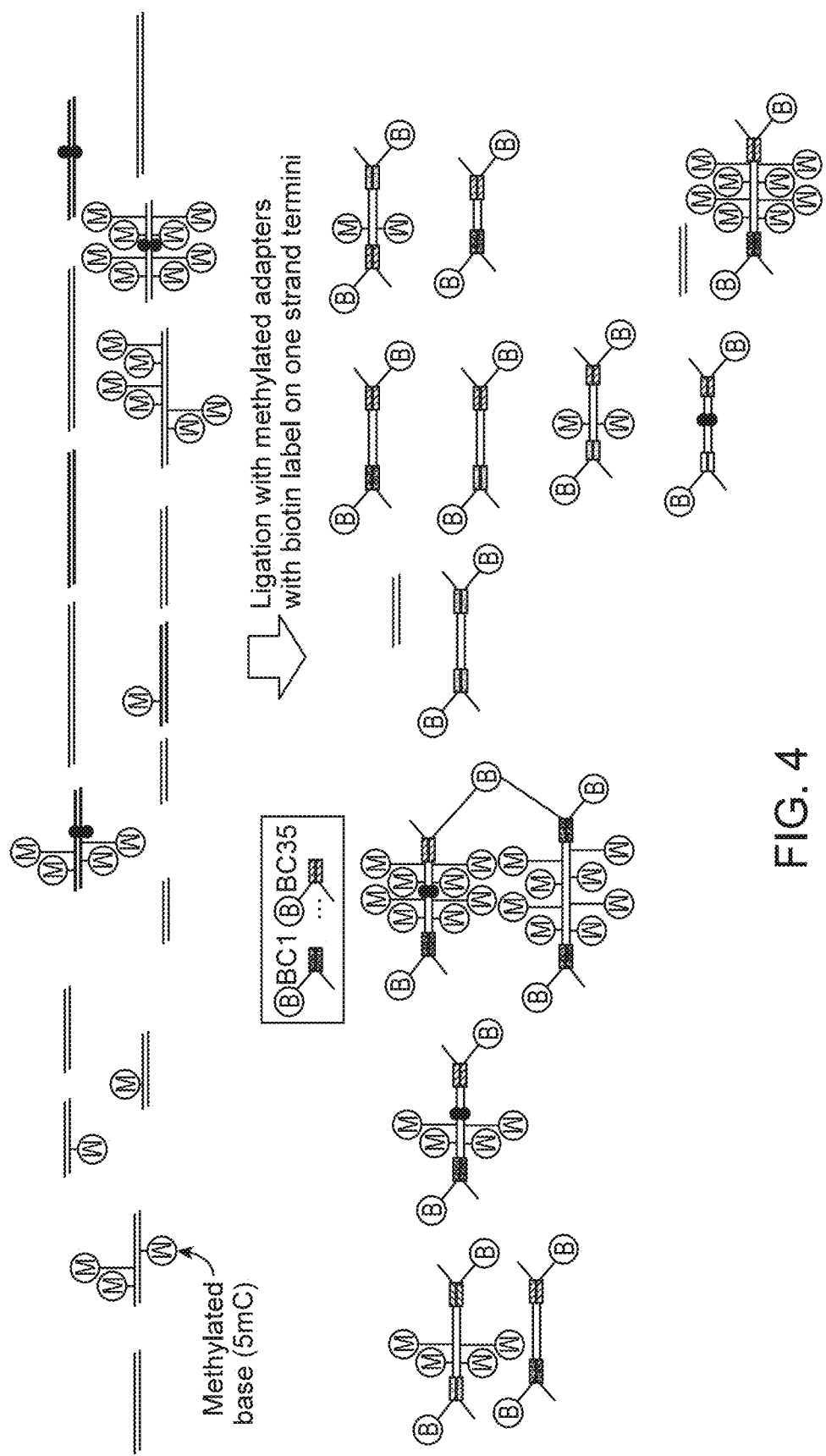
FIG. 4 shows a scheme for bisulfite sequencing of methylated DNA.
Figure 4:
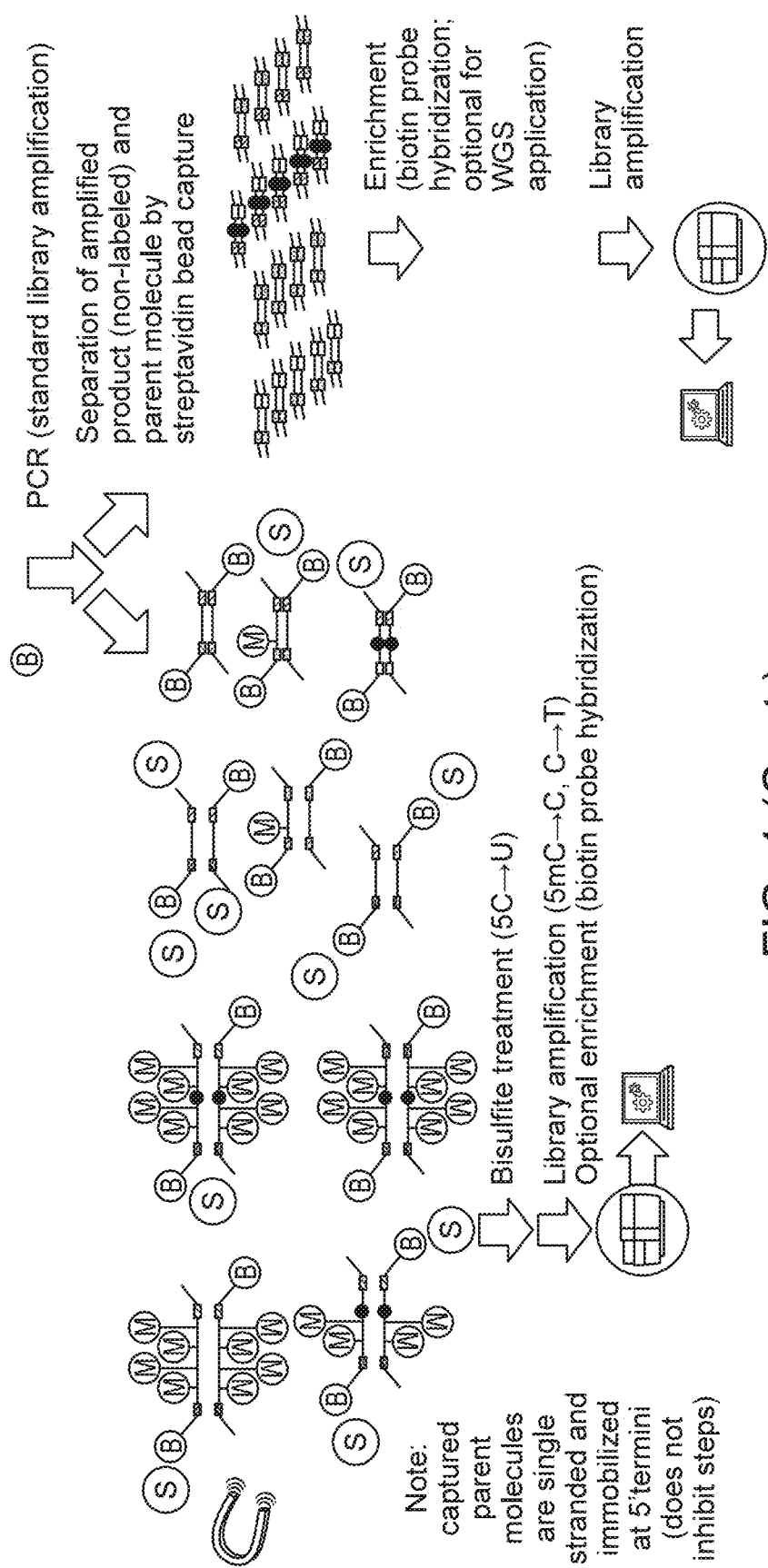

In some embodiments, a method uses sequential DNA-seq and bisulfite-seq (BIS-seq) NGS library preparation of molecular tagged DNA libraries (see FIG. 4). This process is performed by labeling of adapters (e.g., biotin), DNA-seq amplification of whole library, parent molecule recovery (e.g. streptavidin bead pull down), bisulfite conversion and BIS-seq. In some embodiments, the method identifies 5-methylcytosine with single-base resolution, through sequential NGS-preparative amplification of parent library molecules with and without bisulfite treatment. This can be achieved by modifying the 5-methyl-ated NGS-adapters (directional adapters; Y-shaped/forked with 5-methylcytosine replacing) used in BIS-seq with a label (e.g., biotin) on one of the two adapter strands. Sample DNA molecules are adapter ligated, and amplified (e.g., by PCR). As only the parent molecules will have a labeled adapter end, they can be selectively recovered from their amplified progeny by label-specific capture methods (e.g., streptavidin-magnetic beads). As the parent molecules retain 5-methylation marks, bisulfite conversion on the captured library will yield single-base resolution 5-methylation status upon BIS-seq, retaining molecular information to corresponding DNA-seq. In some embodiments, the bisulfite treated library can be combined with a non-treated library prior to enrichment/NGS by addition of a sample tag DNA sequence in standard multiplexed NGS workflow. As with BIS-seq workflows, bioinformatics analysis can be carried out for genomic alignment and 5-methylated base identification. In sum, this method provides the ability to selectively recover the parent, ligated molecules, carrying 5-methylcytosine marks, after library amplification, thereby allowing for parallel processing for bisulfite converted DNA. This overcomes the destructive nature of bisulfite treatment on the quality/sensitivity of the DNA-seq information extracted from a workflow. With this method, the recovered ligated, parent DNA molecules (via labeled adapters) allow amplification of the complete DNA library and parallel application of treatments that elicit epigenetic DNA modifications. The present disclosure discusses the use of BIS-seq methods to identify cytosine5-methylation (5-methylcytosine), but this should is not limiting. Variants of BIS-seq have been developed to identify hydroxymethylated cytosines (5 hmC; OX-BS-seq, TAB-seq), formylcytosine (5fC; redBS-seq) and carboxylcytosines. These methodologies can be implemented with the sequential/parallel library preparation described herein.

Alternative Methods of Modified Nucleic Acid Analysis

The disclosure provides alternative methods for analyzing modified nucleic acids (e.g., methylated, linked to histones and other modifications discussed above). In some such methods, a population of nucleic acids bearing the modification to different extents (e.g., 0, 1, 2, 3, 4, 5 or more methyl groups per nucleic acid molecule) is contacted with adapters before fractionation of the population depending on the extent of the modification. Adapters attach to either one end or both ends of nucleic acid molecules in the population. Preferably, the adapters include different tags of sufficient numbers that the number of combinations of tags results in a low probability e.g., 95, 99 or 99.9% of two nucleic acids with the same start and stop points receiving the same combination of tags. Following attachment of adapters, the nucleic acids are amplified from primers binding to the primer binding sites within the adapters. Adapters, whether bearing the same or different tags, can include the same or different primer binding sites, but preferably adapters include the same primer binding site. Following amplification, the nucleic acids are contacted with an agent that preferably binds to nucleic acids bearing the modification (such as the previously described such agents). The nucleic acids are separated into at least two partitions differing in the extent to which the nucleic acids bear the modification from binding to the agents. For example, if the agent has affinity for nucleic acids bearing the modification, nucleic acids overrepresented in the modification (compared with median representation in the population) preferentially bind to the agent, whereas nucleic acids underrepresented for the modification do not bind or are more easily eluted from the agent. Following separation, the different partitions can then be subject to further processing steps, which typically include further amplification, and sequence analysis, in parallel but separately. Sequence data from the different partitions can then be compared.

Figure 5:
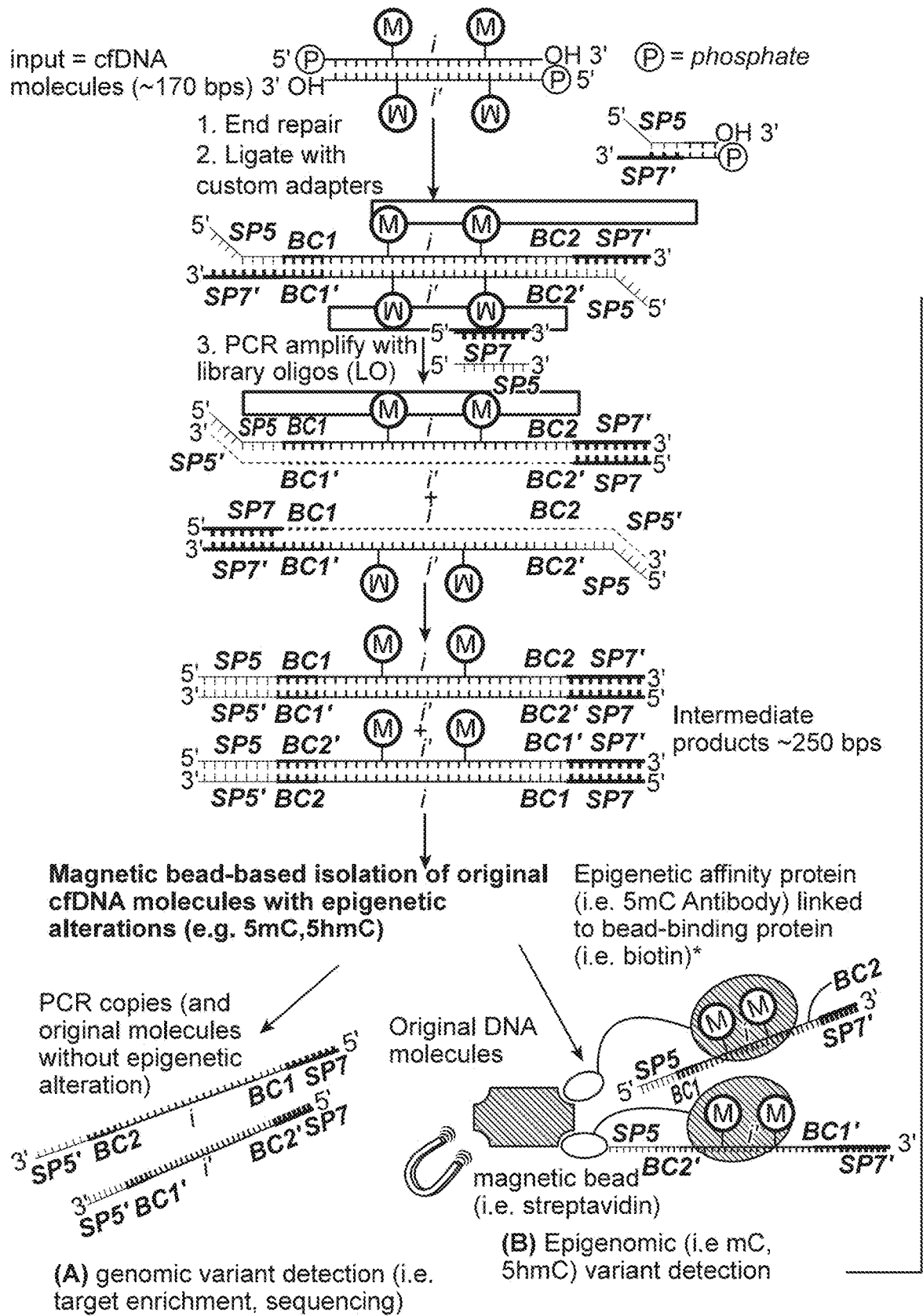
FIG. 5 shows a further scheme for analyzing DNA containing varying extents of 5-methyl cytosine representation.
Figure 5:
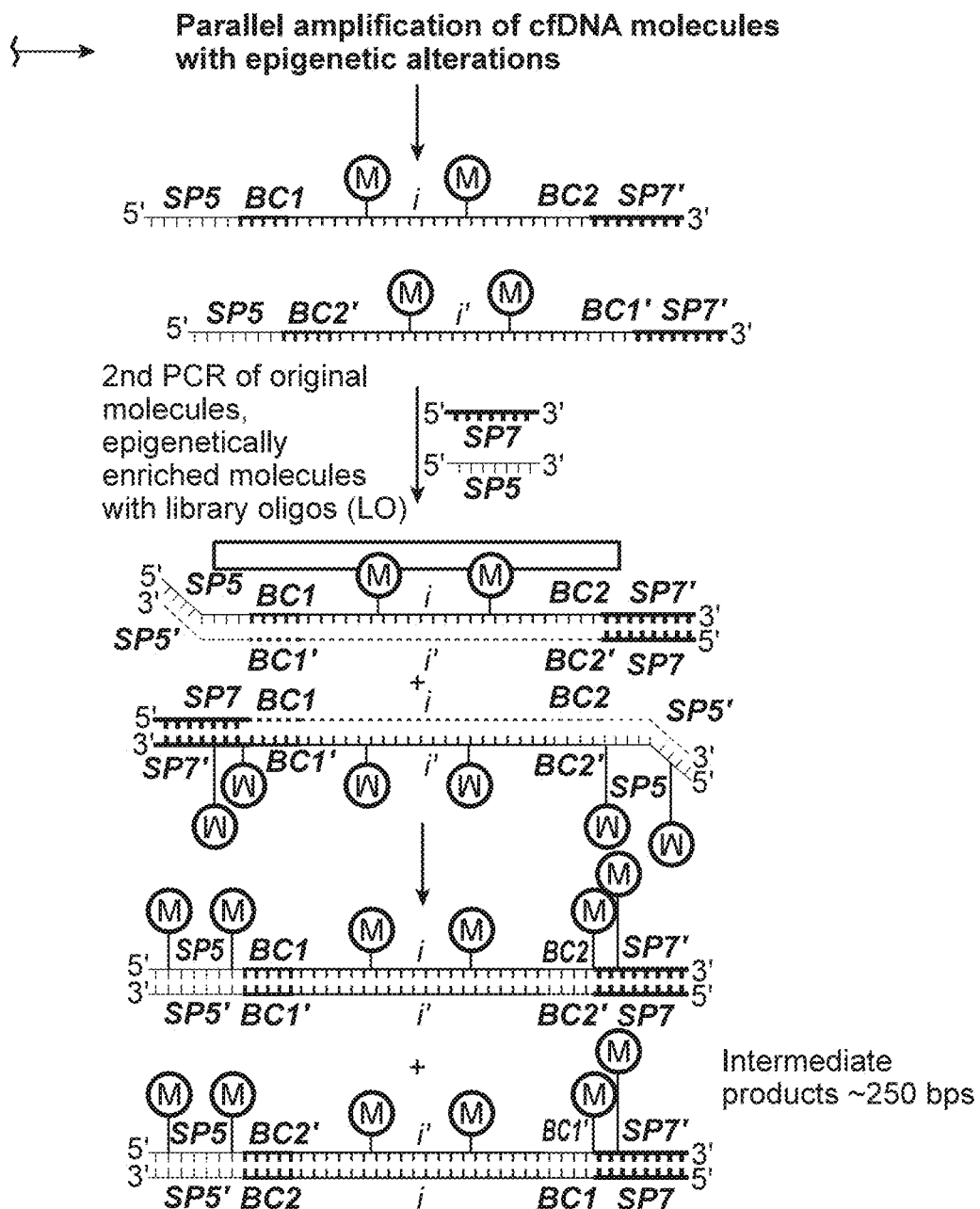

An exemplary scheme for performing such a separation is shown in FIG. 5. Nucleic acids are linked at both ends to Y-shaped adapters including primer binding sites and tags. The molecules are amplified. The amplified molecules are then fractionated by contact with an antibody preferentially binding to 5-methylcytosine to produce two partitions. One partition includes original molecules lacking methylation and amplification copies having lost methylation. The other partition includes original DNA molecules with methylation. The two partitions are then processed and sequenced separately with further amplification of the methylated partition. The sequence data of the two partitions can then be compared. In this example, tags are not used to distinguish between methylated and unmethylated DNA but rather to distinguish between different molecules within these partitions so that one can determine whether reads with the same start and stop points are based on the same or different molecules.

The disclosure provides further methods for analyzing a population of nucleic acid in which at least some of the nucleic acids include one or more modified cytosine residues, such as 5-methylcytosine and any of the other modifications described previously. In these methods, the population of nucleic acids is contacted with adapters including one or more cytosine residues modified at the 5C position, such as 5-methylcytosine. Preferably all cytosine residues in such adapters are also modified, or all such cytosines in a primer binding region of the adapters are modified. Adapters attach to both ends of nucleic acid molecules in the population. Preferably, the adapters include different tags of sufficient numbers that the number of combinations of tags results in a low probability e.g., 95, 99 or 99.9% of two nucleic acids with the same start and stop points receiving the same combination of tags. The primer binding sites in such adapters can be the same or different, but are preferably the same. After attachment of adapters, the nucleic acids are amplified from primers binding to the primer binding sites of the adapters. The amplified nucleic acids are split into first and second aliquots. The first aliquot is assayed for sequence data with or without further processing. The sequence data on molecules in the first aliquot is thus determined irrespective of the initial methylation state of the nucleic acid molecules. The nucleic acid molecules in the second aliquot are treated with bisulfite. This treatment converts unmodified cytosines to uracils. The bisulfite treated nucleic acids are then subjected to amplification primed by primers to the original primer binding sites of the adapters linked to nucleic acid. Only the nucleic acid molecules originally linked to adapters (as distinct from amplification products thereof) are now amplifiable because these nucleic acids retain cytosines in the primer binding sites of the adapters, whereas amplification products have lost the methylation of these cytosine residues, which have undergone conversion to uracils in the bisulfite treatment. Thus, only original molecules in the populations, at least some of which are methylated, undergo amplification. After amplification, these nucleic acids are subject to sequence analysis. Comparison of sequences determined from the first and second aliquots can indicate among other things, which cytosines in the nucleic acid population were subject to methylation.

Figure 6:
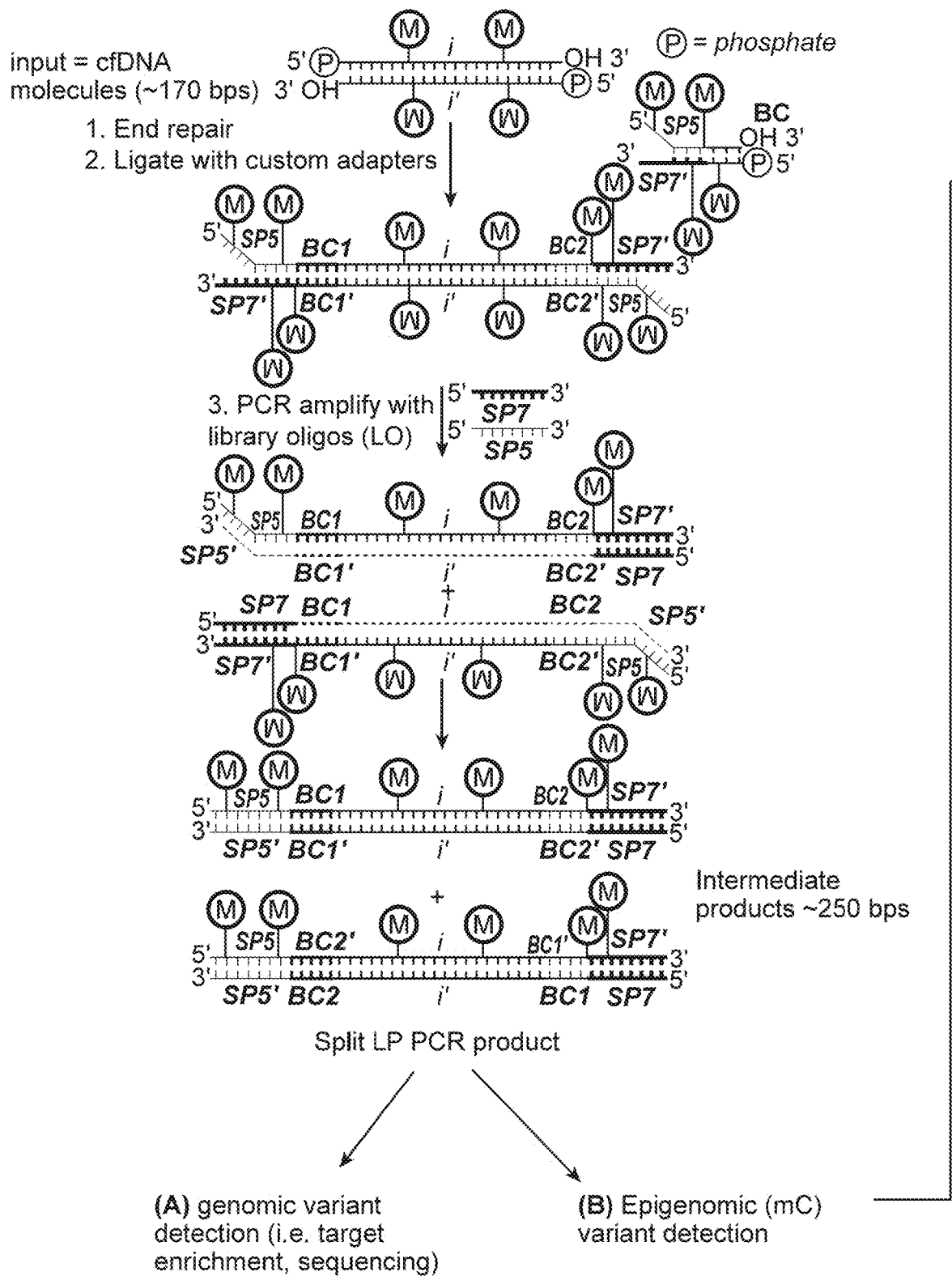
FIG. 6 shows a further scheme for bisulfite sequencing of methylated DNA.
Figure 6:
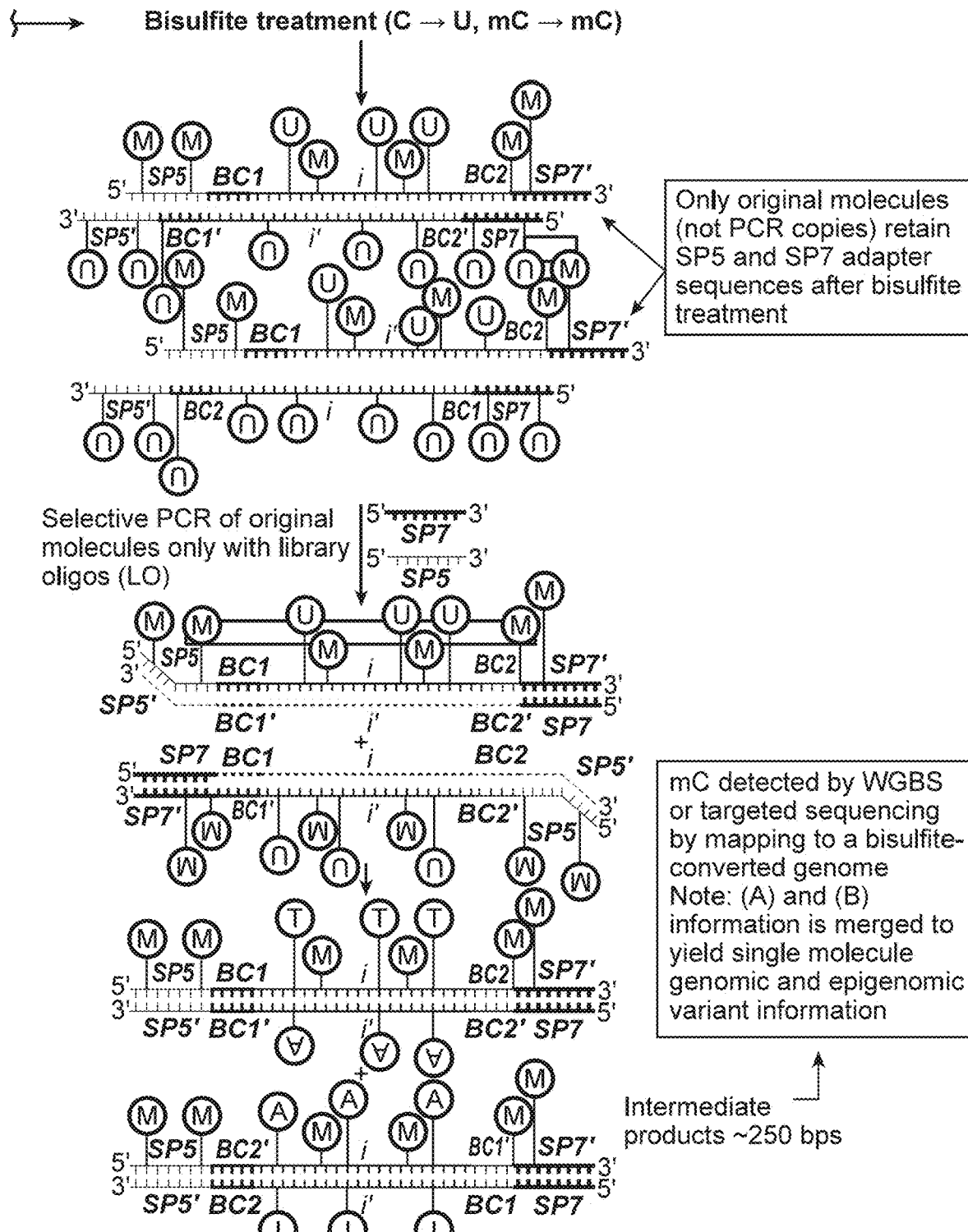

An exemplary scheme for this analysis is shown in FIG. 6. Methylated DNA is linked to Y-shaped adapters at both ends including primer binding sites and tags. The cytosines in the adapters are 5-methylated. The methylation of the primers serves to protect the primer binding sites in a subsequent bisulfite step. After attachment of adapters, the DNA molecules are amplified. The amplification product is split into two aliquots for sequencing with and without bisulfite treatment. The aliquot not subjected to bisulfite sequencing can be subjected to sequence analysis with or without further processing. The other aliquot is treated with bisulfite, which converts unmethylated cytosines to uracils. Only primer binding sites protected by methylation of cytosines can support amplification when contacted with primers specific for original primer binding sites. Thus, only original molecules and not copies from the first amplification are subjected to further amplification. The further amplified molecules are then subjected to sequence analysis. Sequences can then be compared from the two aliquots. As in FIG. 5, nucleic acid tags in adapters are not used to distinguish between methylated and unmethylated DNA but to distinguish nucleic acid molecules within the same partition.

V. General Features of the Methods

1. Samples

A sample can be any biological sample isolated from a subject. A sample can be a bodily sample. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof, and urine. A sample can be in the form originally isolated from a subject or can have been subjected to further processing to remove or add components, such as cells, or enrich for one component relative to another. Thus, a preferred body fluid for analysis is plasma or serum containing cell-free nucleic acids. A sample can be isolated or obtained from a subject and transported to a site of sample analysis. The sample may be preserved and shipped at a desirable temperature, e.g., room temperature, 4° C., −20° C., and/or −80° C. A sample can be isolated or obtained from a subject at the site of the sample analysis. The subject can be a human, a mammal, an animal, a companion animal, a service animal, or a pet. The subject may have a cancer. The subject may not have cancer or a detectable cancer symptom. The subject may have been treated with one or more cancer therapy, e.g., any one or more of chemotherapies, antibodies, vaccines or biologics. The subject may be in remission. The subject may or may not be diagnosed of being susceptible to cancer or any cancer-associated genetic mutations/disorders.

The volume of plasma can depend on the desired read depth for sequenced regions. Exemplary volumes are 0.4-40 ml, 5-20 ml, 10-20 ml. For examples, the volume can be 0.5 mL, 1 mL, 5 mL 10 mL, 20 mL, 30 mL, or 40 mL. A volume of sampled plasma may be 5 to 20 mL.

A sample can comprise various amount of nucleic acid that contains genome equivalents. For example, a sample of about 30 ng DNA can contain about 10,000 ($10^4$) haploid human genome equivalents and, in the case of cfDNA, about 200 billion ($2 \times 10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources, e.g., from cells and cell-free of the same subject, from cells and cell-free of different subjects. A sample can comprise nucleic acids carrying mutations. For example, a sample can comprise DNA carrying germline mutations and/or somatic mutations. Germline mutations refer to mutations existing in germline DNA of a subject. Somatic mutations refer to mutations originating in somatic cells of a subject, e.g., cancer cells. A sample can comprise DNA carrying cancer-associated mutations (e.g., cancer-associated somatic mutations). A sample can comprise an epigenetic variant (i.e. a chemical or protein modification), wherein the epigenetic variant associated with the presence of a genetic variant such as a cancer-associated mutation. In some embodiments, the sample comprises an epigenetic variant associated with the presence of a genetic variant, wherein the sample does not comprise the genetic variant.

Exemplary amounts of cell-free nucleic acids in a sample before amplification range from about 1 fg to about 1 µg, e.g., 1 pg to 200 ng, 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, or 200 ng of cell-free nucleic acid molecules. The method can comprise obtaining 1 femtogram (fg) to 200 ng.

Cell-free nucleic acids are nucleic acids not contained within or otherwise bound to a cell or in other words nucleic acids remaining in a sample after removing intact cells. Cell-free nucleic acids include DNA, RNA, and hybrids thereof, including genomic DNA, mitochondrial DNA, siRNA, miRNA, circulating RNA (cRNA), tRNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or a hybrid thereof. A cell-free nucleic acid can be released into bodily fluid through secretion or cell death processes, e.g., cellular necrosis and apoptosis. Some cell-free nucleic acids are released into bodily fluid from cancer cells e.g., circulating tumor DNA, (ctDNA). Others are released from healthy cells. In some embodiments, cfDNA is cell-free fetal DNA (cffDNA) In some embodiments, cell free nucleic acids are produced by tumor cells. In some embodiments, cell free nucleic acids are produced by a mixture of tumor cells and non-tumor cells.

Cell-free nucleic acids have an exemplary size distribution of about 100-500 nucleotides, with molecules of 110 to about 230 nucleotides representing about 90% of molecules, with a mode of about 168 nucleotides and a second minor peak in a range between 240 to 440 nucleotides.

Cell-free nucleic acids can be isolated from bodily fluids through a fractionation or partitioning step in which cell-free nucleic acids, as found in solution, are separated from intact cells and other non-soluble components of the bodily fluid. Partitioning may include techniques such as centrifugation or filtration. Alternatively, cells in bodily fluids can be lysed and cell-free and cellular nucleic acids processed together. Generally, after addition of buffers and wash steps, nucleic acids can be precipitated with an alcohol. Further clean up steps may be used such as silica based columns to remove contaminants or salts. Non-specific bulk carrier nucleic acids, such as $C_ot$-1 DNA, DNA or protein for bisulfite sequencing, hybridization, and/or ligation, may be added throughout the reaction to optimize certain aspects of the procedure such as yield.

After such processing, samples can include various forms of nucleic acid including double stranded DNA, single stranded DNA and single stranded RNA. In some embodiments, single stranded DNA and RNA can be converted to double stranded forms so they are included in subsequent processing and analysis steps.

2. Linking DNA Molecules to Adapters

Double-stranded DNA molecules in a sample and single stranded RNA or DNA molecules converted to double stranded DNA molecules can be linked to adapters at either one end or both ends. Typically, double stranded molecules are blunt ended by treatment with a polymerase with a 5'-3' polymerase and a 3'-5' exonuclease (or proof reading function), in the presence of all four standard nucleotides. Klenow large fragment and T4 polymerase are examples of suitable polymerase. The blunt ended DNA molecules can be ligated with at least partially double stranded adapter (e.g., a Y shaped or bell-shaped adapter). Alternatively, complementary nucleotides can be added to blunt ends of sample nucleic acids and adapters to facilitate ligation. Contemplated herein are both blunt end ligation and sticky end ligation. In blunt end ligation, both the nucleic acid molecules and the adapter tags have blunt ends. In stick-end ligation, typically, the nucleic acid molecules bear an "A" overhang and the adapters bear a "T" overhang.

3. Amplification

Sample nucleic acids flanked by adapters can be amplified by PCR and other amplification methods. Amplification is typically primed by primers binding to primer binding sites in adapters flanking a DNA molecule to be amplified. Amplification methods can involve cycles of denaturation, annealing and extension, resulting from thermocycling or can be isothermal as in transcription-mediated amplification. Other amplification methods include the ligase chain reaction, strand displacement amplification, nucleic acid sequence based amplification, and self-sustained sequence based replication.

Preferably, the present methods performs dsDNA 'T/A ligations' with T-tailed and C-tailed adapters, which result in amplification of at least 50, 60, 70 or 80% of double stranded nucleic acids before linking to adapters. Preferably the present methods increase the amount or number of amplified molecules relative to control methods performed with T-tailed adapters alone by at least 10, 15 or 20%.

4. Tags

Tags comprising barcodes can be incorporated into or otherwise joined to adapters. Tags can be incorporated by ligation, overlap extension PCR among other methods.

Molecular Tagging Strategies

Molecular tagging refers to a tagging practice that allows one to differentiate molecules from which sequence reads originated. Tagging strategies can be divided into unique tagging and non-unique tagging strategies. In unique tagging, all or substantially all of the molecules in a sample bear a different tag, so that reads can be assigned to original molecules based on tag information alone. Tags used in such methods are sometimes referred to as "unique tags". In non-unique tagging, different molecules in the same sample can bear the same tag, so that other information in addition to tag information is used to assign a sequence read to an original molecule. Such information may include start and stop coordinate, coordinate to which the molecule maps, start or stop coordinate alone, etc. Tags used in such methods are sometimes referred to as "non-unique tags". Accordingly, it is not necessary to uniquely tag every molecule in a sample. It suffices to uniquely tag molecules falling within an identifiable class within a sample. Thus, molecules in different identifiable families can bear the same tag without loss of information about the identity of the tagged molecule.

In certain embodiments of non-unique tagging, the number of different tags used can be sufficient that there is a very high likelihood (e.g., at least 99%, at least 99.9%, at least 99.99% or at least 99.999% that all molecules of a particular group bear a different tag. It is to be noted that when barcodes are used as tags, and when barcodes are attached. e.g., randomly, to both ends of a molecule, the combination of barcodes, together, can constitute a tag. This number, in term, is a function of the number of molecules falling into the calls. For example, the class may be all molecules mapping to the same start-stop position on a reference genome. The class may be all molecules mapping across a particular genetic locus, e.g., a particular base or a particular region (e.g., up to 100 bases or a gene or an exon of a gene). In certain embodiments, the number of different tags used to uniquely identify a number of molecules, z, in a class can be between any of $2*z$, $3*z$, $4*z$, $5*z$, $6*z$, $7*z$, $8*z$, $9*z$, $10*z$, $11*z$, $12*z$, $13*z$, $14*z$, $15*z$, $16*z$, $17*z$, $18*z$, $19*z$, $20*z$ or $100*z$ (e.g., lower limit) and any of $100,000*z$, $10,000*z$, $1000*z$ or $100*z$ (e.g., upper limit).

For example, in a sample of about 5 ng to 30 ng of cell free DNA, one expects around 3000 molecules to map to a particular nucleotide coordinate, and between about 3 and 10 molecules having any start coordinate to share the same stop coordinate. Accordingly, about 50 to about 50,000 different tags (e.g., between about 6 and 220 barcode combinations) can suffice to uniquely tag all such molecules. To uniquely tag all 3000 molecules mapping across a nucleotide coordinate, about 1 million to about 20 million different tags would be required.

Generally, assignment of unique or non-unique tags barcodes in reactions follows methods and systems described by US patent applications 20010053519, 20030152490, 20110160078, and U.S. Pat. Nos. 6,582,908 and 7,537,898 and 9,598,731. Tags can be linked to sample nucleic acids randomly or non-randomly.

In some embodiments, the tagged nucleic acids are sequenced after loading into a microwell plate. The microwell plate can have 96, 384, or 1536 microwells. In some cases, they are introduced at an expected ratio of unique tags to microwells. For example, the unique tags may be loaded so that more than about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags are loaded per genome sample. In some cases, the unique tags may be loaded so that less than about 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags are loaded per genome sample. In some cases, the average number of unique tags loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags per genome sample.

A preferred format uses 20-50 different tagbarcodes ligated to both ends of target nucleic acids. For example 35 different tagbarcodes ligated to both ends of target molecules creating 35×35 permutations, which equals 1225 for 35 tagbarcodes. Such numbers of tags are sufficient so that different molecules having the same start and stop points have a high probability (e.g., at least 94%, 99.5%, 99.99%, 99.999%) of receiving different combinations of tags. Other barcode combinations include any number between 10 and 500, e.g., about 15×15, about 35×35, about 75×75, about 100×100, about 250×250, about 500×500.

In some cases, unique tags may be predetermined or random or semi-random sequence oligonucleotides. In other cases, a plurality of barcodes may be used such that barcodes are not necessarily unique to one another in the plurality. In this example, barcodes may be ligated to individual molecules such that the combination of the barcode and the sequence it may be ligated to creates a unique sequence that may be individually tracked. As described herein, detection of non-unique barcodes in combination with sequence data of beginning (start) and end (stop) portions of sequence reads may allow assignment of a unique identity to a particular molecule. The length or number of base pairs, of an individual sequence read may also be used to assign a unique identity to such a molecule. As described herein, fragments from a single strand of nucleic acid having been assigned a unique identity, may thereby permit subsequent identification of fragments from the parent strand.

5. Target Enrichment

In certain embodiments, nucleic acids in a sample can be subject to target enrichment, in which molecules having target sequences are captured for subsequent analysis. Target enrichment can involve use of a bait set comprising oligonucleotide baits labeled with a capture moiety, such as biotin. The probes can have sequences selected to tile across a panel of regions, such as genes. In some embodiments, a bait set can have a higher relative concentration for more specifically desired sequences of interest. Such bait sets are combined with a sample under conditions that allow hybridization of the target molecules with the baits. Then, captured molecules are isolated using the capture moiety. For example, a biotin capture moiety by bead-based streptavidin. Such methods are further described in, for example, U.S. Ser. No. 15/426,668, filed Feb. 7, 2017 (U.S. Pat. No. 9,850,523, issuing Dec. 26, 2017).

6. Sequencing

Sample nucleic acids flanked by adapters with or without prior amplification can be subject to sequencing. Sequencing methods include, for example, Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may multiple lanes, multiple channels, multiple wells, or other mean of processing multiple sample sets substantially simultaneously. Sample processing unit can also include multiple sample chambers to enable processing of multiple runs simultaneously.

The sequencing reactions can be performed on one more forms of nucleic acids at least one of which is known to contain markers of cancer of or other disease. The sequencing reactions can also be performed on any nucleic acid fragments present in the sample. The sequence reactions may provide for sequence coverage of the genome of at least 5%, 10%, 15%, 20%, 25%, 30%, 40%, 50%, 60%, 70%, 80%, 90%, 95%, 99%, 99.9% or 100%. In other cases, sequence coverage of the genome may be less than 5%, 10%, 15%, 20%, 25%, 30%, 40%, 50%, 60%, 70%, 80%, 90%, 95%, 99%, 99.9% or 100%. Sequence coverage can performed on at least 5, 10, 20, 70, 100, 200 or 500 different genes, or at most 5000, 2500, 1000, 500 or 100 different genes.

Simultaneous sequencing reactions may be performed using multiplex sequencing. In some cases, cell-free nucleic acids may be sequenced with at least 1000, 2000, 3000, 4000, 5000, 6000, 7000, 8000, 9000, 10000, 50000, 100,000 sequencing reactions. In other cases cell-free nucleic acids may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases, data analysis may be performed on less than 1000, 2000, 3000, 4000, 5000, 6000, 7000, 8000, 9000, 10000, 50000, 100,000 sequencing reactions. An exemplary read depth is 1000-50000 reads per locus (base).

7. Analysis

The present methods can be used to diagnose presence of conditions, particularly cancer, in a subject, to characterize conditions (e.g., staging cancer or determining heterogeneity of a cancer), monitor response to treatment of a condition, effect prognosis risk of developing a condition or subsequent course of a condition. The present disclosure can also be useful in determining the efficacy of a particular treatment option. Successful treatment options may increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the present methods can be used to monitor residual disease or recurrence of disease.

The types and number of cancers that may be detected may include blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like. Type and/or stage of cancer can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, and abnormal changes in nucleic acid 5-methylcytosine.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers can progress to become more aggressive and genetically unstable. Other cancers may remain benign, inactive or dormant. The system and methods of this disclosure may be useful in determining disease progression.

The present analyses are also useful in determining the efficacy of a particular treatment option. Successful treatment options may increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the present methods can be used to monitor residual disease or recurrence of disease.

The present methods can also be used for detecting genetic variations in conditions other than cancer. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing. Copy number variation or even rare mutation detection may be used to determine how a population of pathogens is changing during the course of infection. This may be particularly important during chronic infections, such as HIV/AIDS or Hepatitis infections, whereby viruses may change life cycle state and/or mutate into more virulent forms during the course of infection. The present methods may be used to determine or profile rejection activities of the host body, as immune cells attempt to destroy transplanted tissue to monitor the status of transplanted tissue as well as altering the course of treatment or prevention of rejection.

Further, the methods of the disclosure may be used to characterize the heterogeneity of an abnormal condition in a subject. Such methods can include, e.g., generating a genetic profile of extracellular polynucleotides derived from the subject, wherein the genetic profile comprises a plurality of data resulting from copy number variation and rare mutation analyses. In some embodiments, an abnormal condition is cancer. In some embodiments, the abnormal condition may be one resulting in a heterogeneous genomic population. In the example of cancer, some tumors are known to comprise tumor cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation and mutation analyses alone or in combination.

The present methods can be used to diagnose, prognose, monitor or observe cancers. or other diseases. In some embodiments, the methods herein do not involve the diagnosing, prognosing or monitoring a fetus and as such are not directed to non-invasive prenatal testing. In other embodiments, these methodologies may be employed in a pregnant subject to diagnose, prognose, monitor or observe cancers or other diseases in an unborn subject whose DNA and other polynucleotides may co-circulate with maternal molecules.

An exemplary method for molecular tag identification of MBD-bead partitioned libraries through NGS is as follows:
1. Physical partitioning of an extracted DNA sample (e.g., extracted blood plasma DNA from a human sample) using a methyl-binding domain protein-bead purification kit, saving all elutions from process for downstream processing.
2. Parallel application of differential molecular tags and NGS-enabling adapter sequences to each partition. For example, the hypermethylated, residual methylation ('wash'), and hypomethylated partitions are ligated with NGS-adapters with molecular tags.
3. Re-combining all molecular tagged partitions, and subsequent amplification using adapter-specific DNA primer sequences.
4. Enrichment/hybridization of re-combined and amplified total library, targeting genomic regions of interest (e.g., cancer-specific genetic variants and differentially methylated regions).
5. Re-amplification of the enriched total DNA library, appending a sample tag. Different samples are pooled, and assayed in multiplex on an NGS instrument.
6. Bioinformatics analysis of NGS data, with the molecular tags being used to identify unique molecules, as well deconvolution of the sample into molecules that were differentially MBD-partitioned. This analysis can yield information on relative 5-methylcytosine for genomic regions, concurrent with standard genetic sequencing/variant detection.

VI. Modes of Practicing the Disclosure

The present disclosure provides a method of comprising partitioning cell-free nucleic acid (cfNA) populations into partitions sharing one or more similar characteristics.

The methods of the present disclosure can be performed to partition single-stranded nucleic acids (ssNA; ssDNA, RNA) and dsDNA, whereby dsDNA molecules are prepared through standard library prep, and ssNA are prepared in an adjunct library prep workflow that converts ssNAs into a form amendable with enrichment, sequencing (e.g., NGS), and analysis, while retaining information about the originating biomolecule type (i.e. RNA, ssDNA, dsDNA).

Approaches in the cfNA-inclusive library preparation can involve (a) converting RNA into an identifiable ssDNA and (b) partitioning ssDNA and dsDNA molecules for parallel NGS library prep, (c) followed by (optional) target enrichment, (d) NGS and downstream data analysis to identify molecule type with sequence (see FIG. 1).

In some embodiments, dsDNA-specific NGS adapter ligation of the cfNA population can be performed prior to RNA molecular tagging, specific-ligation, cDNA conversion, and NGS library prep. Simultaneous sequencing methodology, in which dsDNA, then RNA, is sequentially ligated for NGS library creation, without partitioning, can be applied to cfNA samples as shown in FIG. 2.

In some embodiments, platform ligation uses Y-shaped or 'forked' adapters which produce ligated ds-cfDNA molecules with ssDNA 5' and 3' ends. These ends can be wrongfully ligated by RNA ligase (or Circligase™ II) in simultaneous sequencing or traditional ssDNA library prep methodologies. By altering the ends of the Y-shaped adapters to "hairpins" or "bubbles," the ligated cf-dsDNA molecules no longer have ssDNA ends, and are not a substrate for subsequent ssNA-ligation in simultaneous sequencing/ traditional DNA library prep. Thus, reinventing NGS adapters to contain no free ssDNA ends enables RNA and ssDNA library preparation in addition to a dsDNA workflow, without partitioning of molecule types.

The methods of the present disclosure can be performed on a cfNA population with reverse transcription enzymes using gene specific/random/polyT DNA primers with a molecular tagging tail, subsequently removing the RNA by RNase H or NaOH hydrolysis, yielding a tagged ssDNA (cDNA) to substitute each RNA molecule. Additional methodologies known to those skilled in the art can be employed to remove unwanted RNA sequences, such as ribosomal RNA depletion by selective hybridization.

ssDNA can be selectively captured by NA probes, by omission of standard denaturation step prior to hybridization. The ssDNA-probes hybrids can be isolated from the cfNA population by methods known in the art (e.g., biotinylated DNA/RNA probes, captured by streptavidin-bead magnets). The probe sequences can be target-specific and the same as a panel with a dsDNA workflow, a subset of that workflow, or different (e.g., targeting RNA-fusions at exon-exon junctions, 'hot spot' DNA sequences). Furthermore, all ssNA can be captured in this step, in a sequence-agnostic manner by utilizing probes with 'universal nucleotide bases', such as deoxyinosine, 3-nitropyrrole, and 5-nitroindole.

In addition to genetic variations such as SNV, indels, gene fusions, and CNV, identified by DNA sequencing, epigenetic variations (such as 5-methylcytosine, histone methylation, nucleosome positioning, and micro- and long-noncoding-RNA expression) can lead to or be involved in disease progression, such as cancer. High throughput measurements of epigenetic markers require intricate molecular biology techniques, developed specifically for each type of epigenetic mark. As such, epigenetic sequencing projects are typically parallel from DNA (genetic) sequencing, and require large amounts of input. Phrased differently, multi-analyte biomarker detection is accompanied with sample destruction.

Both genetic (DNA) sequencing and epigenetic sequencing of cell-free DNA has diagnostic value for non-invasive prenatal testing (NIPT) and cancer monitoring/detection. In both applications, the amount of genetic material is limiting and identifying rare molecular events is paramount. Thus, with current methodologies, performing epigenetic sequencing results in a reduction in the sensitivity in detecting genetic variants, as each type of marker requires a dedicated sample.

The present disclosure provides methods of obtaining information on the epigenetic process of DNA 5-methylcytosine, but the "partition with molecular tags" methodology outlined for 5-methylcytosine also can be applied to other epigenetic mechanisms. Similarly, labeling and recovering NGS-adapter ligated parent DNA molecules, as outlined in the present disclosure for 5-methylcytosine (5 mC) identification, also can be used to identify other epigenetic DNA modification marks (e.g., hydroxymethylated, formyl, and carboxyl; 5 hmC, 5fC, and 5caC, respectively).

With respect to 5-methylcytosine, bisulfite-sequencing has been the most popular approach, capable of resolving 5-methylcytosine bases with single-base resolution. This method involves a chemical treatment (bisulfite) that acts on all cytosine bases, converting them to a uracil unless they are 5-methylated or 5-hydroxymethylated. Sequencing following bisulfite treatment will result in 5-methylated cytosines and 5-hydroxymethylated cytosines residues detected as cytosine while unmethylated cytosines, 5-formylmethylated cytosines, and 5-carboxymethylated cytosines are detected as thymine. Variations of bisulfite sequencing, previously described, can further distinguish between 5 mC, 5 hmC, 5fC, and 5caC. The main limitation of this approach is that the majority of the genetic material is lost. The harsh bisulfite treatment degrades <99% of the input DNA, thus reducing the molecular complexity of the sample and the achievable limit of detection. Present molecular biology DNA amplification techniques (e.g., PCR, LAMP, RCA) are agnostic to the 5-methylation status of cytosine, and thus, 5-methylation marks are lost with amplification. This is extremely undesirable in liquid biopsy applications. In addition, with bisulfite-converted DNA libraries detecting somatic variants becomes more challenging (e.g., differentiating a C→T SNV from an unmethylated cytosine). Thus, bisulfite-treated DNA is not used for genetic variant detection in liquid biopsy applications. Performing 5-methylcytosine analysis and genetic variant calling on DNA requires the sample to be split, which reduces input/sensitivity of detection in each workflow and prevents identification of both 5-methylcytosine information and genetic variants on a single molecule.

In certain embodiments, nucleic acids are partitioned based on methylation differences. "Hypermethylation" and "hypomethylation" forms of nucleic acids can be defined as molecules falling above and below, respectively, a particular degree of methylation differentiated by the particular partitioning method used. For example, the partition method may select molecules having at least 2, at least 3, at least 4, at least 5 or at least 6 methylated nucleotides. Extent of methylation refers to number of methylated nucleotides in a nucleic acid fragment. Identifying DNA molecules that are relatively "hypermethylated" in a DNA sample can be achieved by capturing molecules that bind to a methyl-binding domain (MBD) protein, or a fragment or variant thereof. The MBD can also be referred to as a Methyl-CpG-binding domain. The MBD protein can be complexed with magnetic beads. In some embodiments a protein that binds to MBD is MECP2, MBD1, MBD2, MBD3, MBD4, or a fragment or variant thereof. Although the 5-methylation sites are not directly indicated with this method (no bisulfite conversion), bioinformatics analysis of overlapping hypermethylated fragments can resolve specific site(s) of 5-methylcytosine. The main drawback of this method is that by sequencing only the hypermethylated partition, the majority of human genome that is unmethylated (~80-97% by mass) is not sequenced, which prevents/limits identification of genetic variants (e.g., SNV, indels, and CNVs), as these are low coverage regions or not present at all in the hypermethylated partition.

The present disclosure provides methods for obtaining 5-methylcytosine data and for obtaining sequencing data for detection of rare genetic variant in the same low input sample (e.g., a liquid biopsy workflow). For example, an approach comprising MBD fractionation and tagging is non-destructive to nucleic acids in the sample and preserves genome complexity after amplification. In addition, fractionation-tagging approaches (e.g., MBD fractionation and tagging) can recombine differentially partitioned nucleic acid molecules to ensure preservation of genome complexity and enable multi-analyte biomarker detection (genetic and epigenetic variant). By contrast, other approaches may be destructive to nucleic acid molecules in a sample. These other approaches may include bisulfite sequencing, methyl-sensitive restriction enzyme digestion, and MBD enrichment in cases where only one fraction or group of nucleic acid molecules is analyzed (e.g., hypermethylated nucleic acid molecules). For instance, bisulfite sequencing creates physical damage to the nucleic acid molecules. Methyl sensitive restriction enzyme digestion reduces genome complexity by destroying an unmethylated fraction, leaving only methylated nucleic acids intact. MBD enrichment, in instances where only MBD-bound nucleic acid molecules are analyzed, may similarly be used to isolate only a single fraction of nucleic acids in a sample. Approaches analyzing only a single fraction of nucleic acid molecules destroy information about nucleic acid molecules present in a non-enriched portion.

The methods provided herein to obtain 5-methylcytosine data (or other methylation state data) can be practiced in combination with the above-described methods for obtaining single-stranded nucleic acid and double-stranded nucleic acid information. In some embodiments, the methods herein quantify % of hypermethylated DNA by differentially tagging DNA molecules that have been partitioned by MBD-beads to various degrees of methylation. (See FIG. 3). In this method, all eluents from the MBD-partitioning protocol can be recovered and a NGS-library prepared with different sets of molecular tags corresponding to their MBD-partition. Thus, the MBD-partitioning process reduces the loss of material present with typical bisulfite treatment. As the ligated partitions can be re-combined before amplification/enrichment/NGS, there is minimal defect to DNA-sequencing workflows. The MBD binds double-stranded DNA (dsDNA), and thus, MBD-partitioning retains the double-stranded nature of sample DNA, allowing for double-stranded molecular tagging by sensitive DNA sequencing methodologies.

In a MBD-partitioned molecular tag NGS workflow, the molecular tags can serve two purposes—identifying unique DNA molecules from the sample (by combination of tag and genomic start/end coordinates), and indicating the relative 5-methylcytosine level of the molecule. Molecular tags can be used to identify and count unique nucleic acid molecules. This information can be used to calculate amplification imbalances. Molecular tags can allow the original complexity of the sample to be discerned. Molecular tagging can be used to identify and count nucleic acid molecules in a sample even when there is uneven amplification. The above methodology describes physical partitioning by degree of 5-methylcytosine, application of differential molecular tags, optional library re-combine, enrichment, NGS and bioinformatics deconvolution of each molecule originating partition, concurrent with DNA-seq, utilized for genetic sequencing/variant detection. The methodology is extendable to characterizing other epigenetic interactions by substituting the methylation binding protein (MBD) partitioning with different DNA- and protein-binding elements that retain the double-stranded nature of the DNA molecules. For example, antibodies to histones, modified histones, and transcription factors used in various immunoprecipitation protocols can substitute the MBD-partitioning to generate relative information about nucleosome positioning, nucleosome modification, and transcription factor binding associated with every DNA molecule in a sample through the use of differential sets of molecular tags.

Data Analysis

A major challenge faced by cancer methylation analysis in liquid biopsy is cell-type heterogeneity. In addition to inherent and well documented cancer heterogeneity, cell-free DNA in plasma represents mixed cell death type that is predominantly not cancer-related. For example, the cell death can be in a non-malignant organ, physiological hematopoetic lineage. Added to this complexity is that even non-cancer cells in the stromal component are very distinct, e.g. vascular and lymphoid endothelial cells and pericytes, immune cells such as macrophages, leukocytes and lymphocytes, stromal fibroblasts, myofibroblasts, myoepithelial cells, as well as adipose cells, endocrine cells, nerve cells and other cellular and tissue elements that have different developmental origins. Therefore, in some embodiments, adjusting for changes in cell-type composition is carried out when analyzing and interpreting findings from liquid biopsy.

Analysis Pipeline May Involve the Following Steps:
  a) -ome occupancy resolution
  b) Locating dyads, assigning stringency
  c) Fitting Gaussian mixture model within individual genomic elements across whole genome
  d) Deconvolving cell lineages at gene level As an illustrative example, cfDNA fragment start enrichment profile can be separately determined in samples from individual partitions. For example, the partitioned samples may comprise hyper, hypo, or intermediate methylated DNA. The determined cfDNA fragment start enrichment profile can be used to establish nucleosomal occupancy within/relevant regulatory elements, e.g. TSS, enhancer region, distal intergenic elements. For each partition, the occupancy peaks, e.g., dyad, can be determined and their stringency can be assigned. A canonical profile associated with an observed cell state in healthy plasma samples can be established by determining the cfDNA fragment start enrichment profile and locating the dyads in a large non-malignant control (e.g., a sample from a healthy individual or a plurality of healthy individuals). For any sample, Gaussian mixture model can be fit using the canonical profile as defined above to produce residual occupancy corresponding to malignant (non-canonical) chromatin state observed in the partitioned samples, thereby determining non-canonical cfDNA fragment peaks and profiles. The non-canonical cfDNA fragment peaks and profiles may be associated with malignant chromatin state in cancer in each partitioned sample. Biological regulation by methylation can be mediated by a single CpG or by a group of CpGs in close proximity to each other. Therefore, regional analysis of DNA methylation offers a more comprehensive and systematic view of methylation data. Typically, methylation information is summarized over tiling windows or over a set of predefined regions (promoters, CpG islands, introns, and so on).

Figure 9:
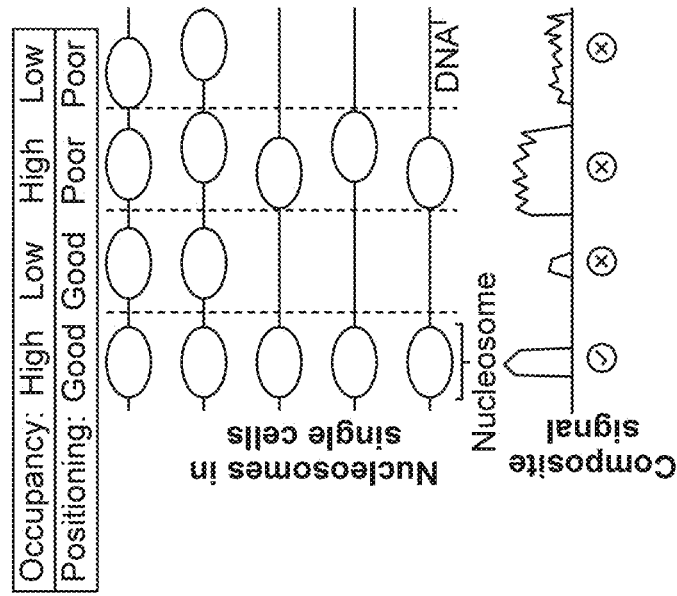
FIG. 9 shows an overview of methodology.

Nucleosome organization can be determined by two independent metrics, such as nucleosome occupancy and nucleosome positioning. Nucleosome occupancy can be understood as the probability of a nucleosome being present over a specific genomic region within a population of cells. Nucleosome occupancy can be measured in sequencing-based experiments as coverage (number of aligned sequencing reads mapped to the genomic region). Nucleosome positioning can be the probability of a nucleosome reference point (for example, a dyad) being at a specific genomic coordinate relative to surrounding coordinates. As shown in FIG. 9, good nucleosome positioning can be biologically interpreted as a nucleosome dyad occurring at the same genomic coordinate every time it is present. Poor positioning can be interpreted as a nucleosome dyad occupying a range of positions within the same general footprint of an entire nucleosome. In one example, samples from 8 subjects with lung cancer were used to determine dyad centers. Nucleosome positioning and nucleosome occupancy were determined. For example, high occupancy and good positioning may be indicated when coverage is >0.5 Quantile (Qu) and width of peak is <0.5 Qu. In some instances, distance between dyad centers in fractionated samples (such as hyper-/hypomethylated fractions) can be compared with unfractionated (no MBD). In some cases, dyad centers as well as adjacent chromatin structures can be resolved by assigning dyads centers to all peaks with occupancy to all peaks with occupancy coverage above 5% across the genome. The occupancy coverage can be 15%, 20%, 25% or 30%. The occupancy coverage can be assigned using machine learning approaches by determining peak location, width, length, center and width resolution. This provides an empirical resolution of chromatin architecture for plasma DNA.

An increase in coverage of sequence reads may be correlated with greater nucleosome occupancy. Further, the nucleosome occupancy may be inversely related to nucleosome-depleted region (NDR). The increase in nucleosome occupancy may indicate altered chromatin structure, such as more compacted chromatin. The compacted chromatin may be indicative of downregulation of gene expression that may perturb normal cell functioning. Perturbation in normal cell functioning can serve as an indication of diseases, such as cancer.

Cell-free DNA comprises signal from a heterogeneous population of cells (e.g. dying, malignant, non-malignant, etc.). Heterogeneous population of cells can have nucleic acids with multiple chromatin states. In some instances, the multiple chromatin states can include different states of nucleosome occupancy, such as well-positioned or dispersed ("fuzzy") nucleosomes. The well-positioned nucleosomes show greater coverage while fuzzy nucleosomes show lower coverage of sequence reads. Based on coverage of sequence reads, nucleosome occupancy across chromatin can be resolved.

"Deconvolution" can refer to the process of decomposing cell-free DNA fragment occupancy peaks that overlap with each other, thus extracting information about the "hidden peak". Deconvolution of nucleosome occupancy peaks can be achieved by MBD partitioning. Partitioning nucleic acids into hypermethylated and hypomethylated partitions can produce two distinct peaks, peak 1 and peak 2. However, when the nucleic acids are not fractionated, one continuous peak can be obtained and deconvolving malignancy-associated peak 1 from nonmalignant peak 2 may not be feasible.

Dyads can be DNA regions occupied by the center of nucleosome. Dyads can be located in partitioned samples. In some cases, nucleic acids are partitioned into hyper- and hypo-methylated fraction. Dyad positioning or localization can be performed using reference-free method or reference based method. Reference-free method can include in silico combining of both hyper and hypo partitions to determine underlying dyad position, thereby determining dyad map. In some cases, sequencing data from hyper- and hypo-methylated partitions are combined to determine nucleosome occupancy and are compared between the partitions, e.g., combine signal from all partitions and detect occupancy peaks, then compare locations of those seen in hyper vs hypo. Reference-based method can include independent analysis of partitions. For example, nucleosome occupancy for hyper- and hypomethylated fractions are determined. The nucleosome occupancy for each partition in a first experiment can be used for corresponding partition in subsequent experiments(s). where the same part 1 is done independently on a large set of samples (standard WGS would suffice since partition-based information is not used and information is combined to improve peak resolution) and the map of occupancy peaks is stored as a "reference" against each a single partition (or both) can be compared.

Fragmentome Signatures Based on Fragmentomic Data

Methods of examining fragmentome data are described in, for example, U.S. publication 2016/0201142 (Lo), WO 2016/015058 (Shendure) and PCT/US17/40986, filed Jul. 6, 2017 ("Methods For Fragmentome Profiling Of Cell-Free Nucleic Acids"), all incorporated herein by reference. Fragmentomic data refer to sequence data obtained by analyzing nucleic acid fragments. For example, the sequence data can include fragment length (in base pairs), genomic coordinates (e.g., start and stop locations on reference genome), coverage (e.g., number of copies) or sequence information (e.g., bases A, G, C, T). Fragmentomic data refer to sequence information of fragment starts and stops and associated occupancy in cell-free DNA corresponding to enrichment of protected content of cell-free DNA observed in blood or plasma.

For example, one could determine, in a sample, the number of cfDNA molecules having their center point mapping to particular nucleotide coordinates across the genome or a target portion thereof. In a healthy individual, this would typically produce a wavy graph in which the peaks of the graph represent nucleosome positions (e.g., where cellular DNA is not cleaving during conversion to cfDNA), and the troughs represent inter-nucleosome positions (e.g., at which many molecules are cleaved and hence, few molecules are centered there). The distance between peaks represents nucleosome dyads. In malignant cells, the positions of nucleosomes may shift, e.g., as a function of methylation. In this case, one expects a shift in the positions of peaks and troughs in the graph. Such shifts can be more easily detected by partitioning molecules based on different characteristics, and examining fragment distribution for each partition. The fragment data can be further analyzed in one or a plurality of more dimensions. For example, at any coordinate, the number of molecules mapping to it can be further differentiated based on fragment size. In a graph based on such data, a third, "Z" dimension, represents fragment size. So, for example, in a two-dimensional graph, the X axis represents genomic coordinate and the Y axis represents number of molecules mapping to the coordinate. In a three-dimensional graph, the X axis represents genomic coordinate, the Z dimension represents fragment length, and the Y axis represents number of molecules of each size mapping to the coordinate. Such a three-dimensional graph can be represented as a two-dimension heat map, in which the X and Z axes are displayed in the two dimensions and the value on the Y axis is represented by, e.g., color intensity (e.g., darker representing greater values) or "hotness" of color (e.g., blue representing lower values and red representing higher values). Such data can be mined to determine nucleosome position patterns characteristic of a state being examined, such as presence or absence of cancer, type of cancer, degree of metastasis, etc.

Cohorts of individuals may all have a shared characteristic. This shared characteristic may be selected from the group consisting of: a tumor type, an inflammatory condition, an apoptotic condition, a necrotic condition, a tumor recurrence, and resistance to a treatment. In some instances, a cohort comprises individuals having a specific type of cancer (e.g., breast, colorectal, pancreatic, prostate, melanoma, lung or liver). To obtain the nucleosome signature of a cancer, an individual suffering from the cancer provides a blood sample. Cell-free DNA is obtained from the blood sample. The cell-free DNA is sequenced (either with or without selective enrichment of a set of regions from the genome). Sequence information in the form of sequence reads from the sequencing reactions are mapped to the human reference genome. In some embodiments, molecules are collapsed into unique molecule reads either before or after the mapping operation.

Since cell-free DNA fragments in a given sample represent a mix of cells from which the cell-free DNA arose, the differential nucleosomal occupancy from each cell type may result in a contribution toward the mathematical model representative of a given cell-free DNA sample. For example, a distribution of fragment lengths may have arisen due to differential nucleosomal protection across different cell types, or across tumor vs. non-tumor cells. This method may be used to develop a set of clinically useful assessments based on the uni-parametric, multi-parametric, and/or statistical analysis of sequence data.

Nucleic acid molecules in a sample may be fractionated based on one or more characteristics. Fractionation may include physically partitioning nucleic acid molecules into subsets or groups based on the presence or absence of a genomic characteristic. Fractionation may include physically partitioning nucleic acid molecules in groups based on the degree to which a genomic characteristic is present. A sample may be fractionated or partitioned into one or more groups based on a characteristic that is indicative of differential gene expression or a disease state. A sample may be fractionated based on a characteristic that provides a difference in signal between a normal and diseased state during analysis of nucleic acids, e.g., cfDNA, non-cfDNA, tumor DNA, circulating tumor DNA (ctDNA).

Fragmentomic data may be used to infer genetic variants. Genetic variants include copy number variation (CNV), insertion and/or deletion (indel), single nucleotide variation (SNV) and/or gene fusion. Fragmentomic data may be used to infer epigenetic variants, such as variants indicative of cancer. One or more genetic variants in each fractionated or partitioned group and/or unfractionated nucleic acids may be determined. Fractionation or partitioning can be performed based on at least one of the various characteristics including but are not limited to methylation status, size, length, and transcription binding of nucleic acids. Genetic variants determined in fractionated or partitioned groups may be compared among each other and/or with unfractionated nucleic acids that may or may not possess the same characteristics. Fractionated or partitioned nucleic acids can be recombined and the fragmentomics data can be compared with unfractionated nucleic acids and/or nucleic acids that do not possess the same characteristics as the fractionated or partitioned nucleic acids to determine a presence of genetic variants.

Models may be used in a panel configuration to selectively enrich regions (e.g., fragmentome profile associated regions) and ensure a high number of reads spanning a particular mutation, important chromatin-centered events like transcription start sites (TSSs), promoter regions, junction sites, and intronic regions may also be considered.

In one example, differences in fragmentome profiles are found at or near junctions (or boundaries) of introns and exons. Identification of one or more somatic mutations may be correlated with one or more multi-parametric or uni-parametric models to reveal genomic locations where cfDNA fragments are distributed. This correlation analysis may reveal one or more intron-exon junctions where fragmentome profile disruptions are most pronounced.

Figure 17:
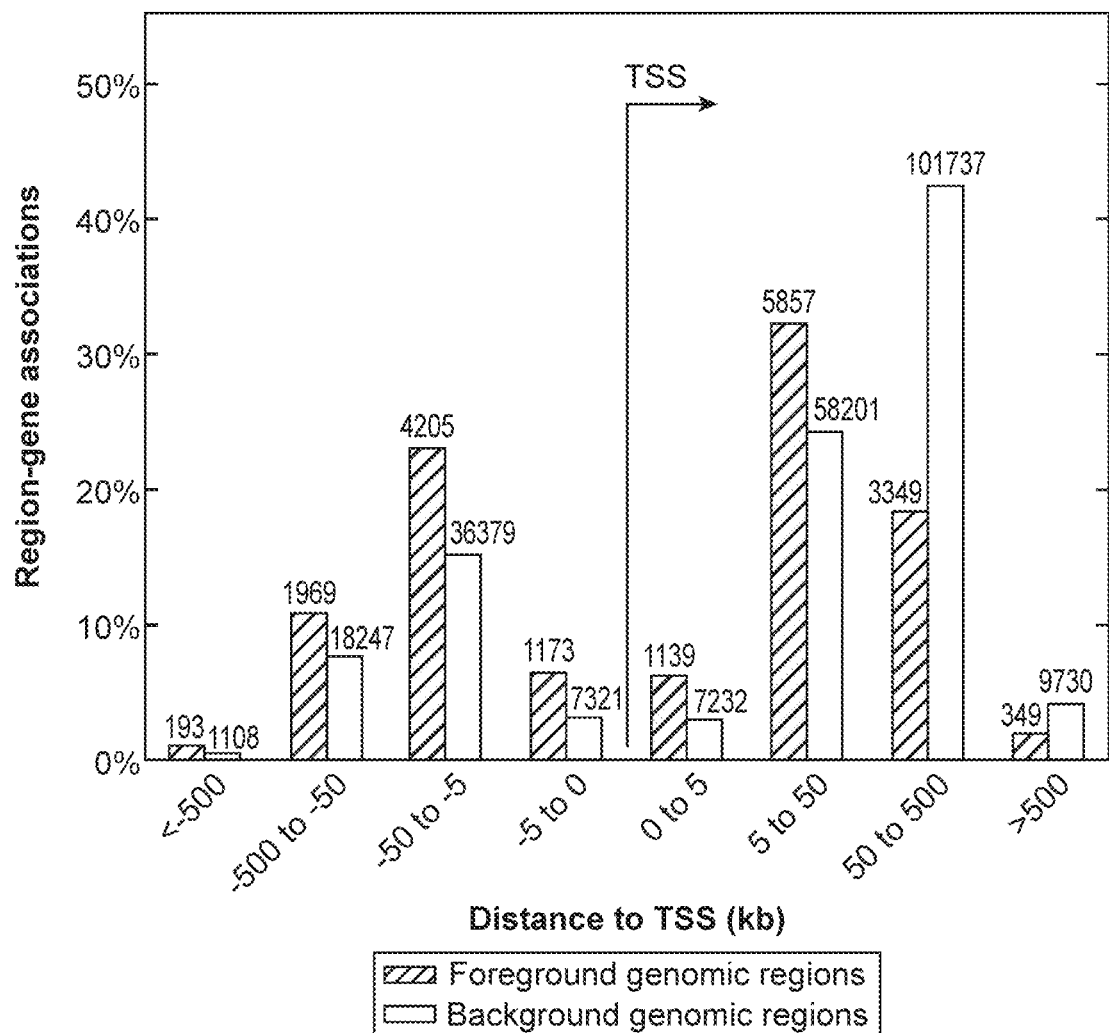
FIG. 17 displays statistics about the association of input genomic regions to the TSS of all the genes putatively regulated by the genomic regions. X-axis indicate distance to TSS in kilo bases (kb) while Y-axis indicate region-gene association in percentage (%). Above each bar in the graph, an absolute number of items being counted is listed. Foreground genomic regions, represented by dark bar, were selected from a superset of Background genomic regions, indicated by light bar. The background genomic regions were repetitive elements that have been co-opted into functional roles selected from all repetitive elements in the genome.

As another example, hypermethylation in the sample can be observed in regions farther from TSS. Enrichment of hypermethylated regions can be observed in a distance between 0 kb and 5 kb, 5 kb and 50 kb, and/or 50 kb and 500 kb from the TSS. Enrichment of hypermethylated regions can be observed between 5 kb and 50 kb from the TSS. Enrichment of hypermethylated regions can be observed less than 5 kb, 10 kb, 15 kb, 20 kb, 25 kb, 30 kb, 35 kb, 40 kb, 50 kb, 100 kb, 200 kb, 300 kb, 400 kb, and/or 500 kb from the TSS. Enrichment of hypermethylated regions can be observed more than 5 kb, 10 kb, 15 kb, 20 kb, 25 kb, 30 kb, 35 kb, 40 kb, 50 kb, 100 kb, 200 kb, 300 kb, 400 kb, and/or 500 kb from the TSS. The position and enrichment of hypermethylation can vary between DNA obtained from a healthy or normal subject (normal DNA) and DNA obtained from a diseased subject. For example, DNA from a subject suspected of having or having lung cancer (lung cancer DNA) may show enrichment of farthest hypermethylated distance from canonical locations in TSS and well-positioned nucleosomes in hypermethylated fraction occupy the vicinity of promoter region (FIG. 17). For example, unfractionated nucleic acids (no MBD) from a lung cancer patient were used for sequencing. Based on fragmentomic data, such as genomic location, nucleosome dyad centers were determined for the sequence reads. Further based on fragmentomic data, sequence reads that have coverage less than or equal to 5% or coverage less than or equal to 95% were further analyzed. Gene annotation tools, such as Genomic Regions Enrichment of Annotations Tool (GREAT) were used to assign functionality to a set of genomic regions based on nearby genes. The distance between sequence reads and their putatively regulated genes were determined (FIG. 17). The distances were divided into four separate bins: one from 0 to 5 kb, another from 5 kb to 50 kb, a third from 50 kb to 500 kb, and a final bin of all associations over 500 kb. For preciseness, the bins are [0, 5 kb], [5 kb, 50 kb], [50 kb, 500 kb], [500 kb, Infinity]. In the graph, all associations precisely at 0 (i.e. on the TSS) were split evenly between the [−5 kb, 0] and [0, 5 kb] bins. Using this method, hypermethylation in the sample was observed in regions farther from TSS in both the background genomic regions (e.g., all nucleosomes) and the foreground genomic regions (e.g., methylated nucleosomes). For example, enrichment of hypermethylated regions was observed between [5 kb, 50 kb] bin.

Fragmentome signature may assist in determining nucleosome occupancy, nucleosome positioning, RNA Polymerase II pausing, cell death-specific DNase hypersensitivity, and chromatin condensation during cell death. Such a signature may also provide insight into cell debris clearance and trafficking. For example, cell debris clearance can involve DNA fragmentation carried out by caspase-activated DNase (CAD) in cells dying by apoptosis, but also may be carried out by lysosomal DNase II after the dying cells are phagocytosed, resulting in different cleavage maps.

Genome partitioning maps can be constructed by genome wide identification of differential chromatin states in malignant vs non-malignant conditions associated with aforementioned properties of chromatin via aggregation of significant windows into regions of interest. Such regions of interest are generally referred to as genome partitioning maps.

Fractionation Based on Methylation Status

The nucleic acid molecules in a sample can be fractionated based on the characteristic of 5-methylcytosine. The DNA can be methylated at cytosine such as in CpG dinucleotide regions. DNA methylation along with histone complexes may influence DNA packaging into chromatin as well epigenetic regulation of gene expression. Epigenetic alterations may play a crucial role in various diseases, such as in all steps of cancer progression, initiation of primary or early stage cancer, relapsed or metastatic cancer. For example, hypermethylation of a normally hypomethylated region, such as transcription start site (TSS) of genes involved in normal growth, DNA repair, cell cycle regulation and cell differentiation, may be indicative of cancer. The hypermethylation may alter gene expression by repressing transcription. In some cases, hypermethylation may reduce and/or repress gene expression. For example, hypermethylation may reduce and/or repress expression of an oncogene repressor. In some cases, hypermethylation may increase and/or promote gene expression. For example, hypermethylation of a suppressor may result in increased and/or promoted gene expression of a downstream responder, e.g., an oncogene that is normally suppressed by suppressor.

Based on DNA methylation status, the nucleic acid molecules in a sample can be fractionated into different groups that can enrich nucleic acid molecules with similar methylation status using experimental procedures. For example, a methyl-binding domain (MBD) protein can be used to affinity purify the nucleic acid molecules with similar status of methylation, such as hypermethylation, hypomethylation and residual methylation. In another example, an antibody specific for 5-methyl-cytosine can be used to immunoprecipitate the nucleic acid molecules with similar levels of methylation. In another example, bisulfite-based methods can be employed to selectively enrich highly methylated nucleic acid molecules. In yet another example, a methylation sensitive restriction enzyme can be used to selectively enrich highly methylated nucleic acid molecules.

Upon fractionation using one of the characteristics, the nucleic acid molecules in each group may be sequenced to generate sequence reads. The sequence reads may be mapped to a reference genome. Mapping can generate sequence information. Sequence information may be analyzed to determine genetic variations, including, for example, single nucleotide variants, copy number variations, indels, or fusions. In instances where cell-free DNA is assayed using the methods disclosed herein may generate fragmentomic data, which may vary between groups of fractionated nucleic acid molecules. Fragmentomic data may include genomic coordinates, size, coverage or sequence information. The disclosure provides methods for integrating the fragmentomic data with sequence reads from each of the partitions. Such integration may be useful in accurate and rapid detection of biomarkers indicative of a disease status.

The methods described herein can be used to enrich nucleic acid molecules in silico based on fragmentomic data. For example, unfractionated nucleic acid molecules (no MBD) from a lung cancer patient can be used for sequencing. In another example, fractionation can be achieved based on a difference in a mono-nucleosomal or a dinucleosomal profile alone or in combination with other characteristics such as size and/or methylation status. The mono-nucleosomal profile can refer to the coverage or counts of fragments that are approximately of length required to wrap around a single nucleosome (e.g., about 146 bp). The dinucleosomal profile can refer to the coverage or counts of fragments that are approximately of length required to wrap around a single nucleosome twice (e.g., about 292 bp).

Data Analysis

In certain embodiments, data from different classes of subjects, e.g., cancer/cancer-free, cancer type 1/cancer type 2, can be used to train a machine learning algorithm to classify a sample as belonging to one of the classes. The term "machine learning algorithm," as used herein, refers to an algorithm, executed by computer, that automates analytical model building, e.g., for clustering, classification or pattern recognition. Machine learning algorithms may be supervised or unsupervised. Learning algorithms include, for example, artificial neural networks (e.g., back propagation networks), discriminant analyses (e.g., Bayesian classifier or Fischer analysis), support vector machines, decision trees (e.g., recursive partitioning processes such as CART—classification and regression trees), random forests), linear classifiers (e.g., multiple linear regression (MLR), partial least squares (PLS) regression and principal components regression (PCR)), hierarchical clustering and cluster analysis. A dataset on which a machine learning algorithm learns can be referred to as "training data".

The term "classifier," as used herein, refers to algorithm computer code which, receives, as input, test data and produces, as output, a classification of the input data as belonging to one or another class.

The term "dataset," as used herein, refers to a collection of values characterizing elements of a system. A system may be, for example, cfDNA from a biological sample. Elements of such a system may be genetic loci. Examples of a dataset (or "data set") include values indicating a quantitative measure of a characteristic selected from: (i) DNA sequences mapping to a genetic locus, (ii) DNA sequences starting at a genetic locus, (iii) DNA sequences ending at a genetic locus; (iv) a dinucleosomal protection or mono-nucleosomal protection of a DNA sequence; (v) DNA sequences located in an intron or exon of a reference genome; (vi) a size distribution of DNA sequences having one or more characteristics; (vii) a length distribution of DNA sequences having one or more characteristics, etc.

The term "value," as used herein, refers to an entry in a dataset can be anything that characterizes the feature to which the value refers. This includes, without limitation, numbers, words or phrases, symbols (e.g., + or −) or degrees.

Digital Processing Device

In some embodiments, the methods described herein utilize a digital processing device. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, handheld computers, Internet appliances, mobile smartphones, and tablet computers.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 32:
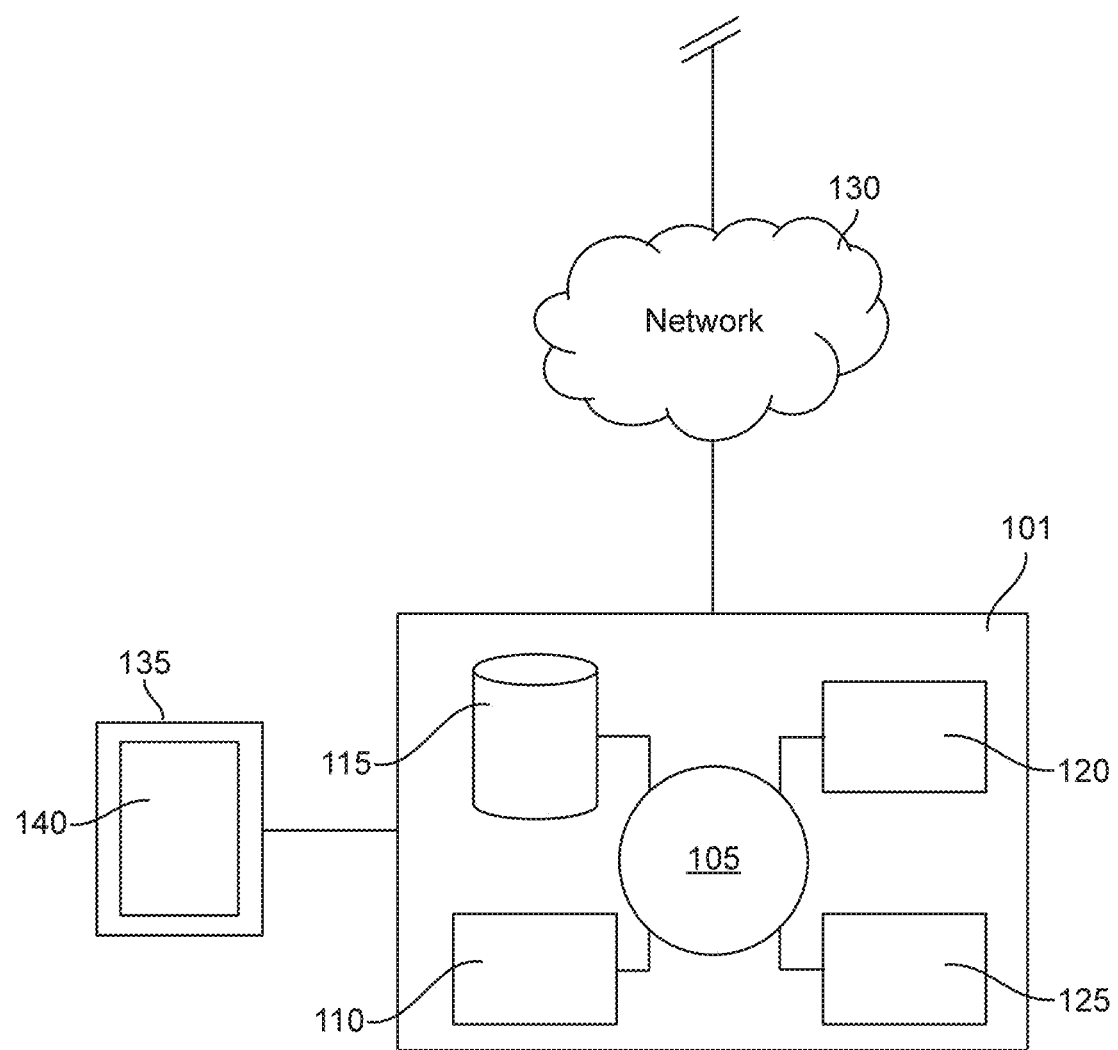
FIG. 32 shows an embodiment of a digital processing device

Referring to FIG. 32, in a particular embodiment, an exemplary digital processing device 101 is programmed or otherwise configured to analyze, assay, decode and/or deconvolute sequence and/or tag data. In the embodiment, the digital processing device 101 includes a central processing unit (CPU, also "processor" and "computer processor" herein) 105, which can be a single core or multi core processor, or a plurality of processors for parallel processing. The digital processing device 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The digital processing device 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the device 101, can implement a peer-to-peer network, which may enable devices coupled to the device 101 to behave as a client or a server.

Continuing to refer to FIG. 32, the CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and write back. The CPU 105 can be part of a circuit, such as an integrated circuit. One or more other components of the device 101 can be included in the circuit. In some cases, the circuit is an application specific integrated circuit (ASIC) or a field programmable gate array (FPGA).

Continuing to refer to FIG. 32, the storage unit 115 can store files, such as drivers, libraries and saved programs. The storage unit 115 can store user data, e.g., user preferences and user programs. The digital processing device 101 in some cases can include one or more additional data storage units that are external, such as located on a remote server that is in communication through an intranet or the Internet.

Continuing to refer to FIG. 32, the digital processing device 101 can communicate with one or more remote computer systems through the network 130. For instance, the device 101 can communicate with a remote computer system of a user. Examples of remote computer systems include personal computers (e.g., portable PC), slate or tablet PCs (e.g., Apple® iPad, Samsung® Galaxy Tab, and Microsoft® Surface®), and smartphones (e.g., Apple® iPhone or Android-enabled device).

Methods as described herein can be at least partially implemented by way of machine (e.g., computer processor) executable code stored on an electronic storage location of the digital processing device 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

Non-Transitory Computer Readable Storage Medium

In some embodiments, the methods disclosed herein utilize one or more non-transitory computer readable storage media encoded with a program including instructions executable by an operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Executable Instructions

In some embodiments, the methods disclosed herein utilize instructions which are executable by a digital processing device, in the form of at least one computer program. For example, a computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program comprises a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 33:
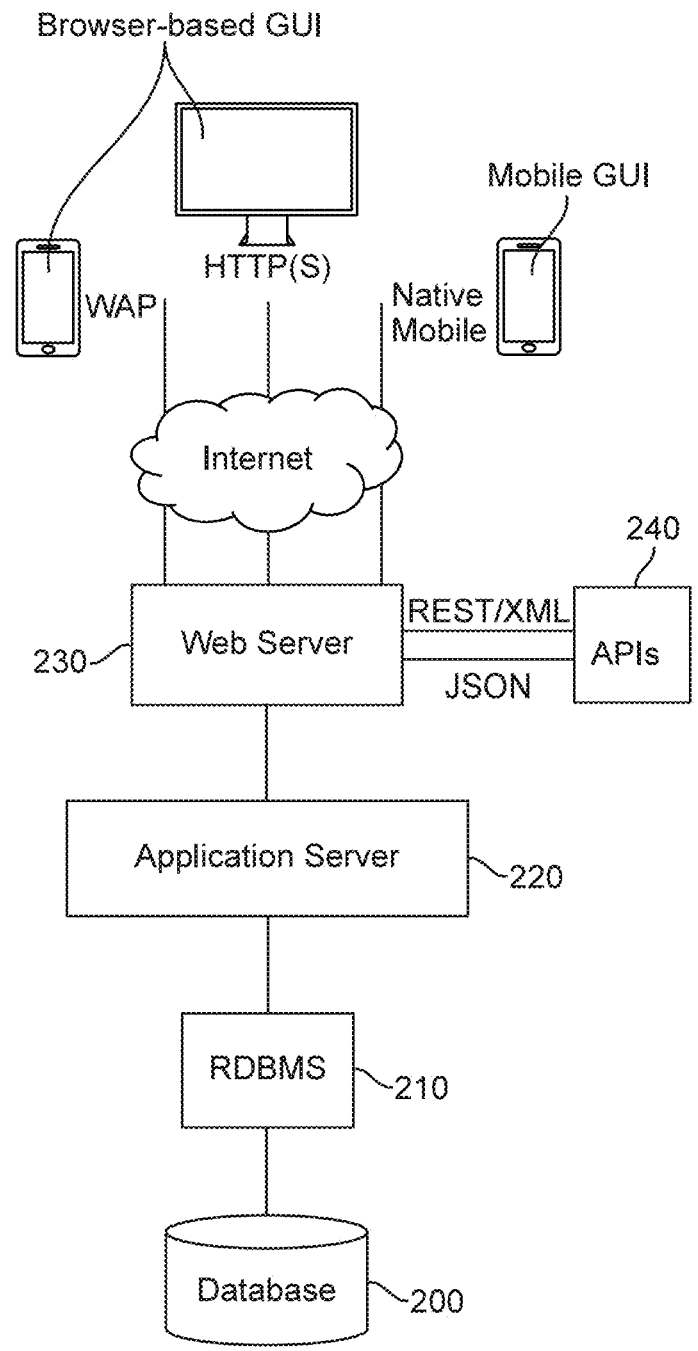
FIG. 33 shows an embodiment of an application provision system

Referring to FIG. 33, in a particular embodiment, an application provision system comprises one or more databases 200 accessed by a relational database management system (RDBMS) 210. Suitable RDBMSs include Firebird, MySQL, PostgreSQL, SQLite, Oracle Database, Microsoft SQL Server, IBM DB2, IBM Informix, SAP Sybase, Teradata, and the like. In this embodiment, the application provision system further comprises one or more application severs 220 (such as Java servers, .NET servers, PHP servers, and the like) and one or more web servers 230 (such as Apache, IIS, GWS and the like). The web server(s) optionally expose one or more web services via app application programming interfaces (APIs) 240 via a network, such as the Internet, the system provides browser-based and/or mobile native user interfaces.

Figure 34:
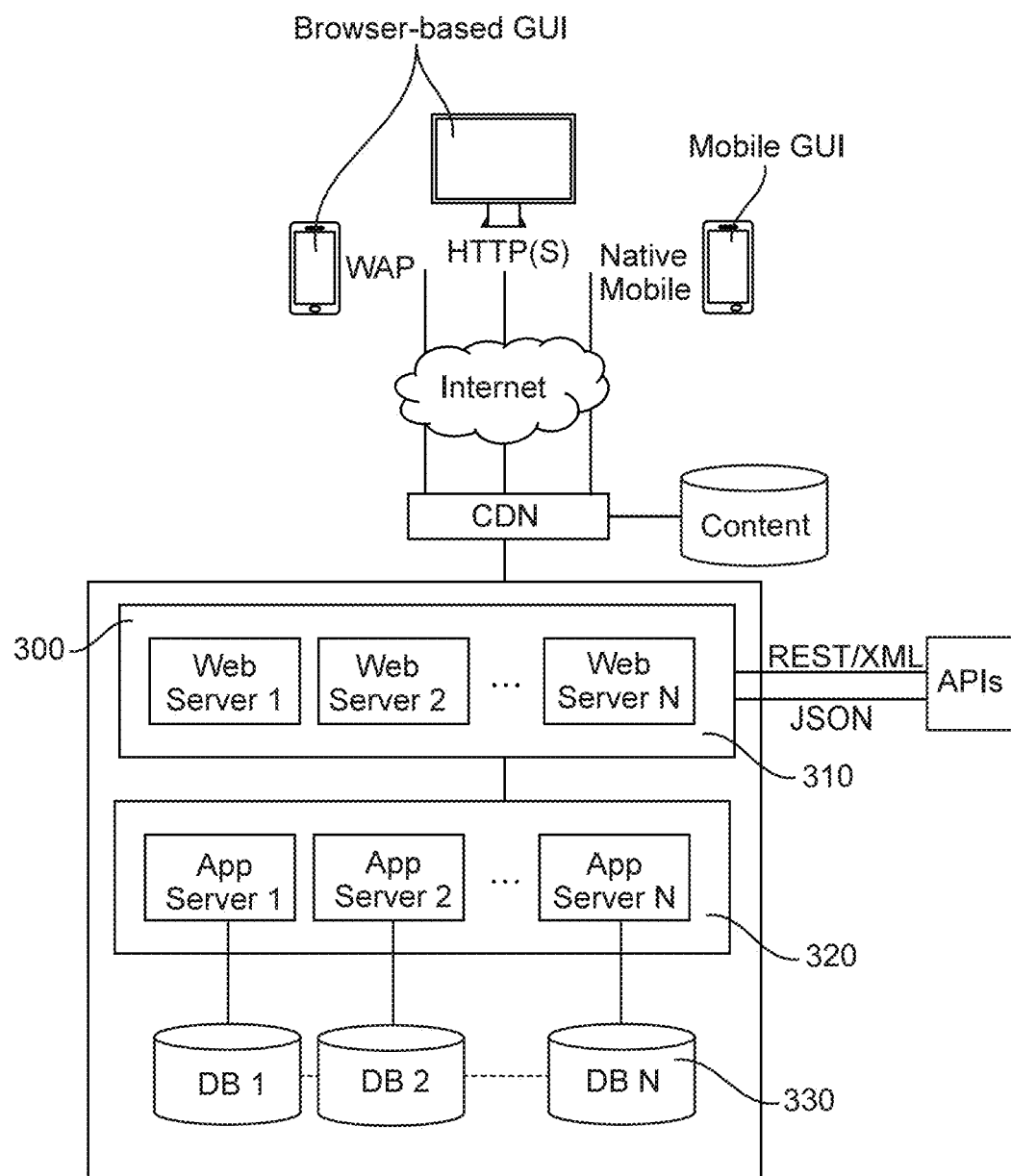
FIG. 34 shows an embodiment of an application provision system employing a cloud-based architecture.

Referring to FIG. 34, in a particular embodiment, an application provision system alternatively has a distributed, cloud-based architecture 300 and comprises elastically load balanced, auto-scaling web server resources 310 and application server resources 320 as well synchronously replicated databases 330.

Mobile Application

In some embodiments, a computer program comprises a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and PhoneGap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable compiled applications.

Software Modules

In some embodiments, the methods disclosed herein utilize software, server, and/or database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the methods disclosed herein utilize one or more databases. In view of the disclosure provided herein, those of skill in the art will recognize that many databases are suitable for storage and retrieval of patient, sequence, tag, code/decode, genetic variant, and disease information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

In one aspect provided herein is a system comprising a computer comprising a processor and computer memory, wherein the computer is in communication with a communications network, and wherein computer memory comprises code which, when executed by the processor, (1) receives sequence data into computer memory from the communications network; (2) determines whether a genetic variant in the sequence data represents a germline mutant or a somatic cell mutant, using the methods described herein; and (3) reports out, over the communications network, the determination.

The communications network can be any available network that connects to the internet. The communications network can utilize, for example, a high-speed transmission network including, without limitation, Broadband over Powerlines (BPL), Cable Modem, Digital Subscriber Line (DSL), Fiber, Satellite, and Wireless.

In one aspect provided herein is a system comprising: a local area network; one or more DNA sequencers comprising computer memory configured to store DNA sequence data which are connected to the local area network; a bioinformatics computer comprising a computer memory and a processor, which computer is connected to the local area network; wherein the computer further comprises code which, when executed, copies DNA sequence data stored on a DNA sequencer, writes the copied data to memory in the bioinformatics computer, and performs steps as described herein.

Also provided herein are numerous systems for implementing the described methods. In some embodiments the systems comprise a nucleic acid sequencer, including next generation DNA sequencers, the sequencer is in data communication with a digital processing device, wherein data received by a software module or modules on the digital processing device is generated by the sequencer when the sequencer obtains DNA sequence information from partitioned and tagged DNA sequence that have been partitioned and tagged by the subject methods. The sequencer and the digital processing device do not need to be located near each other, and in some embodiments may separated over great physical distances, provided suitable data communications exist between the system components. The specific system embodiments described below are exemplary of the larger variety of systems provided by the invention. It will be understood by those skilled in the art that the method described herein that comprise data analysis step may be readily implemented though systems disclosed herein, wherein a software module or modules on a digital processing device is used to analyze sequence data obtained by sequencing tagged nucleic acid populations produced by the subject methods.

An embodiment is a system comprising:
a nucleic acid sequencer: a digital processing device comprising at least one processor, an operating system configured to perform executable instructions, and a memory; and
a data link communicatively connecting the nucleic acid sequencer and the digital processing device; wherein the digital processing device further comprises instructions executable to create an application for analyzing a nucleic acid population comprising at least two forms of nucleic acid selected from: double-stranded DNA, single-stranded DNA and single-stranded RNA, each of the at least two forms comprising a plurality of molecules, the application comprising: (i) a software module receiving sequence data from the nucleic acid sequencer via the data link, the sequence data of amplified nucleic acids at least some of which are tagged, the sequence data generated by linking at least one of the forms of nucleic acid with at least one tagged nucleic acid to distinguish the forms from one another, amplifying the forms of nucleic acid at least one of which is linked to at least one nucleic acid tag, wherein the nucleic acids and linked nucleic acid tags are amplified to produce amplified nucleic acids of which those amplified from the at least one form are tagged; and (ii) a software module assaying the sequence data of the amplified nucleic acids by obtaining sequence information sufficient to decode the tagged nucleic acid molecules of the amplified nucleic acids to reveal the forms of nucleic acids in the population providing an original template for the amplified nucleic acids linked to the tag nucleic acid molecules for which sequence data has been assayed. In another embodiment, the system further comprises a software module decoding the tagged nucleic acid molecules of the amplified nucleic acids to reveal the forms of nucleic acids in the population providing an original template for the amplified nucleic acids linked to the tag nucleic acid molecules for which sequence data has been assayed. In other another embodiment of a system, the application further comprises a software module transmitting a result of the assay via a communications network.

Another embodiment is a system comprising: a next-generation sequencing (NGS) instrument;
a digital processing device comprising at least one processor, an operating system configured to perform executable instructions, and a memory; and a data link communicatively connecting the NGS instrument and the digital processing device; wherein the digital processing device further comprises instructions executable to create an application comprising: (i) a software module for receiving sequence data from the NGS instrument via the data link, the sequence data generated by physically fractionating DNA molecules from a human sample to generate two or more partitions, applying differential molecular tags and NGS-enabling adapters to each of the two or more partitions to generate molecular tagged partitions, and assaying the molecular tagged partitions with the NGS instrument; (ii) a software module for generating sequence data for deconvoluting the sample into molecules that were differentially partitioned; and (iii) a software module for analyzing the sequence data by deconvoluting the sample into molecules that were differentially partitioned. In other another embodiment of a system, the system further comprises a software module transmitting a result of the assay via a communications network.

Another embodiment is a system comprising: a next-generation sequencing (NGS) instrument; a digital processing device comprising at least one processor, an operating system configured to perform executable instructions, and a memory; and a data link communicatively connecting the NGS instrument and the digital processing device; wherein the digital processing device further comprises instructions executable by the at least one processor to create an application for molecular tag identification of MBD-bead fractionated libraries comprising: a software module configured to receive sequence data from the NGS instrument via the data link, the sequence data generated by physically fractionating an extracted DNA sample using a methyl-binding domain protein-bead purification kit, saving all elutions for downstream processing; conducting parallel application of differential molecular tags and NGS-enabling adapter sequences to each fraction or group; re-combining all molecular tagged fractions or groups, and subsequent amplification using adapter-specific DNA primer sequences; conducting enrichment/hybridization of re-combined and amplified total library, targeting genomic regions of interest; re-amplifying the enriched total DNA library, appending a sample tag; pooling different samples; and assaying them in multiplex on the NGS instrument; wherein NGS sequence data produced by the instrument provides sequence of the molecular tags being used to identify unique molecules, and sequence data for deconvolution of the sample into molecules that were differentially MBD-partitioned; and (ii) a software module configured to perform analysis of the sequence data by using the molecular tags to identify unique molecules and deconvoluting the sample into molecules that were differentially MBD-partitioned. Another embodiment is a system wherein the application further comprises a software module configured to transmit a result of the analysis via a communications network.

Another embodiment is a system comprising: (a) A next generation sequencing (NGS) instrument (b) a digital processing device comprising at least one processor, an operating system configured to perform executable instructions, and a memory; and (c) a data link communicatively connecting the NGS instrument and the digital processing device; wherein the digital processing device further comprises instructions executable to create an application comprising: i) a software module for receiving sequence data from the NGS instrument via the data link, the sequence data generated loaded with labeled nucleic acids prepared by contacting the nucleic acid population with an agent that preferentially binds to nucleic acids bearing the modification, separating a first pool of nucleic acids bound to the agent from a second pool of nucleic acids unbound to the agent, wherein the first pool of nucleic acids is overrepresented for the modification, and the nucleic acids in the second pool are underrepresented for the modification; linking the nucleic acids in the first pool and/or second pool to one or more nucleic acid tags that distinguish the nucleic acids in the first pool and the second pool to produce a population of tagged nucleic acids; amplifying the labelled nucleic acids, wherein the nucleic acids and the linked tags are amplified; and assaying the molecular tagged partitions with the NGS instrument; ii) a software module for generating sequence data for decoding the tag; and iii) a software module for analyzing the sequence data to decode the tags to reveal whether the nucleic acids for which sequence data has been assayed were amplified from templates in the first or the second pool. Another embodiment is a system further comprising a software module transmitting a result of the assay via a communications network.

VII. Examples

Example 1: Experimental Procedure for Methyl Binding Domain (MBD) Based Fractionation Sample Collection Samples, such as blood, serum or plasma, from subjects with lung cancer (e.g., NSCLC) were selected from Guardant Health repository that showed high circulating tumor DNA (ctDNA) content as determined by the GUARDANT360™ assay. Cell-free DNA (cfDNA) from healthy normal donors was extracted from blood-isolated plasma as previously described (Lanman et al., Analytical and clinical validation of a digital sequencing panel for quantitative, highly accurate evaluation of cell-free circulating tumor DNA, PLoS ONE 10(10): e0140712 (2015)).

cfDNA Extraction

The sample was subjected to proteinase K digestion. DNA was precipitated with isopropanol. DNA was captured on a DNA purification column (e.g., a QIAamp DNA Blood Mini Kit) and eluted in 100 µl solution. DNAs below 500 bp were selected with Ampure SPRI magnetic bead capture (PEG/salt). The resulting production was suspended in 30 µl H$_2$O. Size distribution was checked (major peak=166 nucleotides; minor peak=330 nucleotides) and quantified. In general, 5 ng of extracted DNA contain approximately 1700 haploid genome equivalents ("HGE"). The general correlation between the amount of DNA and HGE was listed as follow: 3 pg DNA=1 HGE; 3 ng DNA=1K HGE; 3 ng DNA=1M HGE; 10 pg DNA=3 HE; 10 ng DNA=3K HGE; 10 ng DNA=3M HGE.

DNA Fractionation

DNA was fractionated into multiple fractions (or partitions). cfDNA (10-150 ng) was fractionated into hypermethylated, intermediate methylated and hypomethylated fractions using the MethylMiner™ affinity enrichment protocol (Thermo Fisher Scientific, Cat #ME10025), except reaction conditions were modified using 300 mM NaCl incubation and wash buffer, and protocol for one microgram DNA input was scaled down for sub-microgram DNA inputs.

Bead Preparation

Washing the Dynabeads® M-280 Streptavidin: The Dynabeads® M-280 Streptavidin were washed using a wash buffer containing 300 mM NaCl prior to coupling with the MBD-Biotin Protein. The stock of Dynabeads® M-280 Streptavidin was resuspended to obtain a homogenous suspension. For each microgram of input DNA, 10 µl of beads were added to a 1.7-ml DNase-free microcentrifuge tube. The bead volume was brought to 100 µl with 1×Bind/Wash Buffer. The tube was placed on a magnetic rack for 1 minute to concentrate all of the beads on the inner wall of the tube before the liquid was removed and discarded. The tube was removed from the magnetic rack and an equal volume (e.g., about 100-250 µl) of 1×Bind/Wash Buffer was added to resuspend the beads. The resuspended beads were concentrated and washed for once more before proceeding to coupling the MBD-Biotin Protein to the beads.

Coupling Dynabeads® M-280 Streptavidin with the MBD-Biotin Protein: For each microgram of input DNA, 7 µl (3.5 µg) of MBD-Biotin Protein were added to a 1.7-ml DNase-free microcentrifuge tube. The bead volume was brought to 100 µl with 1×Bind/Wash Buffer containing 300 mM NaCl. The MBD-Biotin Protein was diluted and transferred to the tube of resuspended beads from the initial bead wash. The bead-protein mixture was mixed on a rotator mixer at room temperature for 1 hour, before proceeding to washing the MBD-beads.

Washing the MBD-beads: The MBD-beads in the tube were concentrated by placing the tube on a magnetic rack for 1 minute. The liquid was removed and discarded. The beads were resuspended with 100-250 µl of 1×Bind/Wash Buffer containing 300 mM NaCl and mixed on a rotating mixer at room temperature for 5 minutes. The beads were concentrated, washed and resuspended as described above for two more times. The tube was then placed on the magnetic rack for 1 minute and the liquid was carefully removed and discarded. The beads were resuspended with 100-250 µl of 1×Bind/Wash Buffer containing 300 mM NaCl before methylation DNA capture.

Capturing fragmented methylated DNA on the MBD-beads and incubating MBD-beads with fragmented DNA: In general, input DNA can range from 5 ng-1 µg. The control reaction typically uses 1 µg of K-562 DNA. To a clean 1.7-ml DNase-free microcentrifuge tube, 20 µl of 5×Wash/Bind Buffer containing 300 mM NaCl were added. A fragmented sample DNA, e.g., 5 ng-1 µg, was added to the tube and the final volume was brought to 100 µl with DNase-free water. The DNA/Buffer mixture was transferred to the tube containing the MBD-beads and mixed on a rotating mixer for 1 hour at room temperature. Alternatively, the mixture can be mixed overnight at 4° C.

Collecting non-captured DNA from the bead solution: The non-captured/non-methylated DNA was collected from the DNA and MBD-beads mixture. The tube containing a mixture of DNA and MBD-beads was placed on the magnetic rack for 1 minute to concentrate the beads, and the supernatant liquid was removed and saved in a clean DNase-free microcentrifuge tube. This saved supernatant liquid is the non-captured DNA supernatant and can be stored on ice. The beads were washed with 200 µl of 1×Bind/Wash Buffer containing 300 mM NaCl on a rotating mixer for 3 minutes. The beads were concentrated as described above and the supernatant liquid containing the non-captured/non-methylated/hypomethylated DNA was removed, saved and stored on ice as described above. The beads were washed, mixed, concentrated with the supernatant removed and saved for one more time to collect two wash fractions. Each wash fraction was stored on ice. The wash fractions can be pooled together and labelled accordingly.

Eluting the captured DNA: The captured DNA was eluted using an elution buffer containing 2000 mM NaCl. The beads were resuspended in 200 µl of elution buffer (2000 mM NaCl). The beads were incubated on a rotating mixer for 3 minutes and placed on the magnetic rack for 1 minute to concentrate all of the beads, and the liquid containing captured/hypermethylated DNA was removed and saved in a clean DNase-free microcentrifuge tube. The saved first fraction of captured/methylated DNA was stored on ice. The beads were resuspended and incubated one more time, and the liquid containing captured/methylated DNA was removed and saved in a second clean tube. The first and second collection of captured/methylated DNA were pooled and stored on ice.

Preparation of methylation fractionated DNA for analysis: Partitioned cfDNA, hyper methylated, intermediate methylated and non-methylated DNA was purified, for example, by SPRI bead cleanup (Ampure XP, Beckman Coulter), subsequently prepared for ligation (using NEBNext® Ultra™ End Repair/dA-Tailing Module), then ligated with modified Y-shaped dsDNA adapters containing non-random molecular barcodes as described in Lanman et al., 2015. The hypermethylated, intermediate methylated and hypomethylated cfDNA partitions were ligated with 11, 12, and 12 distinct, non-random molecular barcoded adapters, respectively. Ligated, partitioned cfDNA molecules for each sample were again purified with SPRI beads (Ampure XP) then re-combined into a PCR reaction with oligos universal to all adapter-ligated molecules (NEBNext Ultra II™ Q5 master mix), amplifying all cfDNA molecules from one sample together. Amplified DNA libraries were again purified using SPRI beads (Ampure XP), in preparation for target enrichment or whole genome sequencing (WGS) using standard preparation techniques.

Target capture and enrichment: The DNA samples may be enriched using commercially available protocols, for example, SureSelect$^{XT}$ Target Enrichment System for Illumina Multiplexed Sequencing.

Example 3: Methylation Profiling of CDKN2A

Figure 10:
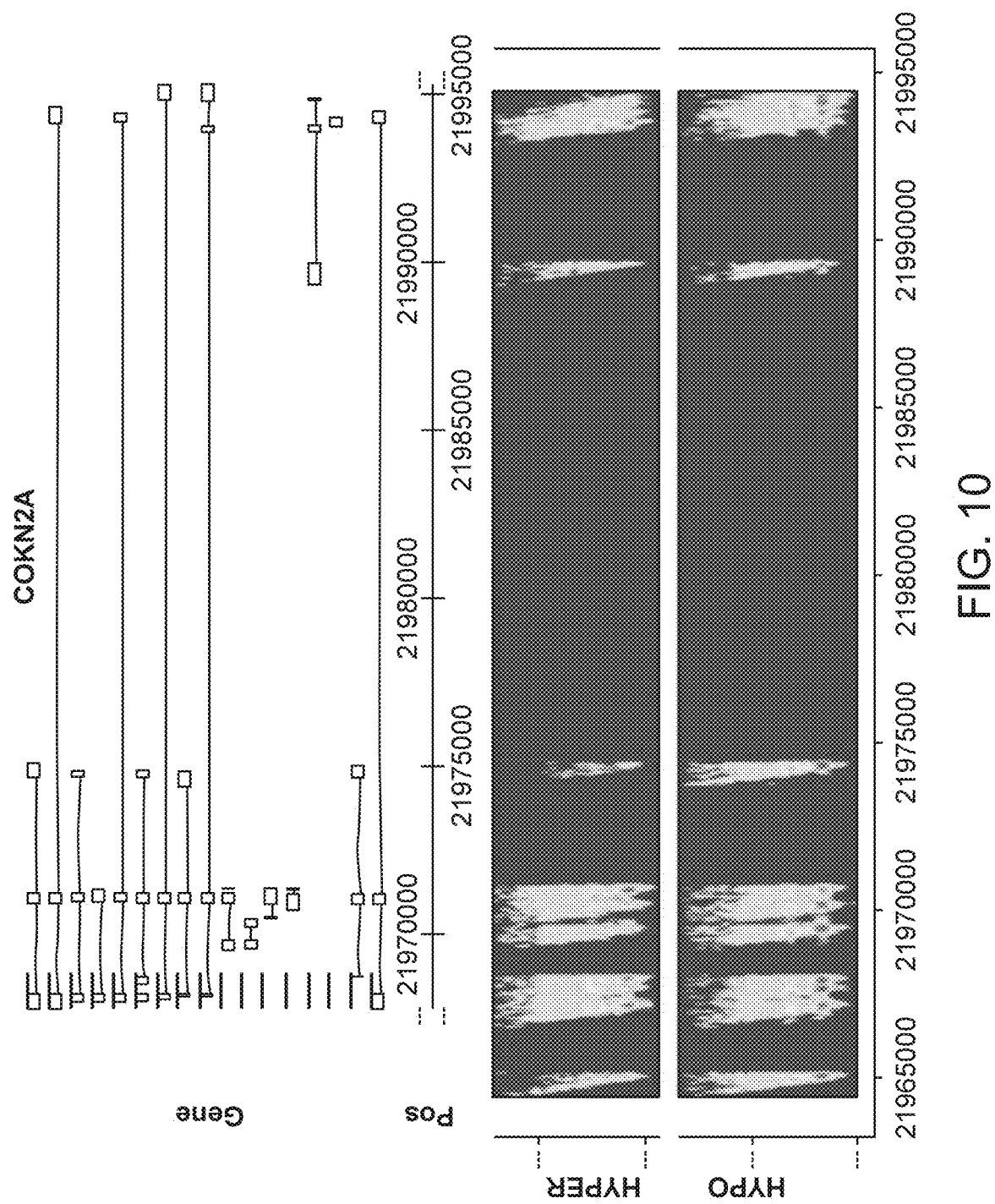
FIG. 10 shows an example of using fragmentomic data analysis on fractionated nucleic acid molecules. Genomic position is shown on the X-axis, fragment length on Y-axis and coverage or copies on Z-axis, and corresponding regions of elevated hypo- or hyper-methylation are indicated.

DNA methylation profiling in conjunction with fragmentomic data was used to capture differentially methylated regions (DMR) in CDKN2A gene. CDKN2A gene is a tumor suppressor gene that encodes p16INK4A and p14ARF proteins, involved in cell cycle regulation. A cfDNA sample was fractionated into hypomethylated and hypermethylated partitions using MBD-affinity purification. Upon fractionation, the nucleic acid molecules in each group were sequenced to generate sequence reads. The sequence reads when mapped to a reference genome provided fragmentomic data which was then combined with sequence reads from each of the fractionated partitions (FIG. 10). The CDKN2A gene showed a global increase in coverage of the hypomethylated partition compared to the hypermethylated partition.

Example 4: Methylation Profiles of Normal and Lung Cancer Samples

Figure 11:
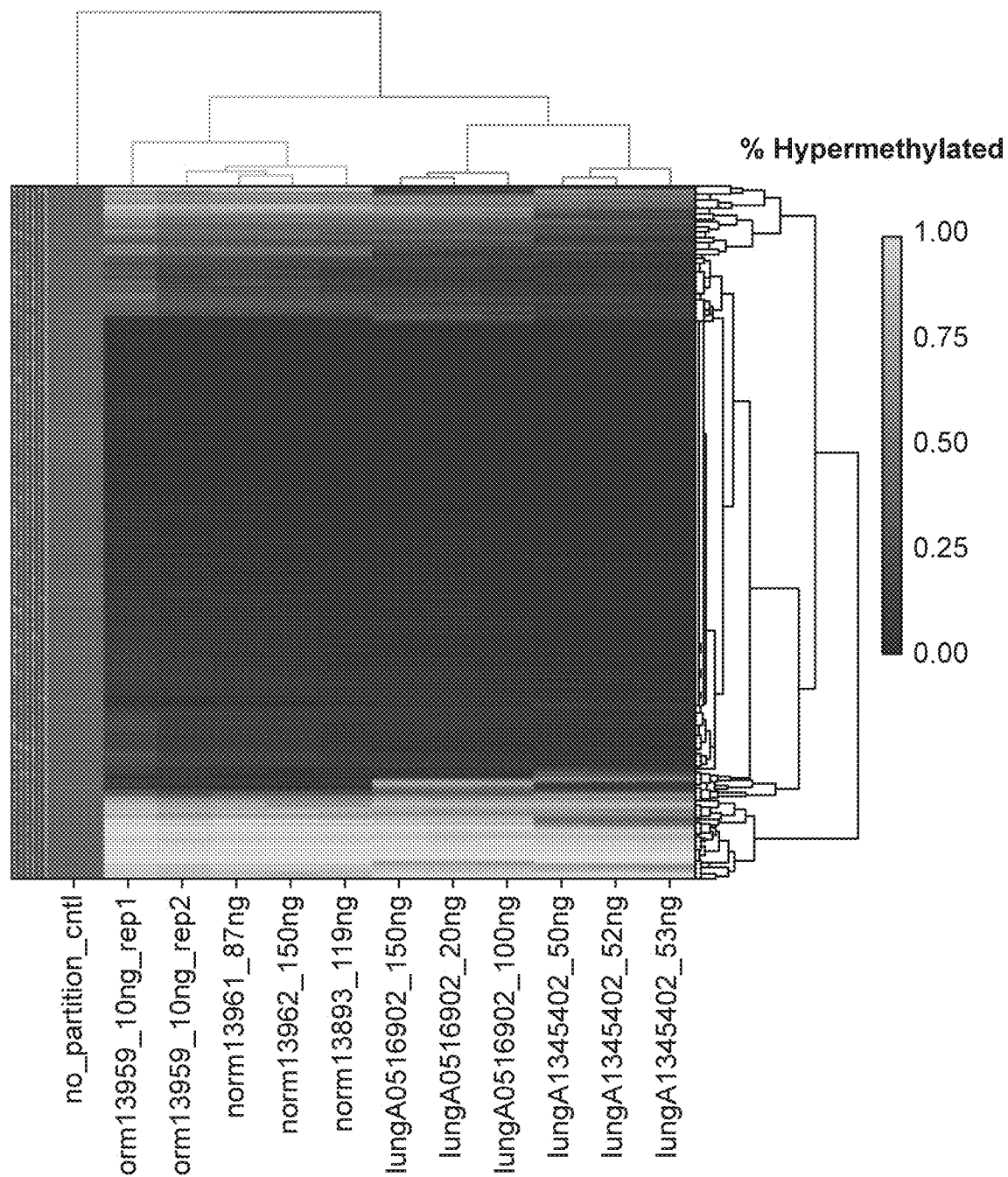
FIG. 11 shows methylation profiling of normal and lung cancer samples.

As shown in FIG. 11, the MBD-partitioning process was applied to four cfDNA samples from healthy donors (Norm13893, Norm13959, Norm13961, Norm13962) and two cfDNA samples from lung cancer patients with high % ctDNA (LungA1345402, LungA0516902), with varying input amount (10-150 ng cfDNA) and replicates (e.g., 3 replicates). The samples were clustered hierarchically by the percentage of hypermethylated DNA across all the genomic loci targeted in the panel. The percentage hypermethylated DNA can be determined by dividing number of hypermethylated cell-free DNA fragments by total number of cell free DNA fragments observed across all partitions. The panel is a custom gene panel that covers about 30 kb genomic region. The panel also has higher sensitivity for detecting different cancers, such as lung cancer, colorectal cancer, etc. The samples from healthy donors were clustered separately from the samples from lung cancer patients. The individual lung cancer samples had distinct methylation profiles that were further clustered separately (i.e. replicates of each lung cancer sample are correctly identified and grouped together). See, e.g., WO 2017/181146, Oct. 19, 2017.

Example 5: Methylation Profiling Using Whole Genome Sequencing

DNA methylation profiling was integrated with fragmentomic data to determine abnormal fragmentation patterns and hence altered chromatin structure in a clinical sample (FIG. 12A, FIG. 12B, and FIG. 12C). Nucleic acid molecules were derived from lung cancer patients. The nucleic acid molecules were fractionated using MBD-affinity purification into hypomethylated and hypermethylated partitions. Upon fractionation, the nucleic acid molecules in each partition were sequenced to generate sequence reads. The sequence reads when mapped to a reference genome provided fragmentomic data. The fragmentomic data, such as genomic position, fragment length and coverage, was combined with the sequence reads from each partition. As shown in FIG. 12A and FIG. 12B, a 600 bp region in transcription start site (TSS) is on X-axis and frequency or coverage is indicated on Y-axis. FIG. 12C shows fraction of hypermethylated fragments when compared to total fragments on X-axis and frequency on Y-axis. For example, in FIG. 12C, the fraction of hypermethylated fragments among total fragments is about 0.2 (i.e. about 20%).

Example 6: Methylation Profiling of MOB3A and WDR88

Figure 13A:
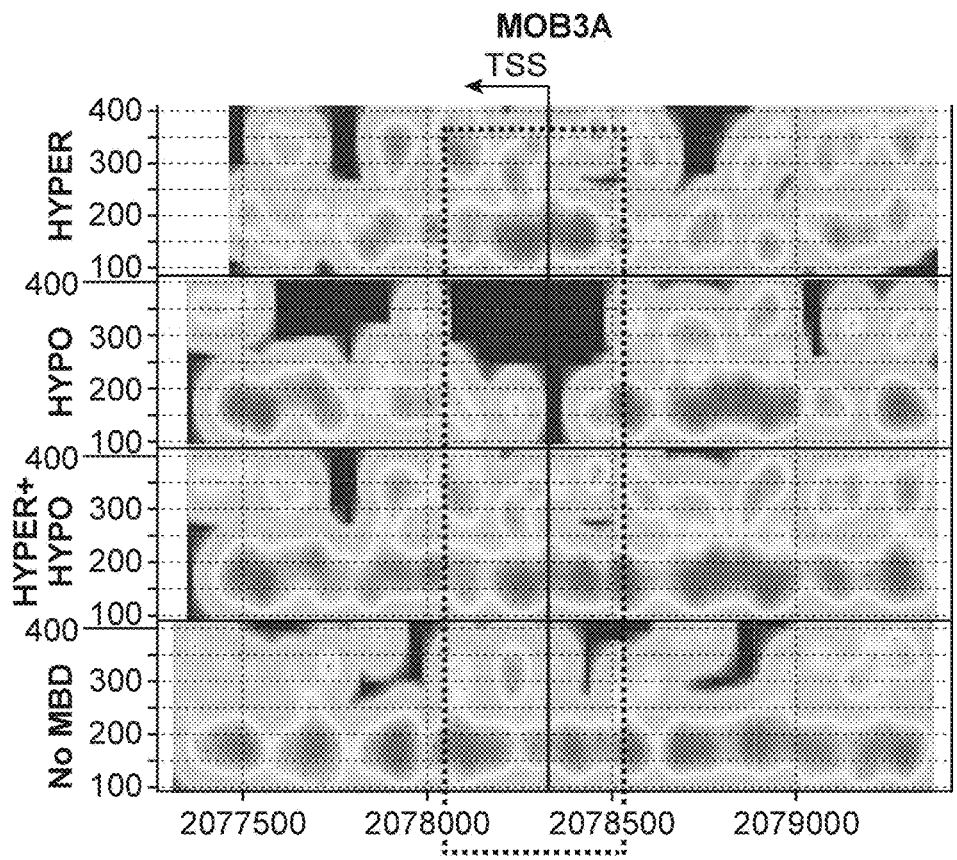
FIG. 13A and FIG. 13B show methylation profiling of MOB3A and WDR88.
Figure 13B:
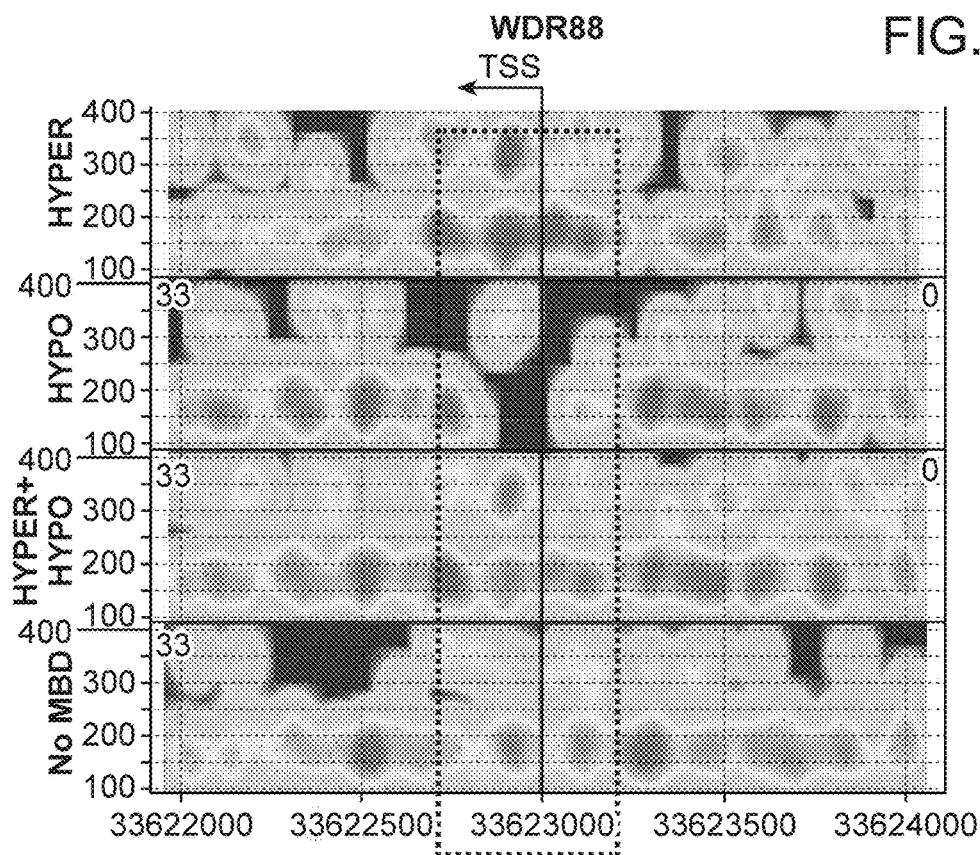

DNA methylation profiling was integrated with fragmentomic data to determine differences in epigenetic regulations (FIG. 13A and FIG. 13B). The nucleic acid molecules were fractionated using MBD-affinity purification into hypomethylated and hypermethylated partitions. Upon fractionation, the nucleic acid molecules in each partition were sequenced to generate sequence reads. The sequence reads when mapped to a reference genome provided fragmentomic data. The fragmentomic data, such as genomic position and coverage, was combined with sequence reads from each of the fractionated group.

The MOB3A gene may have unknown biochemical functions and may be implicated sustaining tumor growth and proliferation. Heat maps, as in FIG. 13A, showed more coverage for hypermethylated compared to hypomethylated near start site of TSS in the samples from healthy individuals. The example provided an application of combining fractionated groups with fragmentomic data to detect markers in TSS of genes that can be indicative of cancer. These data showed that fractionated groups (or partitions), hypermethylated and hypomethylated, provided better resolution for discerning methylation status across a genomic region, such as TSS. As described above, the coverage in fractionated groups showed differences in methylation status across TSS. The example provided an application of fractionating nucleic acid molecules to provide better resolution of methylation status across a gene.

WDR88 gene may be implicated in cell cycle regulation, apoptosis and autophagy. Heat maps showed more coverage for hypermethylated compared to hypomethylated near start site of TSS (FIG. 13B) in the samples from healthy individuals. Further, FIG. 13B showed that fractionated groups, hypermethylated and hypomethylated, provided better resolution for discerning methylation status across a genomic region, such as TSS. As described above, the coverage in fractionated groups showed differences in methylation status across TSS. The example provided an application of fractionating nucleic acid molecules to provide better resolution of methylation status across a gene.

Figures 14A, 14B:
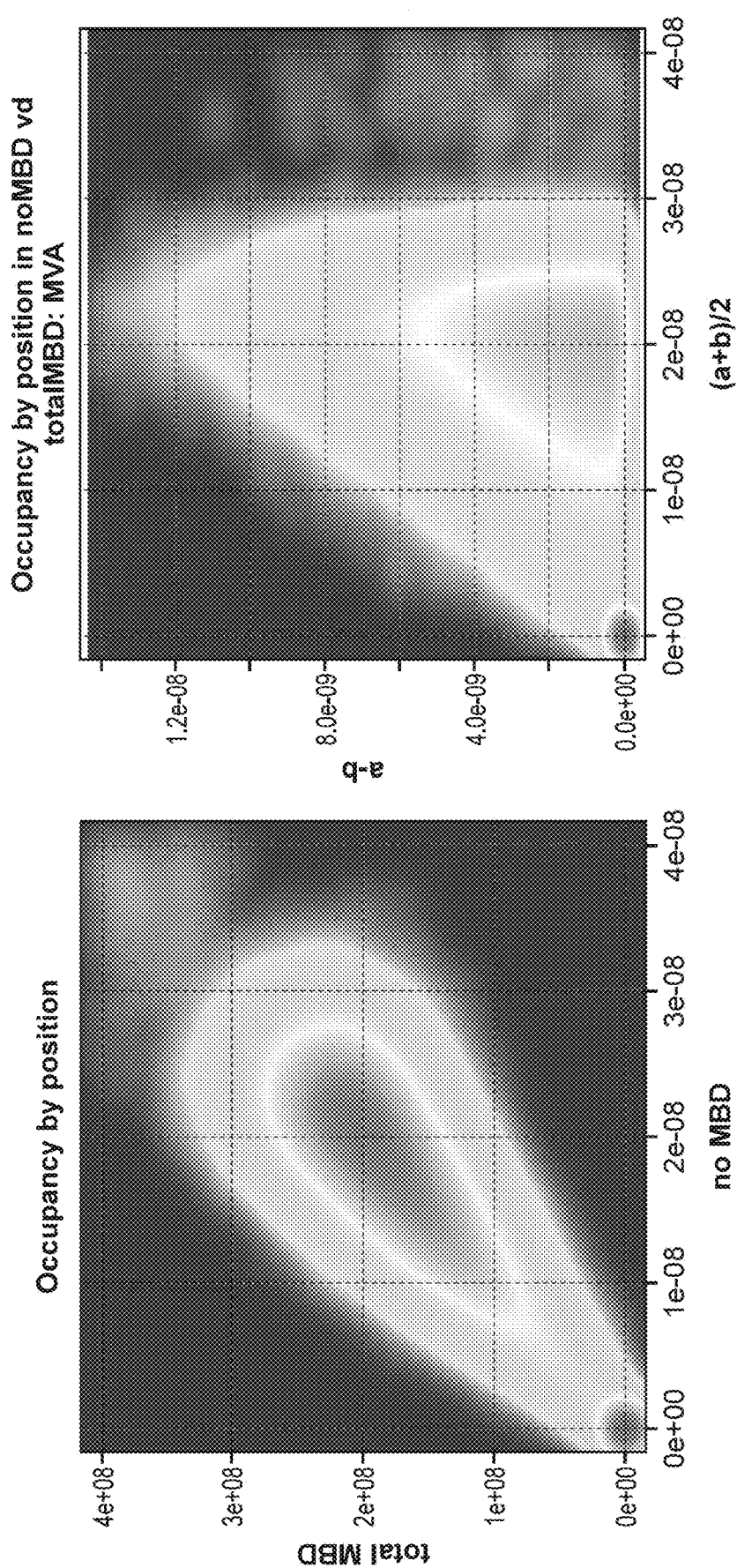
FIG. 14A and FIG. 14B show methylation profiling of fractionated and unfractionated groups.

Example 7: Methylation Profiling of Recombined Partitions and Unfractionated Sample FIG. 14A shows a heat map with coverage from unfractionated group (no MBD) and recombined partitions after MBD-affinity partitioning (total MBD), respectively on X-axis and Y-axis. The partitions were recombined in silico after partitioning into hyper- and hypo-methylated partitions to form "hyper+hypo" or "total MBD". The heat map shows a linear correlation between the coverage for no MBD and total MDB. The linear correlation indicates similar coverage and may provide similar resolution of methylation status across a genomic locus. The level of resolution obtained by no MBD and/or total MBD may not be sufficient to distinguish differences in methylation status across a locus, showing an unexpected advantage of partitioning based on MBD-affinity.

FIG. 14B shows a MVA plot heat map with total MBD. X-axis shows average fragments in total MBD (recombined hyper- and hypomethylated partitions) as (a+b)/2, where a=total MBD and b=noMBD.

Figure 15:
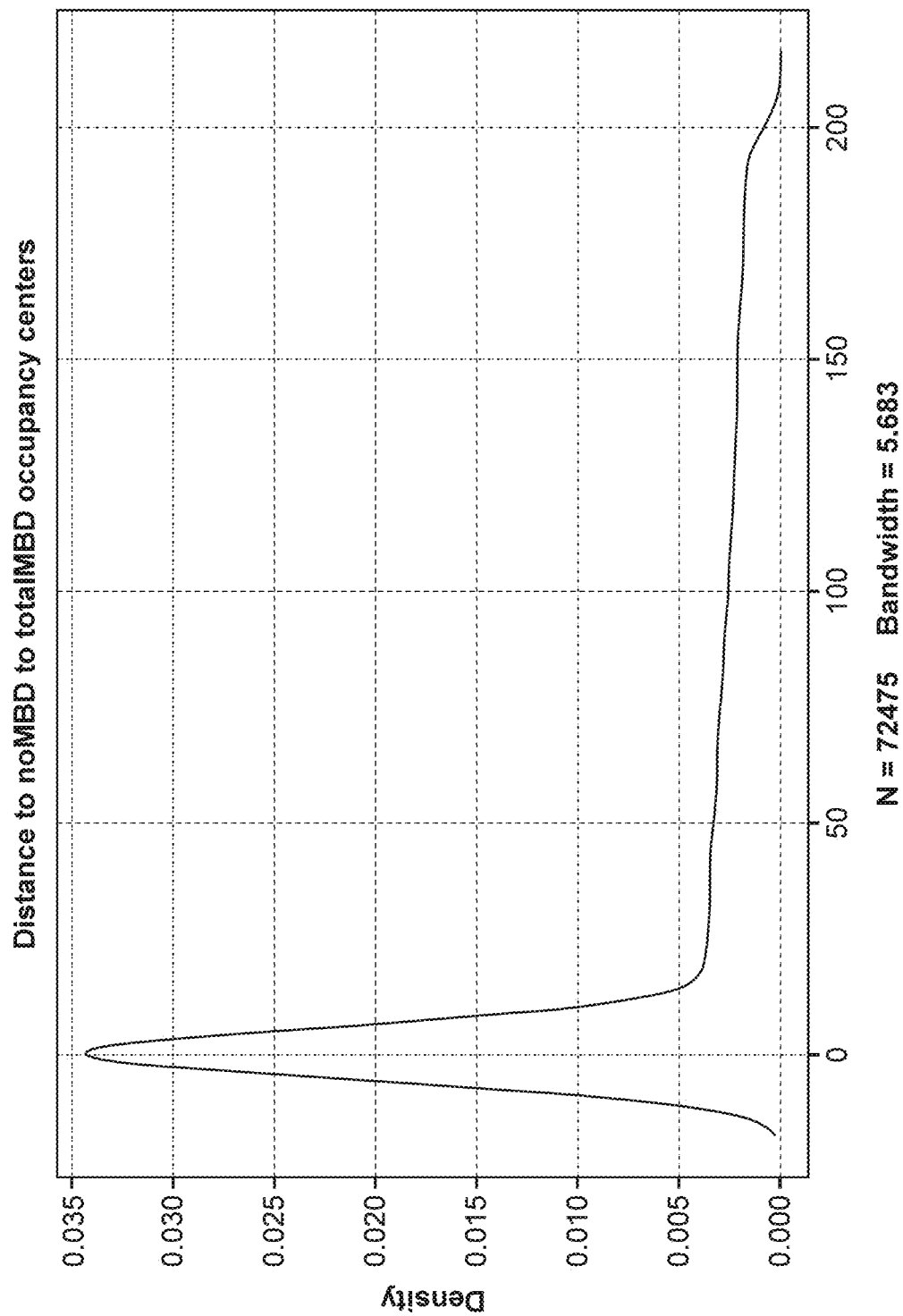
FIG. 15 shows nucleosome organization for fractionated and unfractionated samples.

Example 8: Nucleosome Organization Between Recombined Partitions (Total MBD) and Unfractionated Sample As shown in FIG. 15, differences in the distances between nucleosome occupancy centers for the total MBD (in silico recombined hyper- and hypomethylated partitions) and noMBD (unfractionated) samples across a genomic region were plotted on X-axis. Differences in distribution of distances between nucleosome occupancy centers for the total MBD and noMBD samples across a genomic region were plotted on Y-axis as indicated by "density". The total MBD samples were prepared by recombining the hyper- and hypomethylated partitions in silico. These results show that the MBD partitioning does not affect nucleosomal occupancy.

Example 9: Validation of MBD Signal

Figure 16:
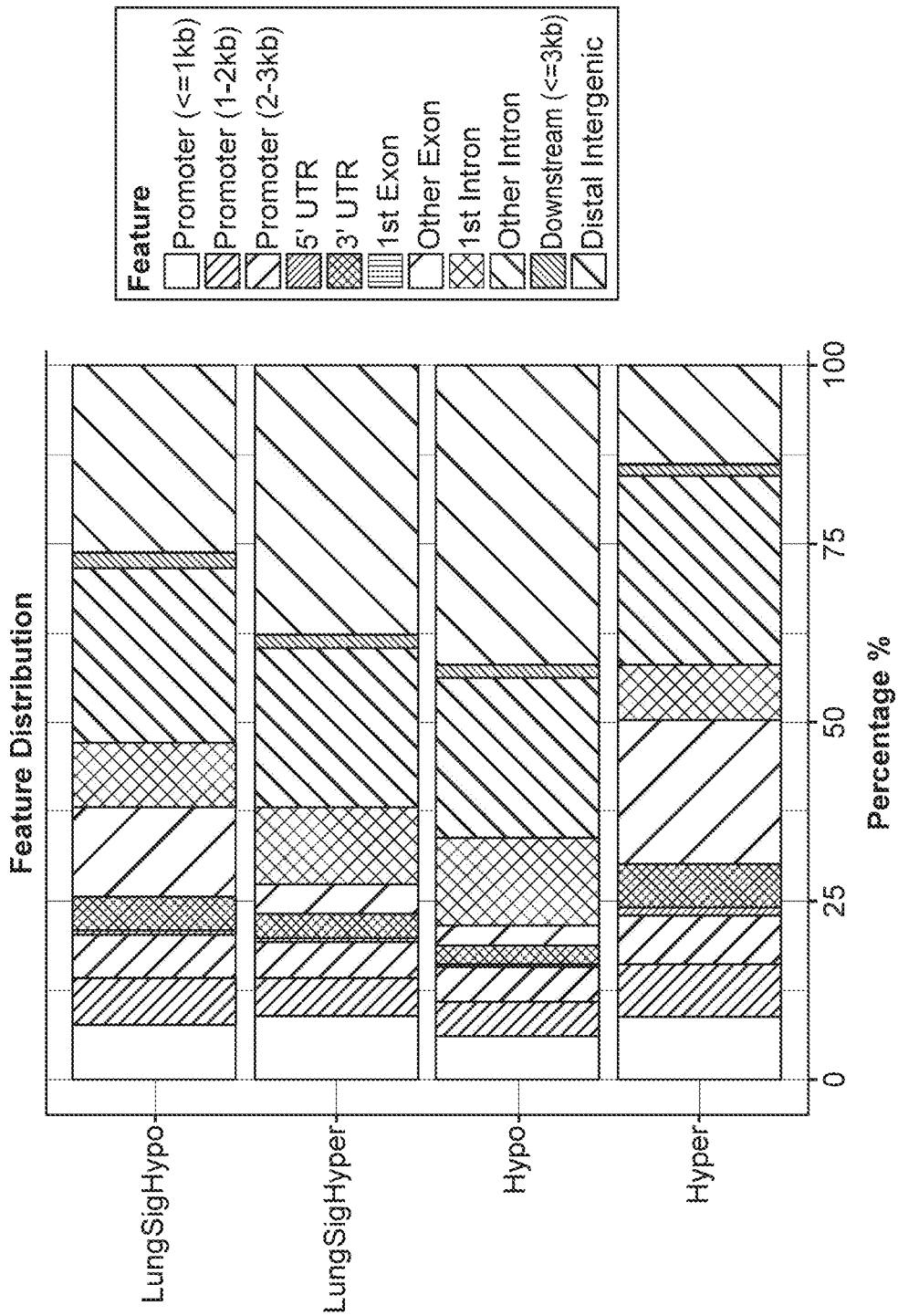
FIG. 16 shows validation of MBD signal.

MBD-partitioned samples were used to discern nucleosomal occupancy in healthy and cancer samples. In this example, blood samples from six lung cancer patients and three non-malignant healthy adults were obtained. Cell-free Nucleic acids from the samples were extracted and partitioned using MBD—affinity purification into hyper- and hypo-methylated partitions. The nucleic acid samples were sequenced using whole genome sequencing. The percentage hypermethylated fragments for each partition and for all the samples were determined. FIG. 16 shows MBD signal in hyper- and hypomethylated partitions from lung cancer patients (rows 1 and 2 from top) and from healthy adults (rows 3 and 4). As shown in FIG. 16, cell-free DNA fragments from lung cancer patients show enrichment of distal intragenic regions in hypermethylated partition (LungSigHyper) when compared with the hypermethylated partition from healthy individuals. In addition, the distribution of characteristics in top 5% highest percentage hypermethylated peaks (LungSigHyper) and hypomethylated peaks (LungSigHypo) shows significant enrichment of hypomethylated peaks in all exons besides of exon 1 (FIG. 16, rows 1 and 2).

Example 10: Methylation Profiling of AP3D1 Gene

The methods described herein were used for prognosis of lung cancer. In an experiment, a sample with nucleic acid molecules from a lung cancer patient was fractionated into hypomethylated and hypermethylated partitions using MBD-affinity purification. As a control, a sample was not partitioned (no MBD). The samples were sequenced using whole genome sequencing.

Figures 18A, 18B:
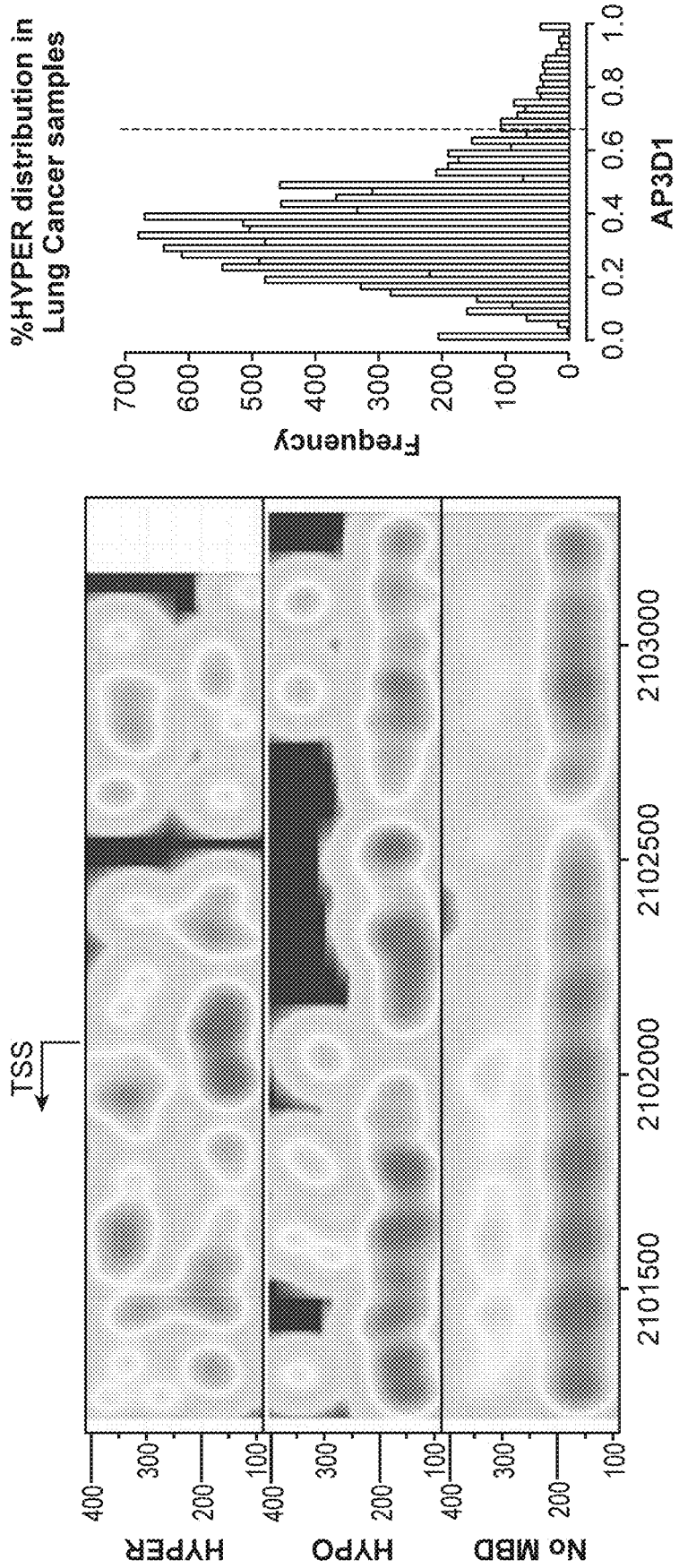
FIG. 18A and FIG. 18B show methylation profiling of AP3D1 gene.

AP3D1 gene may encode AP-3 complex subunit delta-1 that may be implicated in organelle transportation. Heat maps showed more coverage for hypermethylated partition compared to hypomethylated partition and/or no MBD near of the TSS (FIG. 18A). Hypermethylated partition showed a stronger and/or a more localized coverage than no MBD group. As shown in the heat map, hypermethylated partition had a much-localized strong coverage near TSS while no MBD group had a similar coverage across genomic region. Average percent hypermethylation was also determined as indicated by the red line in FIG. 18B. The example may provide an application of fractionating nucleic acid molecules to provide better resolution of methylation status across a gene. These results show that AP3D1 gene is hypermethylated especially near TSS (FIG. 18A) and that AP31 gene is hypermethylated (>60% as shown in FIG. 18B). Deregulation of AP3D1 gene can be involved in causing lung cancer. Thus, this example may provide an application for this method in prognosis of lung cancer by monitoring methylation profile of an individual.

Example 11: Methylation Profiling of DNMT1 Gene

In another example, methylation profiling of DNMT1 gene was examined. DNMT1 gene encodes an enzyme that catalyzes the transfer of methyl groups to specific CpG dinucleotides in DNA. DNMT1 has been implicated in maintenance of DNA methylation to ensure the fidelity of replication of inherited epigenetic patterns. Aberrant methylation patterns may be associated with cancers and developmental abnormalities.

Figure 19B:
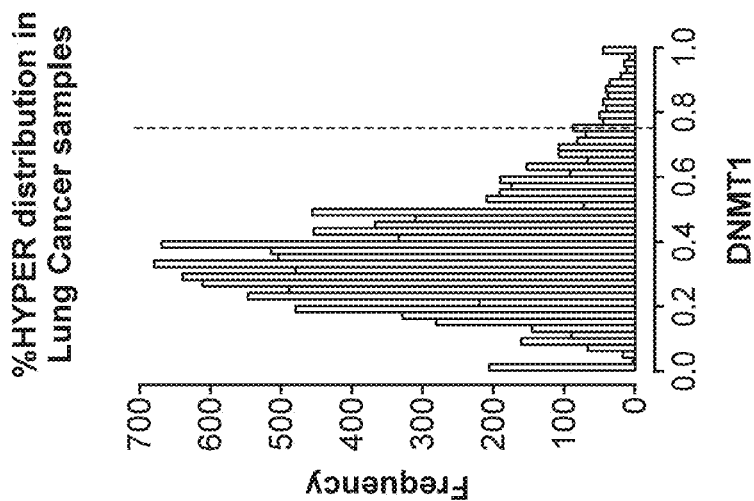
FIG. 19A and FIG. 19B show methylation profiling of DNMT1 gene.
Figure 19A:
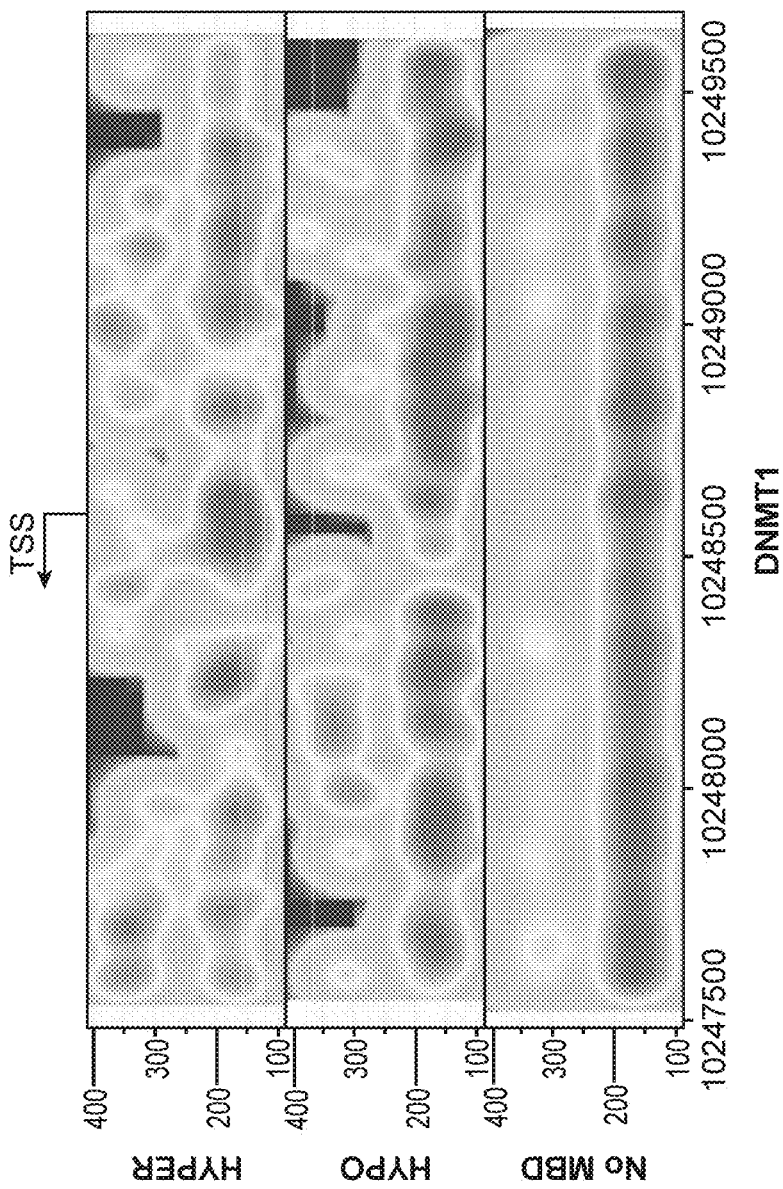

Heat maps for hypermethylated, hypomethylated and no MBD are shown with respect to the TSS (FIG. 19A). The hypermethylated partition showed a stronger and/or a more localized coverage than the no MBD group. The hypermethylated partition had a localized and a stronger coverage near TSS while no MBD group had similar coverage across the gene. Average percentage hypermethylation was also determined as indicated by the red line in FIG. 19B to be about 75%. These results show that DNMT1 gene is hypermethylated especially near TSS (FIG. 19A) and that DNMT1 gene is hypermethylated (about 75% as shown in FIG. 19B). Aberrant methylation patterns along with changes in chromatin structure may result deregulation of DNMT1 that can be involved in causing lung cancer. Thus, this example may provide an application for this method in prognosis of lung cancer by monitoring methylation profile of an individual. The example may also provide an application of fractionating nucleic acid molecules to provide better resolution of methylation status across a gene.

Example 12: Modified-Histone Fractionating

This example demonstrates partitioning using modified-histone approach. DNA is partitioned based on histone modification. Briefly, agarose beads are blocked with BSA and, following washing, the beads are pre-incubated with antibodies against the H3K9me3 and H4K20me3 (Millipore, Temecula, CA, USA) for 4 h at 4° C. Subsequently, 200 μl of plasma is diluted into 800 μl of the partition dilution buffer and is then added to the pelleted agarose beads that were pre-incubated with antibodies. Following overnight incubation at 4° C., the beads are washed with low salt, high salt, LiCl and Tris/EDTA buffers. Finally, the chromatin is eluted by incubating the beads at 65° C. and proteins are removed by treatment with proteinase K. Partitioned DNA is then purified using an appropriate purification kit and stored at −20° C.

Example 13: Fractionation Based on Protein-Bound Regions

This example demonstrates partitioning approach using a protein-bound region. DNA is partitioned based on differences in binding to protein A. The nucleic acid molecules in a sample can also be fractionated based on protein-bound regions. For example, the nucleic acid molecules can be fractionated into different groups based on the nucleic acid molecules that are bound to a specific protein and those that are not bound to that specific protein. Nucleic acid molecules can be fractionated based on DNA-protein binding. Protein-DNA complexes can be fractionated based on a specific property of a protein. Examples of such properties include various epitopes, modifications (e.g., histone methylation or acetylation) or enzymatic activity. Examples of proteins which may bind to DNA and serve as a basis for fractionation may include, for example, protein A or protein G. Experimental procedures, such as Chromatin-immunoprecipitation is used to fractionate the nucleic acid molecules based on protein A bound regions.

Example 14: Fractionating Based on Hydroxymethylation

This example demonstrates partitioning using modified-histone approach. DNA is partitioned based on hydroxymethylation. Briefly, 5-hmC-modified bases are glycosylated in vitro. Specific glucosylation of 5-hmC is accomplished by following the protocol of the highly active 5-hmC Glucosyltransferase enzyme from Zymo Research (zymoresearch.com/epigenetics/dna-hydroxymethylation/5-hmc-glucosyltransferase). J-Binding Protein-1 (JBP-1) specifically binds to glucosylated DNA with high affinity, allowing 5-hmC levels to be determined by JBP-1-based enrichment. Additionally, glucosylation of 5-hmC alters the digestion of DNA by several restriction enzymes, and therefore digestion patterns of 5-hmC-glucosylated DNA can be used to assess DNA hydroxymethylation status.

Example 15: Fractionating Based on Strandedness of Nucleic Acid Molecules

The nucleic acid molecules in a sample are fractionated based on strandedness. For example, the ssDNA and dsDNA are fractionated into two groups. These groups are subjected to a sequencing assay, either individually or simultaneously. A nucleic acid sample having both ssDNA and dsDNA are fractionated by not subjecting the sample to a denaturation step during fractionation. The denaturation step converts the dsDNA into ssDNA and does not allow fractionation of the nucleic acid molecules based on strandedness.

Example 16: Molecular Partitioning of ssDNA and dsDNA with Modified Pre-Amplification Target Capture Protocol (NEBNext Direct)

A novel hybrid capture methodology, in which a pre-amplification hybrid capture target sequencing protocol (e.g., NEBNext Direct HotSpot Cancer Panel), was applied to a cell-free DNA (cfDNA) sample without DNA denaturation, capturing the ssDNA molecules (FIG. 18). The non-bound fraction containing dsDNA molecules was isolated, denatured to ssDNA and applied to the capture protocol.

The pre-amplification hybrid capture sequencing protocol used was the NEBNext Direct HotSpot Cancer Panel, containing baits to 190 common cancer targets from 50 genes, encompassing approximately 40 kb of sequence and including over 18,000 COSMIC features (NEBNext Direct HotSpot Cancer Panel; neb.com/products/e7000-nebnext-direct-cancer-hotspot-panel). Briefly, the NEBNext Direct target enrichment approach rapidly hybridizes DNA samples to biotinylated oligonucleotide baits, which define the 3' end of each target of interest. Bait-target hybrids were bound to streptavidin beads and enzymatic reactions were used to remove 3' off target sequence. Ensuing library prep converted the targets into Illumina-compatible libraries that included molecular tags and a sample barcode. The use of the kit allowed capture of all ssDNA and dsDNA molecules in a sample by denaturing the DNA sample prior to hybridization with baits.

Figure 20:
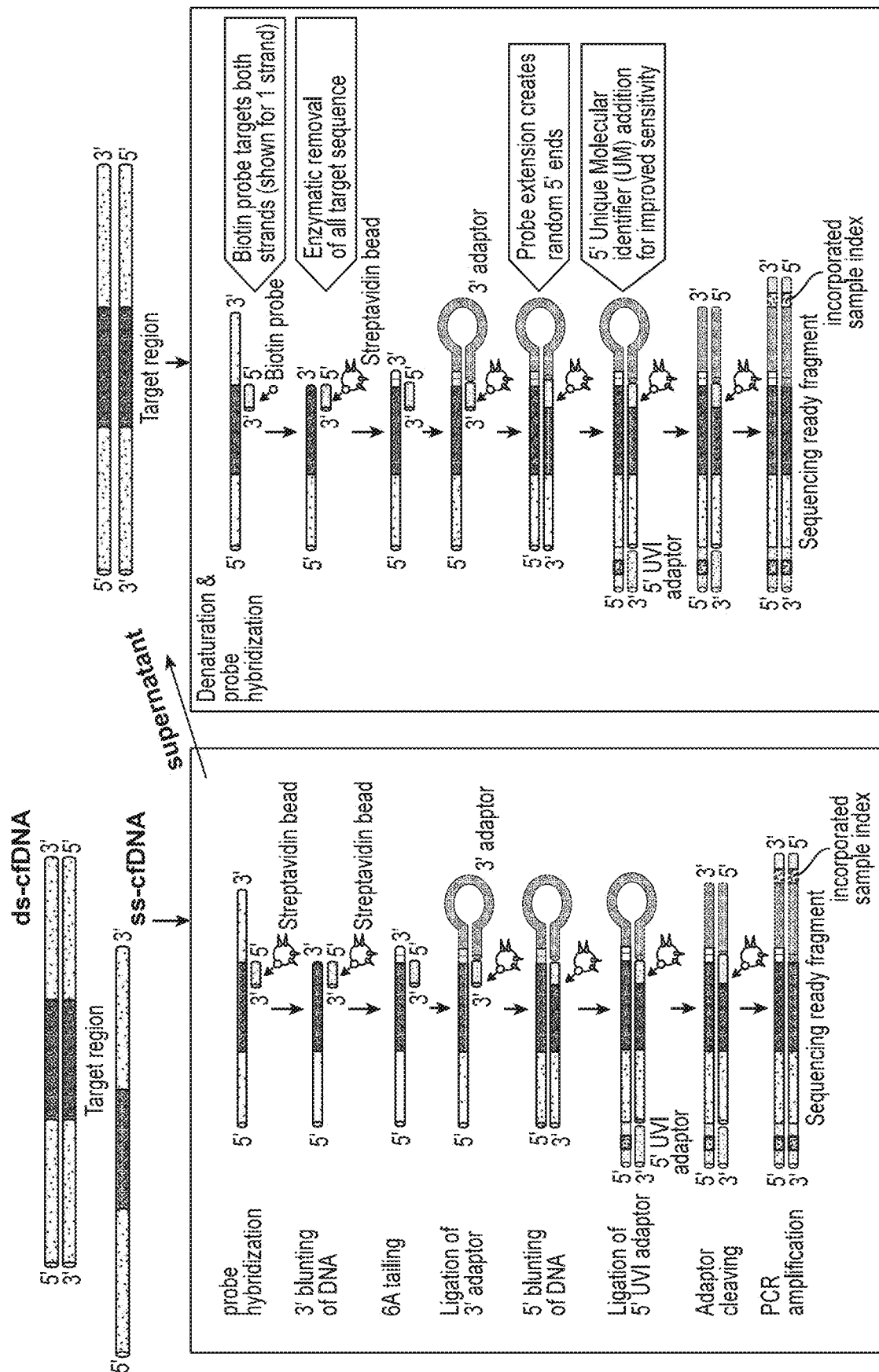
FIG. 20 shows procedure for fractionating based on strandedness of nucleic acid molecules
Figure 21:
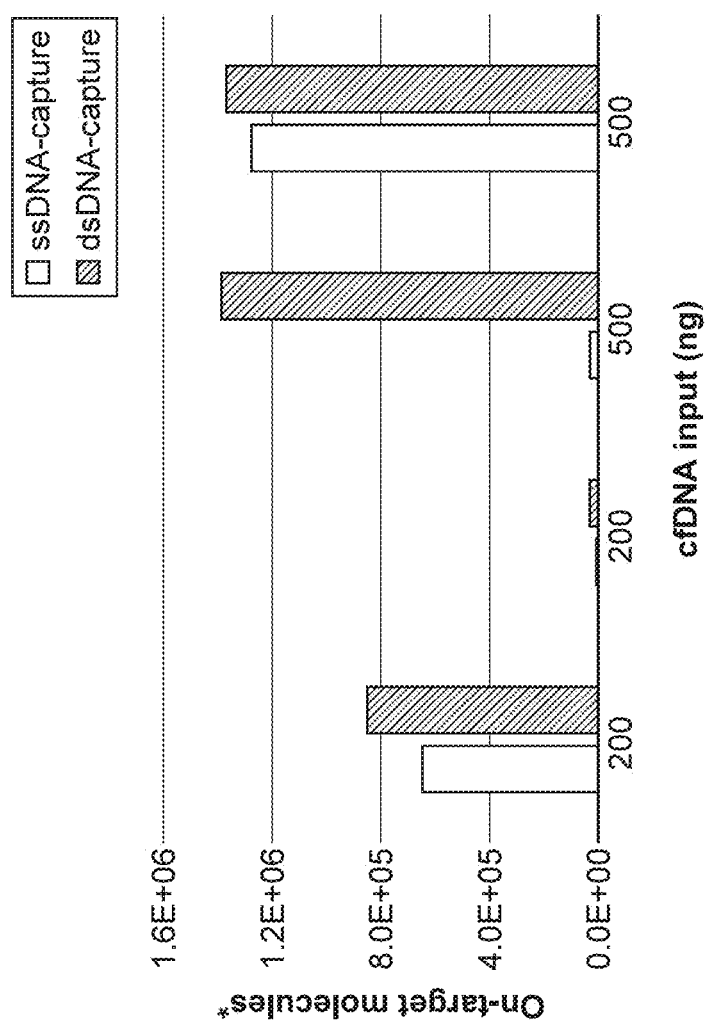
FIG. 21 shows fractionation of nucleic acid molecules into ssDNA and dsDNA. X-axis shows two technical replicates of two samples with varying input DNA (200 ng and 500 ng). Y-axis shows copy number of on-target molecules using quantitative PCR amplification. The figure shows quantitative determination of target sequence in each group of fractionated cfDNA.
Figure 22:
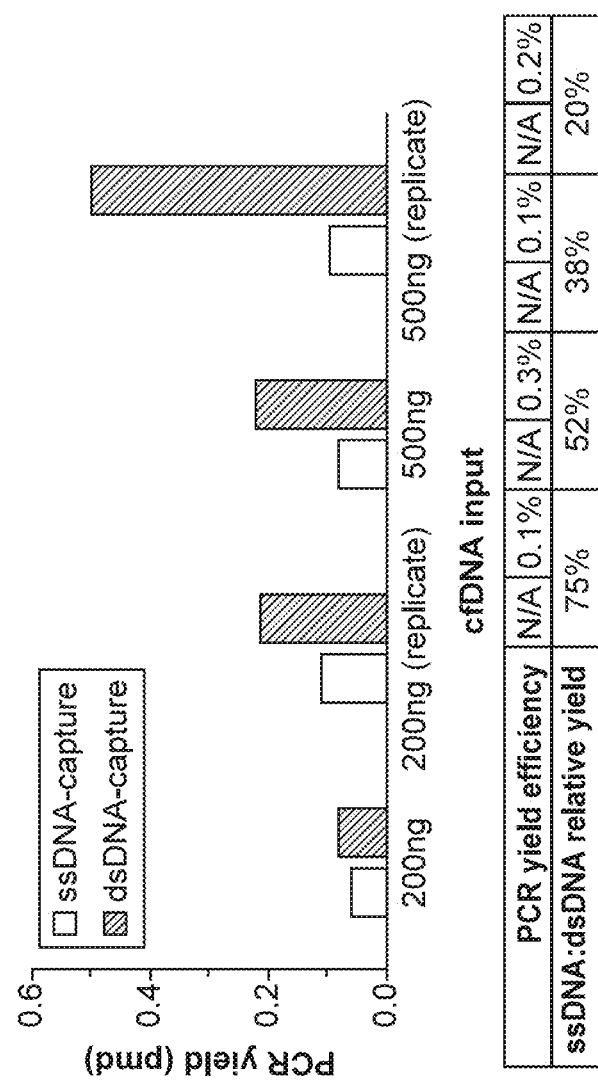
FIG. 22 shows PCR yield following fractionation of nucleic acid molecules into ssDNA and dsDNA. X-axis shows cfDNA input (200 ng and 500 ng) in two technical replicates while Y-axis shows PCR yield in pmol.

A cfDNA sample containing ss- and ds-cfDNA was subjected to target capture protocol omitting the upfront dsDNA denature step. The captured ssDNA molecules were prepared for NGS by NEBNext protocol (left column in FIG. 20), while the supernatant from the capture was applied to a second target capture protocol, with standard upfront dsDNA denature step and subsequently prepared for NGS (right column in FIG. 20). CfDNA extracted from plasma was quantified by electrophoresis-based measurement. A sample volume equivalent to 200 ng or 500 ng was applied to the NEBNExt Direct HotSpot Cancer Panel assay, omitting the DNA denaturation step, such that only ssDNA molecules hybridized to the baits. The supernatant of the capture, containing dsDNA molecules and non-targeted ssDNA molecules was retained and subjected to a second target capture (FIG. 20). Both ssDNA and dsDNA libraries were prepared separately for NGS, with unique sample barcode tags that are identified in downstream bioinformatics analysis. Both ssDNA and dsDNA-prepared libraries were sequenced on an Illumina NextSeq 500 (2×75 paired ends) and the total number of on-target molecules (corresponding to 40 kb baits) was computed (FIG. 1).

A cell-free DNA (cfDNA) sample with both the single-stranded cell-free DNA (ss-cfDNA) and the double-stranded cell-free DNA (ds-cfDNA) was fractionated into ss-cfDNA and ds-cfDNA groups, respectively, using method described above (FIG. 20). In two of the sequenced samples, the ssDNA library contains ~80% of the dsDNA (on-target molecules, first 200 ng and second 500 ng cfDNA input). The second 200 ng cfDNA failed to produce both ssDNA and dsDNA libraries, and indicated a probable error in sample processing upstream of the ssDNA/dsDNA partitioning process, while the first 500 ng cfDNA input produced significant dsDNA library only, which suggested that the relative amount of ssDNA and dsDNA in a cfDNA sample was variable. The on-target molecules were computed as defined by the Picard package from the Broad Institute (Picard metrics; broadinstitute.github.io/picard/picard-metric-definitions.html). The PCR yield for this experiment was shown in FIG. 20. A relative yield, PCR yield for ssDNA/PCR yield for dsDNA, was determined to be between 20% and 75% for all four samples.

Example 17: Sensitive Somatic Mutation Detection Retained with MBD-Based Methylation Partitioning Method Sample Collection and Pooling Samples were selected from Guardant Health repository that showed high cfDNA yield. Clinical samples were prepared by mixing 96 samples in equal volumes. This serves as a testing material for assay sensitivity for mutation detection, as pools contain mutations from reference genome at <0.02% to 100%. Two different clinical samples (PowerpoolV1 and PowerpoolV2) with unique component samples were prepared.

DNA Partitioning

Powerpool cfDNA was partitioned into multiple fractions. cfDNA (15 or 150 ng) was partitioned into hypermethylated, intermediate methylated and hypomethylated fractions using the MethylMiner™ affinity enrichment protocol (Thermo Fisher Scientific, Cat #ME10025), except reaction conditions were modified using 300 mM NaCl incubation and wash buffer, and protocol for one microgram DNA input was scaled down linearly for sub-microgram DNA inputs.

Bead Preparation

Washing the Dynabeads® M-280 Streptavidin

The Dynabeads® M-280 Streptavidin were washed using 1×Bind/Wash Buffer (containing 160 mM NaCl) prior to coupling with the MBD-Biotin Protein. Briefly, the stock of Dynabeads® M-280 Streptavidin was resuspended to obtain a homogenous suspension. For each microgram of input DNA, 10 µl of beads were added to a 1.7-ml DNase-free microcentrifuge tube. The bead volume was brought to 100 µl with 1×Bind/Wash Buffer. The tube was placed on a magnetic rack for 1 minute to concentrate all of the beads on the inner wall of the tube before the liquid was removed and discarded. The tube was removed from the magnetic rack and an equal volume (e.g., about 100-250 µl) of 1×Bind/Wash Buffer was added to resuspend the beads. The resuspended beads were concentrated and washed for once more before proceeding to coupling the MBD-Biotin Protein to the beads.

Coupling Dynabeads® M-280 Streptavidin with the MBD-Biotin Protein

For each microgram of input DNA, 7 µl (3.5 µg) of MBD-Biotin Protein were added to a 1.7-ml DNase-free microcentrifuge tube. The bead volume was brought to 100 µl with 1×Bind/Wash Buffer containing 300 mM NaCl. The MBD-Biotin Protein was diluted and transferred to the tube of resuspended beads from the initial bead wash. The bead-protein mixture was mixed on a rotator mixer at room temperature for 1 hour, before proceeding to washing the MBD-beads.

Washing the MBD-Beads

The tube containing the MBD-beads was concentrated by placing the MBD-beads on a magnetic rack for 1 minute. The liquid was removed and discarded. The beads were resuspended with 100-250 µl of 1×Bind/Wash Buffer containing 160 mM NaCl and mixed on a rotating mixer at room temperature for 5 minutes. The beads were concentrated, washed and resuspended as described above for two more times. The tube was then placed on the magnetic rack for 1 minute and the liquid was carefully removed and discarded. The beads were resuspended with 10 µl of 1×DNA capture buffer (containing 300 mM NaCl) per each µl of streptavidin beads used.

Capturing Fragmented Methylated DNA on the MBD-Beads

Incubating MBD-Beads with Fragmented DNA

In general, input DNA can range from 5 ng-1 µg. The control reaction typically used 1 µg of K-562 DNA. To a clean 1.7-ml DNase-free microcentrifuge tube or PCR tube, a fragmented sample DNA, e.g., 5 ng-1 µg, was added to the tube, with an equal volume of 2×DNA capture buffer (containing 300 mM NaCl) and the final volume was brought to 100 or 200 µl with 1×DNA capture buffer. The DNA/Buffer mixture was transferred to the tube containing the MBD-beads and mixed on a rotating mixer for 1 hour at room temperature. Alternatively, the mixture can be mixed overnight at 4° C.

Collecting Non-Captured DNA from the Bead Solution

The non-captured/non-methylated DNA was collected from the DNA and MBD-beads mixture. Briefly, the tube containing a mixture of DNA and MBD-beads was placed on the magnetic rack for 1 minute to concentrate all of the beads, and the supernatant liquid was removed and saved in a clean DNase-free microcentrifuge tube. This saved supernatant liquid is the non-captured DNA supernatant/non-methylated DNA fraction and can be stored on ice. The beads were washed with 200 µl of 1×DNA Capture Buffer containing 300 mM NaCl on a rotating mixer for 3 minutes. The beads were concentrated as described above and the supernatant liquid containing the non-captured/non-methylated/hypomethylated DNA was removed, saved and stored on ice as described above. The beads were washed, mixed, concentrated with the supernatant removed and saved for one more time to collect two wash fractions. Each wash fraction was stored on ice. The wash fractions can be pooled together and labelled accordingly.

Eluting the Captured DNA

The captured DNA was eluted using an elution buffer containing 2000 mM NaCl. The beads were resuspended in 200 µl of elution buffer (2000 mM NaCl). The beads were incubated on a rotating mixer for 3 minutes and placed on the magnetic rack for 1 minute to concentrate all of the beads, and the liquid containing captured/hypermethylated DNA was removed and saved in a clean DNase-free microcentrifuge tube. The saved first fraction was stored on ice. The beads were resuspended and incubated one more time, and the liquid containing captured/methylated DNA was removed and saved in a second clean tube. The first and second collection of captured/hypermethylated DNA were pooled and stored on ice. Alternatively, multiple elutions with increasing NaCl concentration can be performed to further partition the DNA into fraction with increasing DNA methylation.

Preparation of Methylation Fractionated DNA for Analysis

Partitioned cfDNA, methylated, intermediate methylated and non-methylated DNA was purified, for example, by SPRI bead cleanup (Ampure XP, Beckman Coulter), subsequently prepared for ligation (using NEBNext® Ultra™ End Repair/dA-Tailing Module), then ligated with modified Y-shaped dsDNA adapters containing non-random molecular barcodes as described in Lanman et al., 2015. The hypermethylated, intermediate methylated and hypomethylated cfDNA partitions were ligated with 11, 12, and 12 distinct, non-random molecular barcoded adapters, respectively. Ligated, partitioned cfDNA molecules for each sample were again purified with SPRI beads (Ampure XP) then re-combined into a PCR reaction with oligos universal to all adapter-ligated molecules (NEBNext Ultra II™ Q5 master mix), amplifying all cfDNA molecules from one sample together. Amplified DNA libraries were again purified using SPRI beads (Ampure XP), in preparation for target enrichment by hybrid capture (Agilent SureSelect 30 kb panel; 'panel').

Preparation of Non-Partitioned DNA for Analysis

Powerpool cfDNA (10 or 150 ng) was prepared for ligation (using NEBNext® Ultra™ End Repair/dA-Tailing Module), then ligated with modified Y-shaped dsDNA adapters containing non-random molecular barcodes as described in Lanman et al., 2015. The cfDNA were ligated with 35 distinct, non-random molecular barcoded adapters. Ligated, cfDNA molecules for each sample were again purified with SPRI beads (Ampure XP) then placed into PCR reaction with oligos universal to all adapter-ligated molecules (NEBNext Ultra II™ Q5 master mix), amplifying all cfDNA molecules from one sample together. Amplified DNA libraries were again purified using SPRI beads (Ampure XP), in preparation for target enrichment by hybrid capture (Agilent SureSelect 30 kb panel; 'panel').

The disclosure provides methods for processing nucleic acid populations containing different forms (e.g., RNA and DNA, single-stranded or double-stranded) and/or extents of modification (e.g., cytosine methylation, association with proteins). These methods accommodate multiple forms and/or modifications of nucleic acid in a sample, such that sequence information can be obtained for multiple forms. The methods also preserve the identity of multiple forms or modified states through processing and analysis, such that analysis of sequence can be combined with epigenetic analysis.

Data Analysis

DNA libraries from different samples were pooled and sequenced on an Illumina HiSeq2500, 2×150 paired end sequencing. Bioinformatics processing was carried out as per the standard GUARDANT360™ protocol as described in Lanman et al, 2015 and elsewhere. For MBD-partitioned samples, additionally the molecular barcodes were used to identify the MBD-partition in which the DNA was fractioned (hypermethylated, intermediate methylated, and hypomethylated). At each genomic locus targeted by the panel, the aligned molecules that were hypermethylated, intermediate methylated and hypomethylated was totaled. The % hypermethylated was defined at a given loci as the fraction of total molecules spanning the loci that are hypermethylated. For both MBD-partitioned and non-partitioned DNA samples, in targeted regions, mutant allele fraction (MAF) from the reference genome was called using proprietary Guardant Health variant calling software.

Figures 25A, 25B:
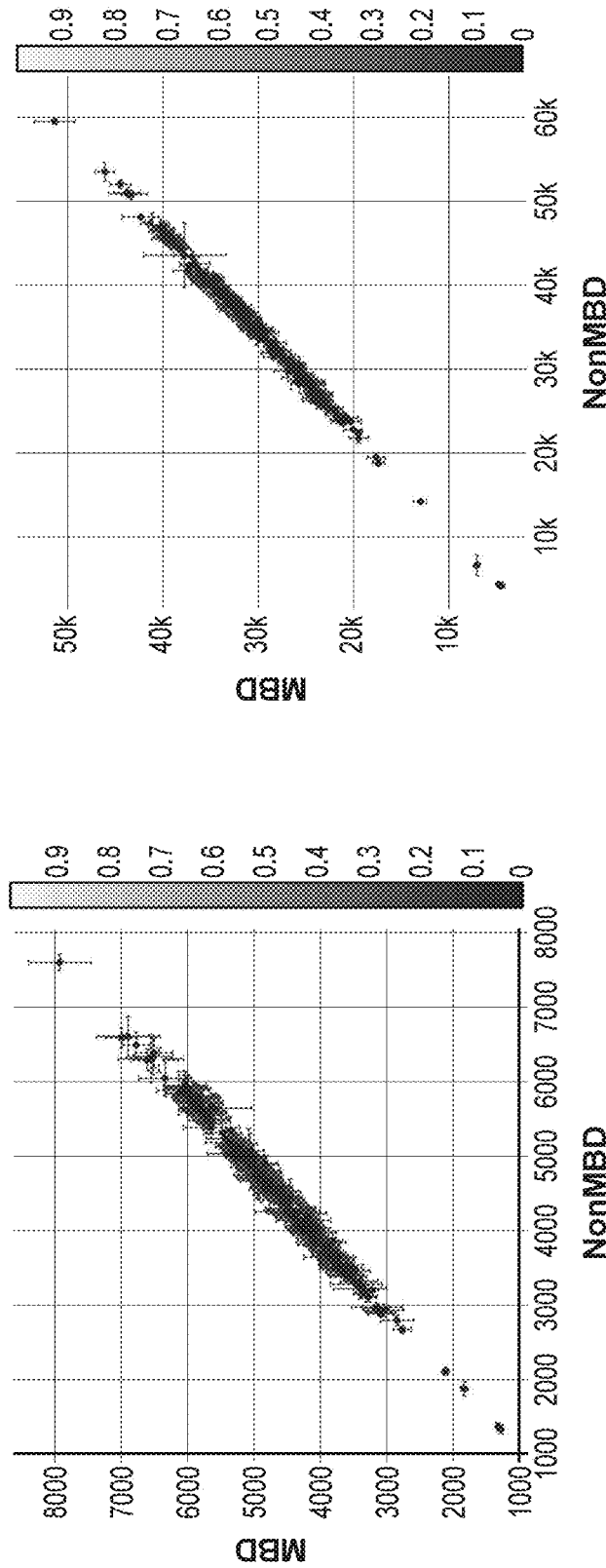
FIG. 25A and FIG. 25B show comparison between the coverage for MBD and non-MBD samples in the targeted sequencing assay.

Example 18: Comparison Between the Coverage for MBD and Non-MBD Samples in the Targeted Sequencing Assay In this example, the samples were processed as described in Example 17. Different clinical samples (PowerpoolV1 and PowerpoolV2) of cfDNA were assayed in the targeted sequencing assay with and without the MBD-partitioning, 'MBD' and 'nonMBD', in triplicates respectively. The unique molecules sequenced at each targeted genomic position for the genes from the panel was compared in the MBD and NonMBD for PowerpoolV1 at 15 ng (FIG. 25A) and 150 ng (FIG. 25B) assay input. The panel is a custom gene panel that covers about 30 kb genomic region. The panel also has higher sensitivity for detecting different cancers, such as lung cancer, colorectal cancer, etc. FIG. 25A and FIG. 25B show high efficiency recovery of molecules in targeted sequencing assay was retained with application of MBD-partitioning. Molecule counts from targeted sequencing assay of powerpoolV1 (a) 15 ng and (b) 150 ng input, either run with (Y-axis) or without MBD-partitioning. A linear correlation is observed between the MBD to nonMBD molecule counts or coverage, indicating that the MBD-partitioning does not bias the recovery of the assay.

Figure 26A:
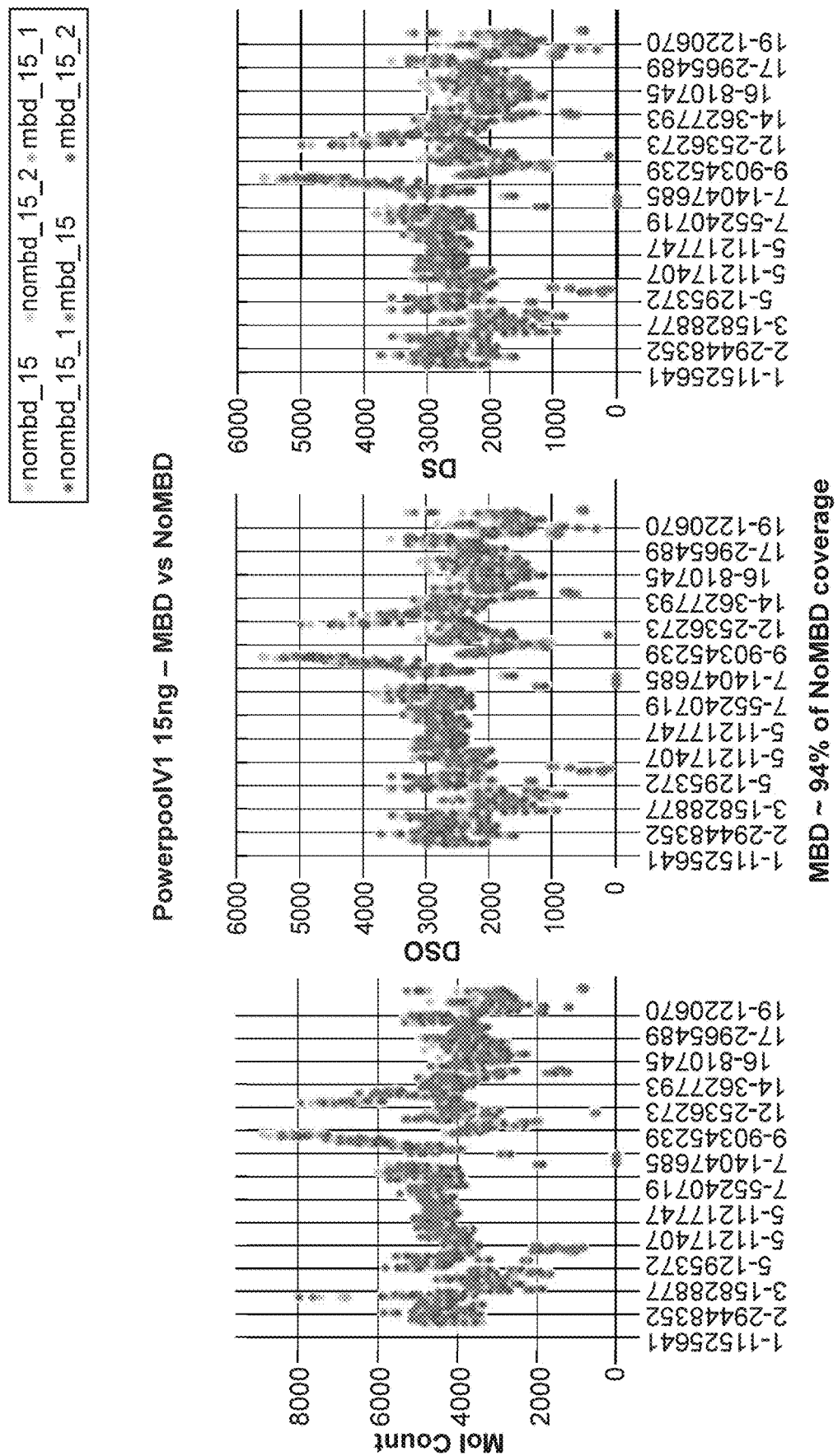
FIG. 26A and FIG. 26B show the coverage for the genes in the panel using 15 ng of cfDNA input and two clinical samples (PowerpoolV1 and PowerpoolV2).
Figure 26B:
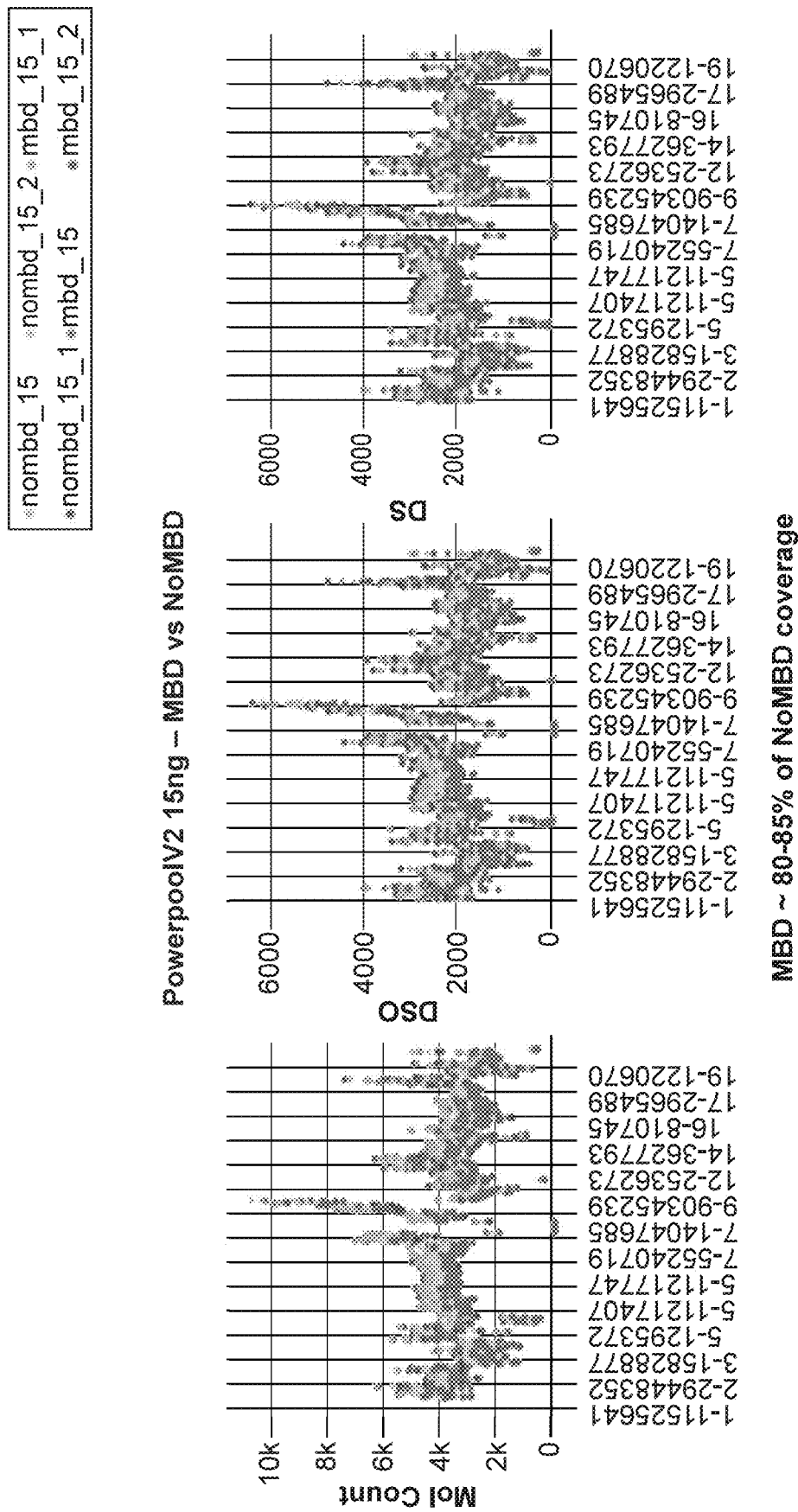
Figure 27A:
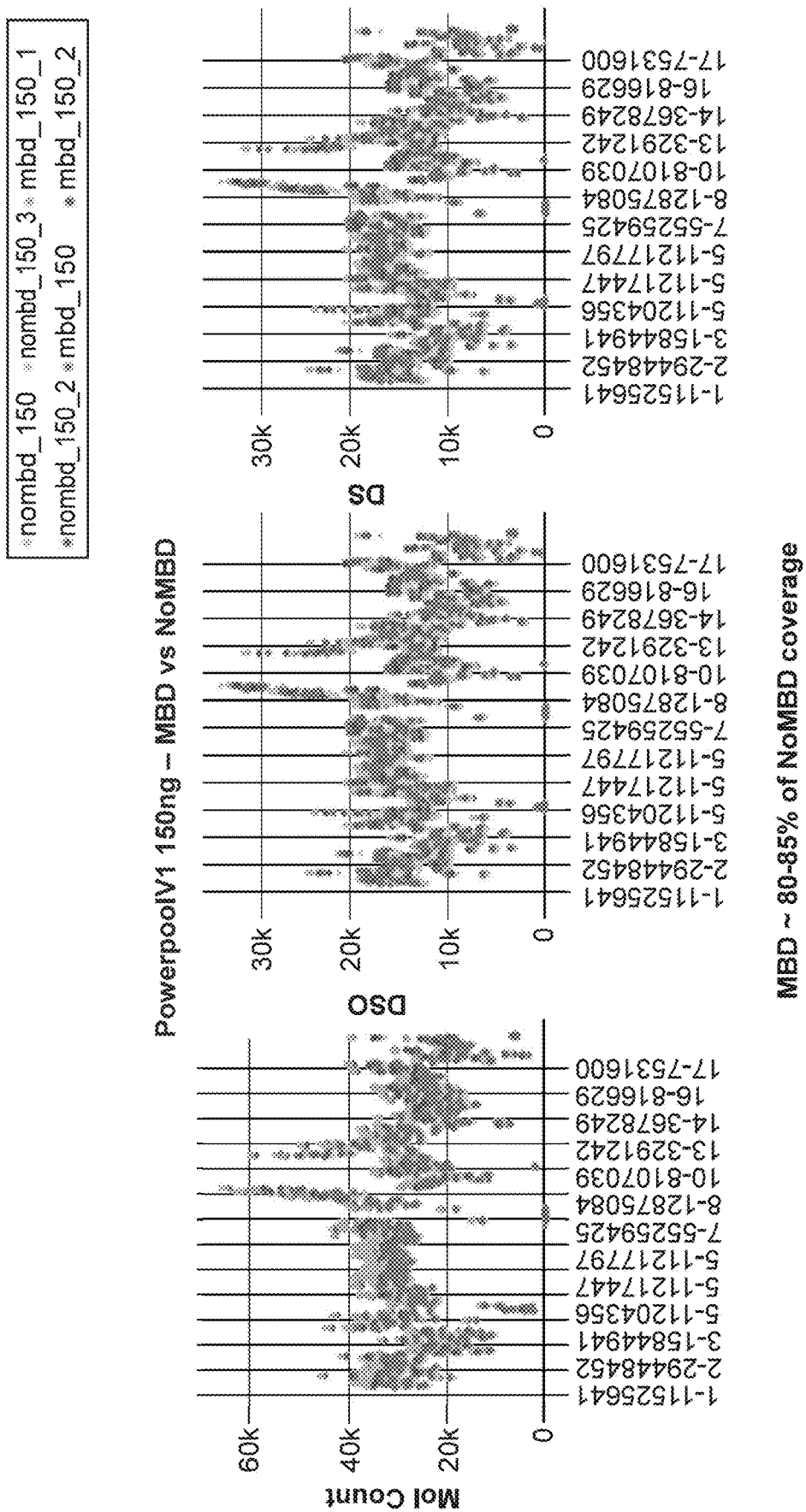
FIG. 27A and FIG. 27B show coverage for the genes in the panel using 150 ng of cfDNA input and two clinical samples (PowerpoolV1 and PowerpoolV2).
Figure 27B:
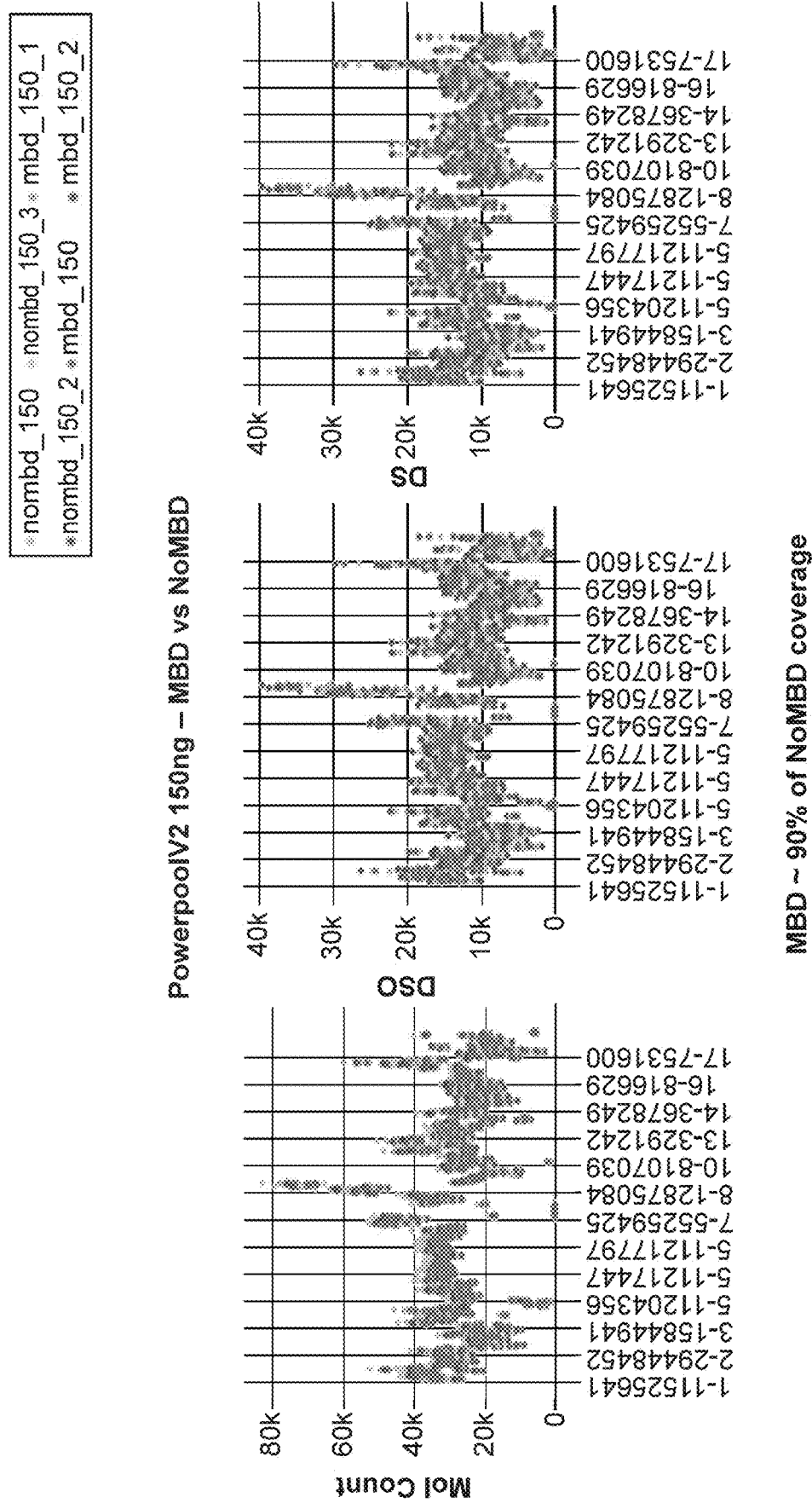

The molecule counts or coverage for the genes from the panel were compared between the nonMBD and MBD samples. The MBD and nonMBD samples were prepared using 15 ng input cfDNA extracted from two clinical samples (FIG. 26A—PowerpoolV1 and FIG. 26B—PowerpoolV2) or using 150 ng input cfDNA extracted from two clinical samples (FIG. 27A—PowerpoolV1; FIG. 27B—PowerpoolV2). X-axis for the graph on left represents molecule counts or coverage, X-axis for the graph in the center represents mutant confirmed with both paired end reads (double-stranded overlap; DSO) and X-axis for the graph on left represents molecule counts for which both DNA strands are sequenced (double stranded support; DS). A strong correlation between MBD and non-MBD samples for molecule counts, DSO and DS shows that MBD samples can capture most of the molecules (~94% as in FIG. 26A, ~80-85% as in FIG. 26B and FIG. 27A and ~90% as in FIG. 27B) when compared to non-MBD. No positional bias in molecular coverage, as well as other important variant calling metrics (DSO, DS) across the panel.

Figure 28B:
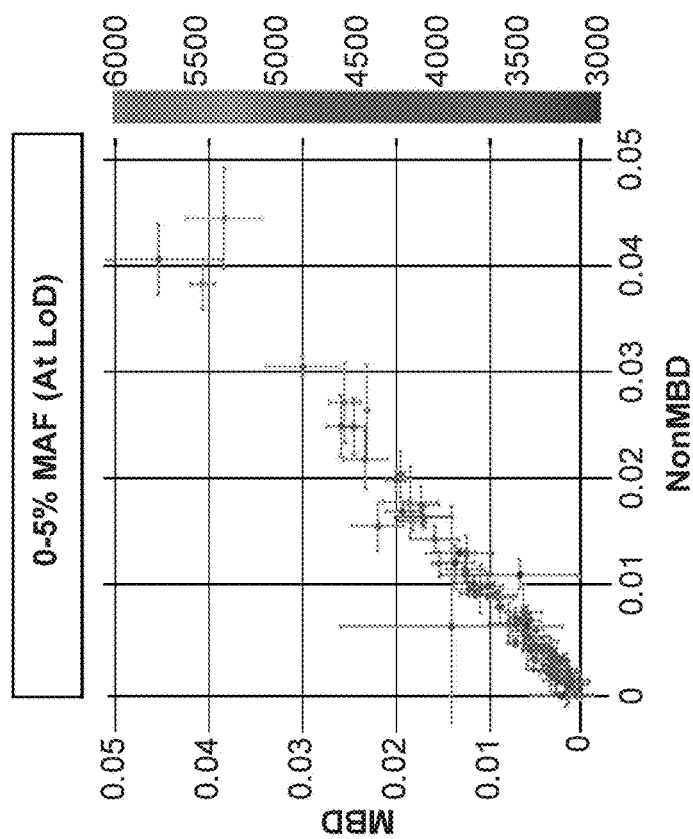
FIG. 28A, FIG. 28B and FIG. 28C show specificity and sensitivity of variant or mutation detection for the genes in the panel using 15 ng of cfDNA input.
Figure 28A:
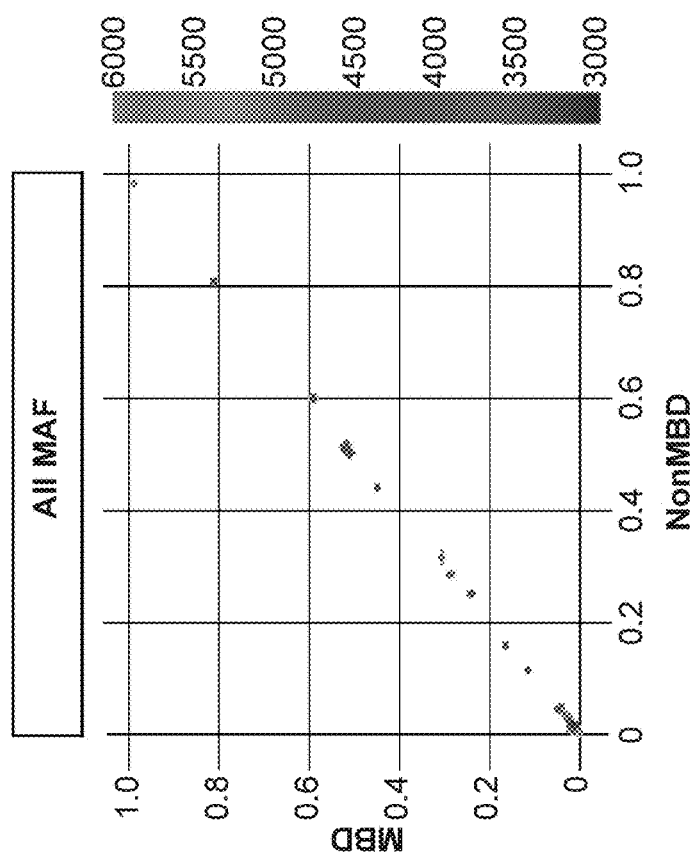
Figure 28C:
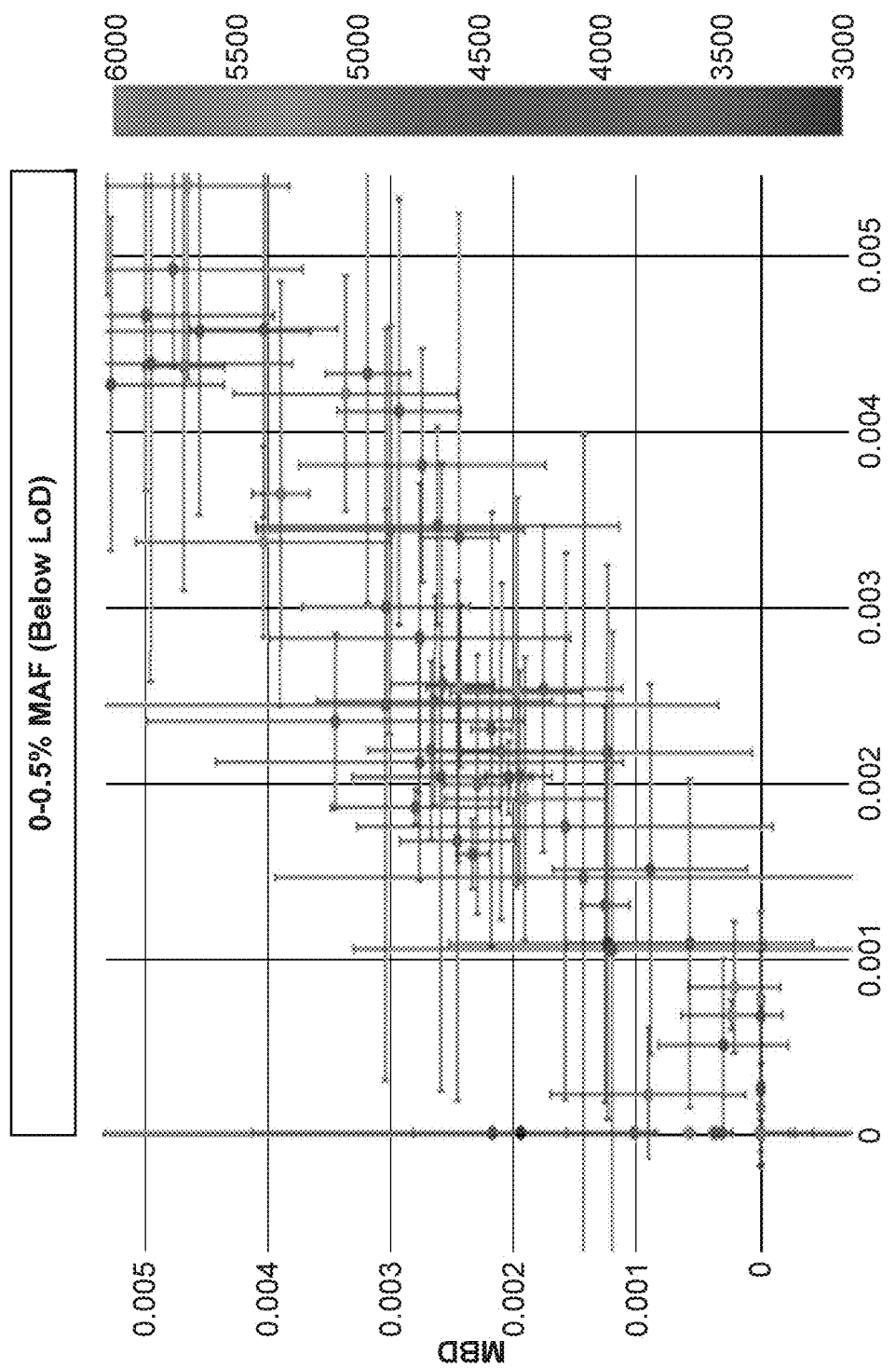
Figure 29B:
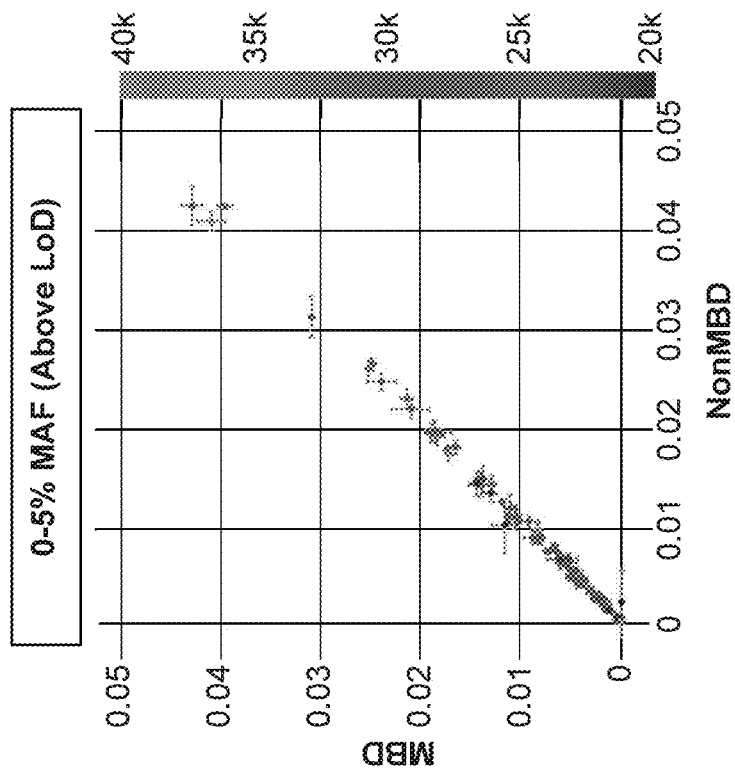
FIG. 29A, FIG. 29B and FIG. 29C show specificity and sensitivity of variant or mutation detection for the genes in the panel using 150 ng of cfDNA input.
Figure 29A:
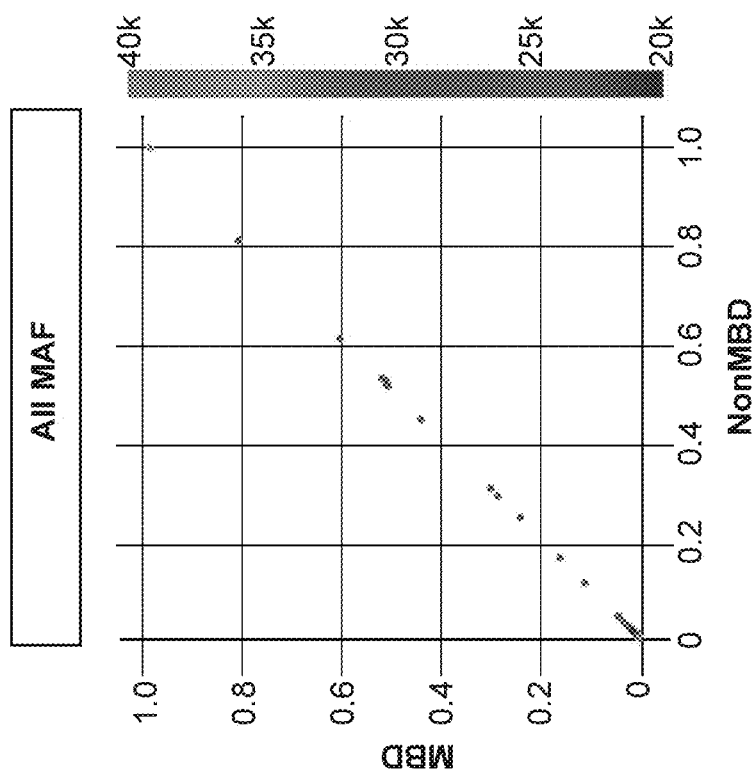
Figure 29C:
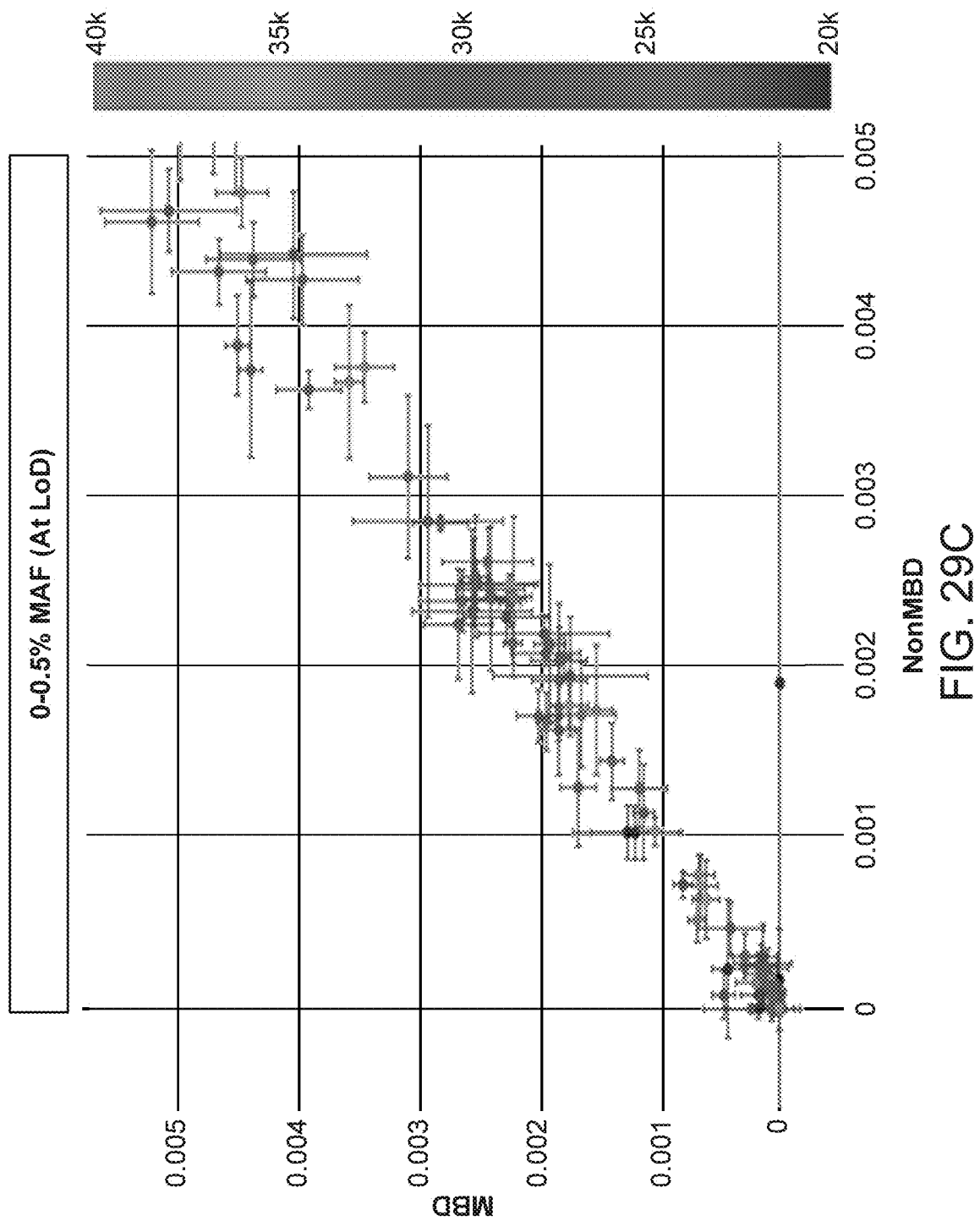
Figure 30:
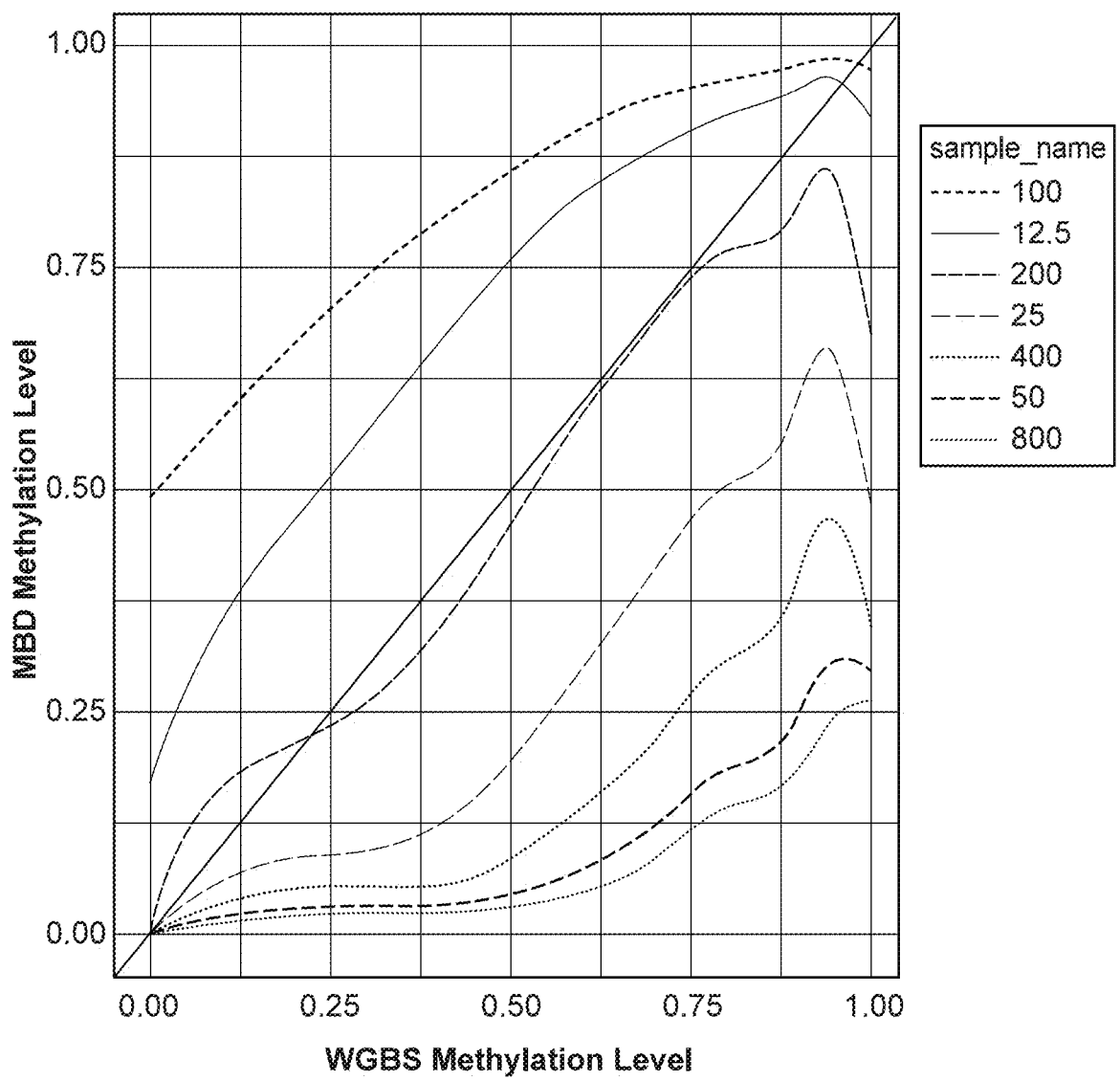
FIG. 30 shows the correlation between the average methylation levels as measured by the whole genome bisulfite sequencing (WGBS) and MBD partitioning.

Example 19: Sensitivity and Specificity of Variant Detection in MBD and nonMBD Samples In this example, the samples were processed as described in Example 17. To measure the impact on variant or mutation detection on sensitivity and specificity, mutant allele fraction (MAF) between the MBD (Y-axis) and non-MBD (X-axis) samples were compared for the genes in the panel using 15 ng input cfDNA. Different MAF ranges are plotted on X-axis, for example, 0-100% (FIG. 28A), 0-5% (FIG. 28B) and 0-0.5% (FIG. 28C). MAF values are from triplicate samples from MBD and nonMBD. MAFs determined for MBD samples were in agreement with MAFs determined for NonMBD samples. MAFs between MBD and nonMBD showed a linear correlation for the PowerpoolV1 with 15 ng input (FIG. 28A; 0-100%) and at a lower limit of detection (FIG. 28B; 0-5%). MAFs between MBD and nonMBD did not correlate well below the limit of detection (FIG. 28C; 0-0.5% MAF). Similarly, MBD and nonMBD samples showed agreement in MAFs with 150 ng cfDNA input (FIG. 29A and FIG. 29B) from PowerpoolV1 but there was not a strong agreement in the 0-0.5% range (FIG. 29C).

Example 20: Methylation Profiling of Promoter Region Using Whole Genome Sequencing Molecular partitioned samples may enhance analysis of genome architecture such as cell-free DNA fragment occupancy and detection of cancer. For example, transcription-relevant hypermethylation events can be detected by taking cell-free DNA fragment occupancy into account when analyzing promoter regions of tumor suppressing genes that are usually targeted by cancer via methylation-driven gene silencing. One may co-examine cell-free DNA fragment occupancy signal and hypermethylated fraction in different MBD partitions to validate the feasibility of MBD-driven discovery of transcription-relevant hypermethylation events and gene silencing in cancer samples.

Figure 23:
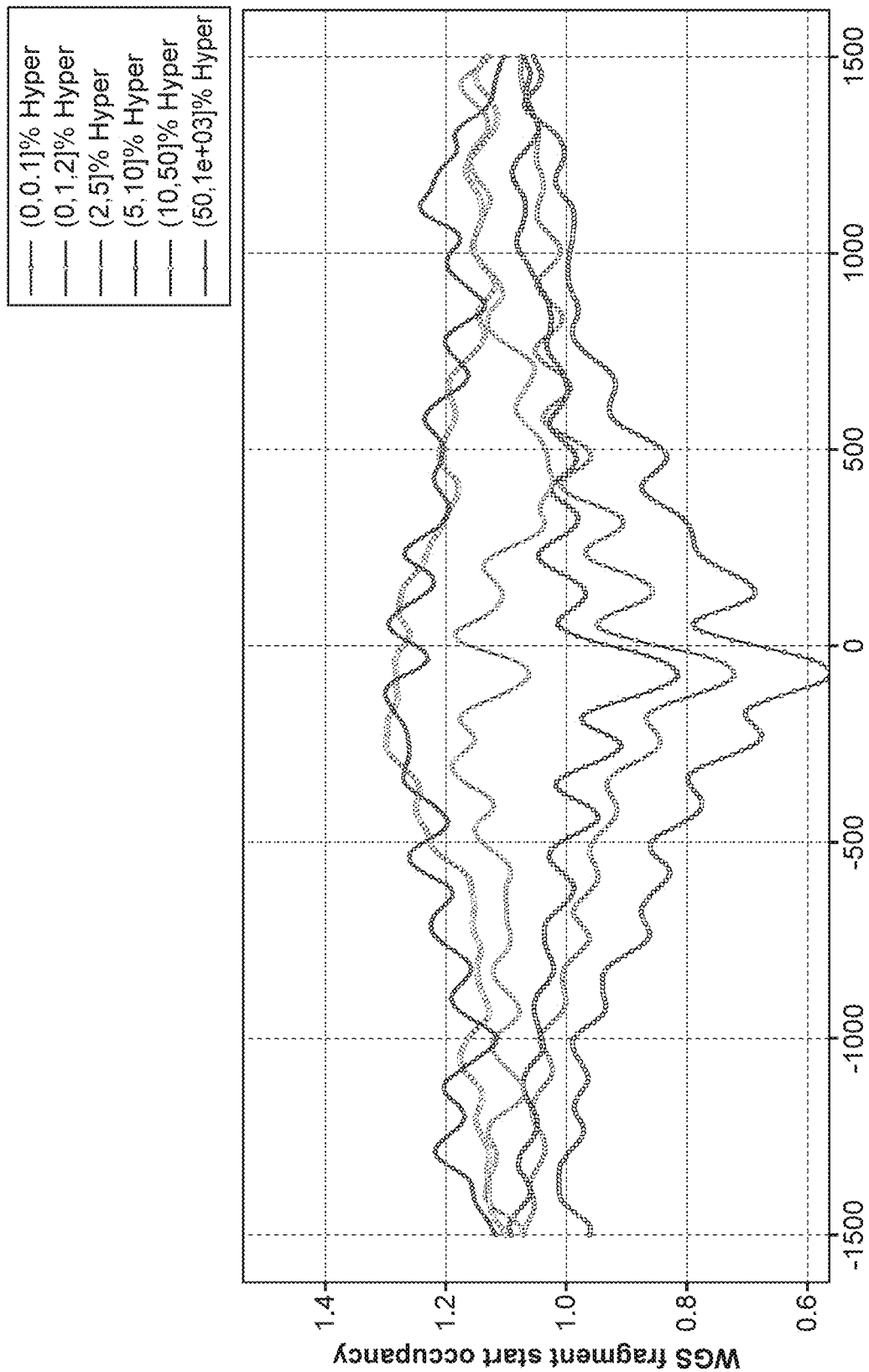
FIG. 23 shows methylation profiling of promoter region using whole genome sequencing.

As an illustrating example, one may use publically available gencode (v26lift37) data to produce percentage hypermethylated (number of fragments in hypermethylated partition/total number of fragments in all MBD partitions) in TSS regions of all gencode genes within available cohort of non-malignant healthy adults. Cell-free DNA fragment occupancy signal may be aggregated across a cohort of non-malignant healthy adults. All TSSs may be binned based on percentage hypermethylated fraction observed in MBD partitioning assay. Fragment occupancy in non-MBD WSG cohort in each bin may be examined. FIG. 23 shows correlation of gene expression and methylation status. Shown is WGS occupancy at promoter profile versus percentage MBD methylation. As seen in FIG. 23, hypomethylated DNA (0-0.1% hyper) has low fragment occupancy coverage in the vicinity of TSS, while hypermethylated DNA (10-50% hyper or >50% hyper) has high fragment occupancy coverage and distinct NDR in the vicinity of TSS. In some cases, fragment occupancy coverage of hypomethylated DNA is used to normalize sequence depth and/or mappability of sequences. Percentage of hypermethylated or hypomethylated nucleic acid fragments can be determined by dividing number of hypermethylated or hypomethylated cell-free fragments by the total number of cell free DNA fragments observed across all partitions.

Example 21: Comparison Between the Methylation Levels in the MBD Samples and the Whole Genome Bisulfite Sequencing (WGBS) Samples To assess the methylation levels of the fragments in various partitions prepared by using the MBD protocol, a well characterized sample, NA12878 (catalog.coriell.org/0/Sections/Search/Sample_Detail.aspx?Ref=GM12878), was used. The sample was partitioned into hyper-, hypo- and intermediated methylated portioning followed by recombining of the partitions in silico (MBD sample) as described in Example 1. The MBD sample was compared it to a publically available, standard methylation data set (basespace.illumina.com/datacentral (HiSeq 4000: TruSeq DNA Methylation (NA12878, 1×151), which utilizes whole genome bisulfite sequencing (WGBS). WGBS interrogates the methylation status of individual cytosines. FIG. 31 shows the correlation of the average methylation level as measured by WGBS (X-axis) and MBD (Y-axis) in 160 bp windows. The MBD methylation level was computed by dividing the number of reads in the hypermethylated partition falling in that window divided by the total number of reads in the hyper- and hypomethylated partitions. The WGBS methylation level was computed by dividing the number of methylated bases by the number of methylated and unmethylated bases in the window. This experiment was run over several different bead ratios, which affects the partitioning of methylated fragments. Fewer beads restrict the hypermethylated partition to highly methylated fragments (i.e., makes the assay more specific to methylation) and more beads decrease the amount of methylation needed to get a fragment into the hyper partition (i.e., makes the assay more sensitive to methylation). Empirically, input DNA:beads ratio of 1:50 was found to correlate between the fragments partitioned and their methylation levels. These results indicate that the MBD partitioning does accurately reflect the underlying methylation status of the samples.

Figure 31A:
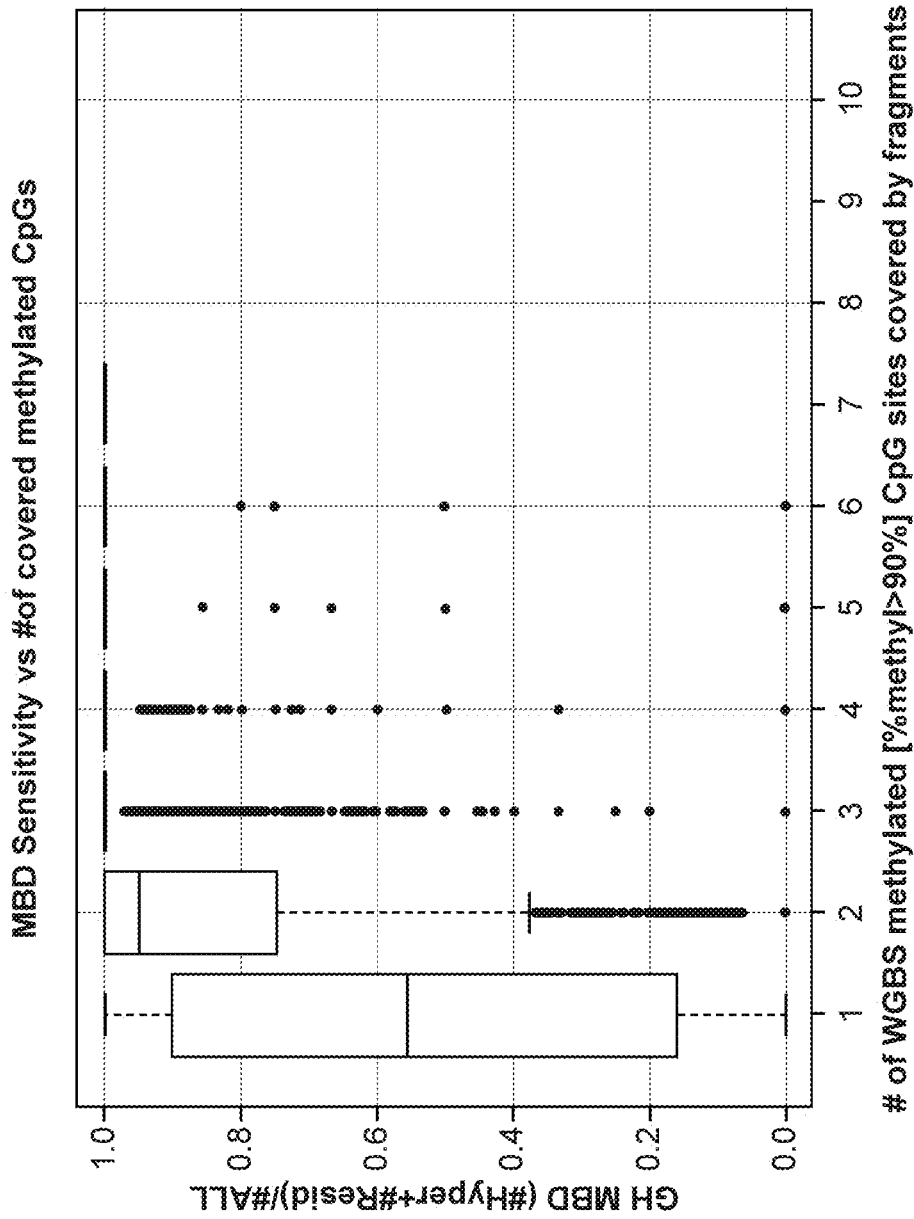
FIG. 31A and FIG. 31B show sensitivity (FIG. 31A) and specificity (FIG. 31B) of detecting methylated DNA using MBD partitioning (Y-axis) and using the whole genome bisulfite sequencing assay (WGBS, X-axis).
Figure 31B:
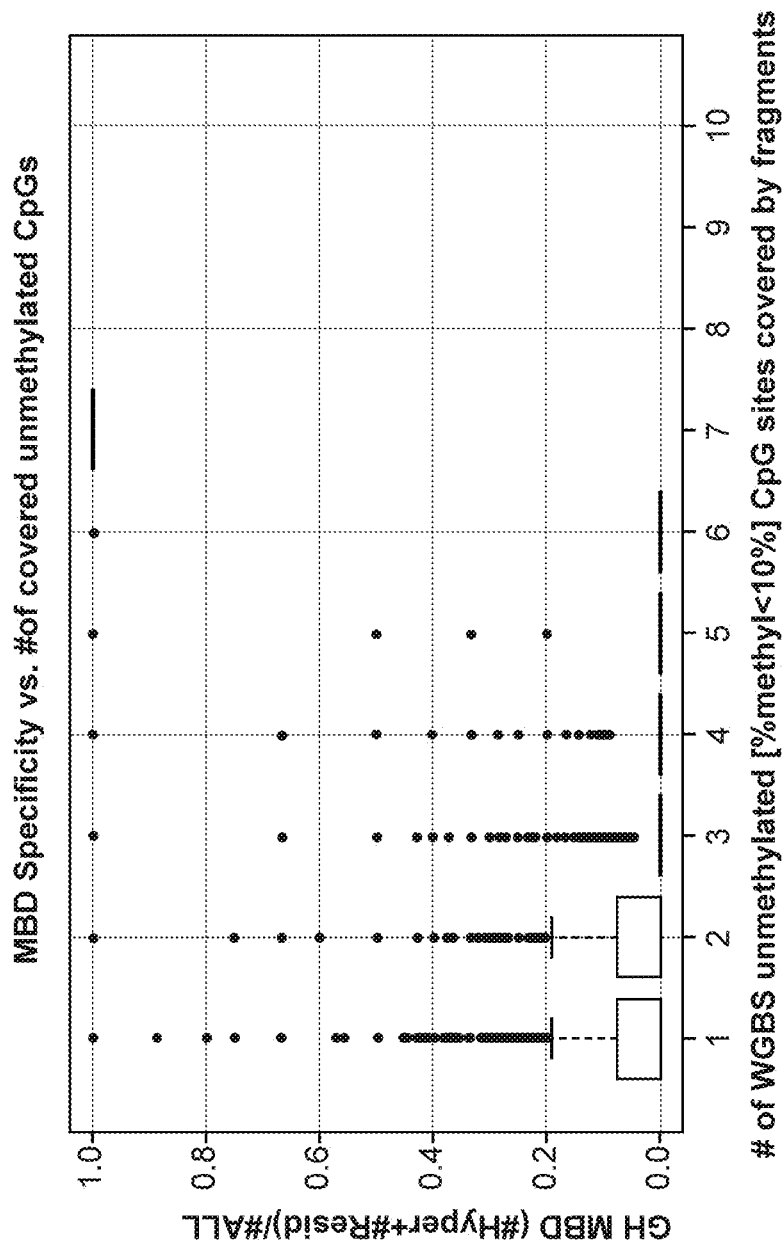

In this analysis, the effect of the number of CG sites in a fragment on that fragment's partitioning was determined. Fragments that are publically available with standard methylation data set (NA12878; same as in the previous analysis) that indicate highly hyper- or hypomethylated (whole genome bisulfite sequencing methylation level >90% or <10% as calculated in the previous analysis) were selected for analysis. These fragments were stratified by the number of CG sites they contained. Highly methylated fragments with 3 or more CG sites ended up in the hypermethylated partition, indicating that the assay is sensitive to small amounts of methylation (FIG. 31A). Conversely, fragments devoid of methylation were partitioned predominantly into the hypomethylated partition regardless of the number of CG sites in the fragment, indicating that the assay has a high degree of specificity (FIG. 31B).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Some Embodiments of the Invention

Provided below are some embodiments of the invention provided in patent claim format.

---

What is claimed is:

1. A method of analyzing nucleic acids for detecting cancer recurrence, comprising:
   (a) purifying cell-free nucleic acids from a bodily fluid sample obtained from a subject;
   (b) physically fractionating the cell-free nucleic acids to generate two or more partitions, wherein the physical fractionating comprises fractionating nucleic acids based on one or more characteristics, wherein the one or more characteristics comprises methylation status;
   (c) sequencing at least a portion of nucleic acids from each of the two or more partitions at a sequence read depth of at least about five thousand sequence reads per base to generate a set of sequencing reads; and
   (d) analyzing the set of sequence reads to detect the one or more characteristics.

2. The method of claim 1, further comprising attaching NGS-enabling adapters comprising differential molecular tags to each of the two or more partitions to generate molecular tagged partitions.

3. The method of claim 2, wherein the differential molecular tags are different sets of molecular tags corresponding to a partition.

4. The method of claim 1, wherein the physically fractionating comprises fractionating with methyl-binding domain protein ("MBD")-beads to stratify into various degrees of methylation.

5. The method of claim 1, wherein at least one partition comprises hypermethylated DNA.

6. The method of claim 1, wherein the physically fractionating comprises separating DNA molecules using immunoprecipitation.

7. The method of claim 4, wherein the various degrees of methylation comprise hypermethylation and hypomethylation.

8. The method of claim 1, further comprising, prior to sequencing, amplifying a subset of the cell-free nucleic acids from the two or more partitions to generate amplified nucleic acids.

9. The method of claim 2, further comprising re-combining one or more molecular tagged partitions.

10. The method of claim 9, further comprising enriching the re-combined one or more molecular tagged partitions for a plurality of genomic regions.

11. The method of claim 10, wherein the plurality of genomic regions comprises differentially methylated regions.

12. The method of claim 10, wherein the enriching is performed by hybridization of amplified nucleic acids to RNA or DNA probes.

13. The method of claim 1, further comprising
   (d) determining a quantitative measure obtained from the set of sequencing reads in the two or more partitions; and
   (e) determining the presence or absence of cancer.

14. The method of claim 13, further comprising mapping the set of sequencing reads to one or more loci on a reference sequence.

15. The method of claim 13, further comprising using a trained classifier to classify the one or more characteristics as associated with a type of cancer in the subject.

16. The method of claim 15, wherein the type of cancer comprises colorectal cancer, breast cancer, lung cancer, brain cancer, skin cancer, prostate cancer, nose cancer, throat cancer, liver cancer, bone cancer, lymphomas, pancreatic cancer, bowel cancer, thyroid cancer, bladder cancer, kidney cancer, mouth cancer, or stomach cancer.

17. The method of claim 1, wherein the one or more characteristics further comprises glycosylation status, histone modification, nucleosome positioning, nucleosome modification, or a DNA-protein interaction.

18. The method of claim 1, wherein the subject has previously been diagnosed with cancer.

19. The method of claim 1, wherein the cell-free nucleic acids comprise circulating tumor DNA.

20. The method of claim 1, wherein the bodily fluid sample is blood, serum or plasma.

21. The method of claim 1, wherein the cell-free nucleic acids purified from the bodily fluid sample is up to about 50 ng, 100 ng, 200 ng, 300 ng, 400 ng, or 500 ng.

22. The method of claim 1, wherein the subject has been treated with one or more cancer therapies.

23. The method of claim 22, wherein the one or more cancer therapies is selected from the group consisting of chemotherapies, antibodies, vaccines and biologics.

* * * * *